(12) United States Patent
Jorgensen et al.

(10) Patent No.: US 9,914,709 B2
(45) Date of Patent: Mar. 13, 2018

(54) COMPOSITIONS AND METHODS OF TREATING HIV-1 INFECTIONS USING SAME

(71) Applicant: YALE UNIVERSITY, New Haven, CT (US)

(72) Inventors: William L. Jorgensen, Deep River, CT (US); Karen S. Anderson, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 14/310,564

(22) Filed: Jun. 20, 2014

(65) Prior Publication Data

US 2014/0378443 A1    Dec. 25, 2014

Related U.S. Application Data

(60) Provisional application No. 61/837,939, filed on Jun. 21, 2013, provisional application No. 61/840,554, filed on Jun. 28, 2013.

(51) Int. Cl.
| | |
|---|---|
| *C07D 239/48* | (2006.01) |
| *A61K 45/06* | (2006.01) |
| *A61K 31/536* | (2006.01) |
| *A61K 31/551* | (2006.01) |
| *A61K 31/53* | (2006.01) |
| *C07D 251/52* | (2006.01) |
| *A61K 31/5377* | (2006.01) |
| *A61K 31/505* | (2006.01) |

(52) U.S. Cl.
CPC .......... *C07D 239/48* (2013.01); *A61K 31/505* (2013.01); *A61K 31/53* (2013.01); *A61K 31/536* (2013.01); *A61K 31/5377* (2013.01); *A61K 31/551* (2013.01); *A61K 45/06* (2013.01); *C07D 251/52* (2013.01)

(58) Field of Classification Search
None
See application file for complete search history.

(56) References Cited

U.S. PATENT DOCUMENTS 7,125,879 B2   10/2006   Guillemont et al.
7,375,222 B2 *  5/2008   Kubota .................. A61K 31/53
                                                544/197

FOREIGN PATENT DOCUMENTS

EP              945447 A1 *   9/1999  .......... C07D 251/70
WO     WO 1999/050250         10/1999

OTHER PUBLICATIONS

Database CAPLUS in STN, Acc. No. 1968:114661, Abdrakhmanov et al., SU 191570 (Jan. 26, 1967) (abstract).*
Database CAPLUS in STN, Acc. No. 1911:8803, Von Meyer, Journal fuer Praktische Chemie (1911), 82, pp. 521-538 (abstract).*
Database CAPLUS in STN, Acc. No. 1974:4360, Crook et al., DE 2307777 A1 (Aug. 23, 1973) (abstract).*
Database CAPLUS in STN, Acc. No. 2003:633512, Kubota et al., WO 2003066099 A1 (Aug. 14, 2003) (abstract).*
Database CAPLUS in STN, Acc. No. 1999:631416, Kukla et al., EP 945447 A1 (Sep. 29, 1999).*
Ekkati et al., 2012, Discovery of dimeric inhibitors by extension into the entrance channel of HIV-1 reverse transcriptase, Bioorganic & Medicinal Chemistry Letters 22:1665-1568.
Molina et al., 2011, Rilpivirine versus efavirenz with tenofovir and emtricitabine in treatment-naive adults infected with HIV-1 (ECHO): a phase 3 randomised double-blind active-controlled trial, Lancet 378:238.
Janssen et al., 2005, In Search of a Novel Anti-HIV Drug: Multi-disciplinary Coordination in the Discovery of 4-[[4-[[4-[(1E)-2-Cyanoethenyl]-2,6-dimethylphenyl]amino]-2-pyrimidinyl]amino]benzonitrile (R278474, Rilpivirine,) J. Med. Chem. 48:1901.
Frenkel et al., 2005, Concentration and pH dependent aggregation of hydrophobic drug molecules and relevance to oral bioavailability, J. Med. Chem. 48:1974.
Saxena et al., 2009, Sustained release of microbicides by newly engineered vaginal rings, AIDS 23:917.
Jorgensen, 2009, Efficient drug lead discovery and optimization, Acc. Chem. Res. 42:724.
Jorgensen et al., 2011, Efficient Discovery of Potent Anti-HIV Agents Targeting the Tyr181Cys Variant of HIV Reverse Transcriptase, J. Am. Chem. Soc. 22:15686.
Jorgensen and Duffy, 2002, Prediction of drug solubility from structure, Adv. Drug Deliv. Rev. 54:355.
Bollini et al., 2011, Computationally-guided optimization of a docking hit to yield catechol diethers as potent anti-HIV agents, J. Med. Chem. 54:8582.
Frey et al., 2012, Crystal structures of HIV-1 reverse transcriptase with picomolar inhibitors reveal key interactions for drug design, J. Am. Chem. Soc. 134:19501.
Das et al., 2004, Roles of Conformational and Positional Adaptability in Structure-Based Design of TMC125-R165335 (Etravirine) and Related Non-nucleoside Reverse Transcriptase Inhibitors That Are Highly Potent and Effective against Wild-Type and Drug-Resistant HIV-1 Variants, J. Med. Chem., 47:2550.
Leung et al., 2010, Eastern extension of azoles as non-nucleoside inhibitors of HIV-1 reverse transcriptase; cyano group alternatives, Bioorg. Med. Chem. Lett. 20:2485.

* cited by examiner

*Primary Examiner* — Brian J Davis
(74) *Attorney, Agent, or Firm* — Riverside Law LLP

(57) ABSTRACT

The present invention includes novel compositions useful for preventing or treating an HIV-1 infection in a subject in need thereof. The present invention further includes a novel method of preventing or treating an HIV-1 infection in a subject in need thereof, the method comprising administering to the subject an effective amount of a compound of the invention. In one embodiment, the subject is further administered at least one additional therapeutic agent.

18 Claims, 13 Drawing Sheets

COMPOSITIONS AND METHODS OF TREATING HIV-1 INFECTIONS USING SAME

CROSS-REFERENCE TO RELATED APPLICATIONS

The present application claims priority to U.S. Provisional Application No. 61/837,939, filed Jun. 21, 2013, and U.S. Provisional Application No. 61/840,554, filed Jun. 28, 2013, each of which applications are incorporated by reference herein in their entireties.

STATEMENT REGARDING FEDERALLY SPONSORED RESEARCH OR DEVELOPMENT

This invention was made with government support under AI044616, GM049551, GM032136 awarded by National Institutes of Health. The government has certain rights in the invention.

BACKGROUND OF THE INVENTION

Non-nucleoside inhibitors of HIV-1 reverse transcriptase (NNRTIs) are a central component of anti-HIV therapy (Prajapati et al., 2009, Bioorg. Med. Chem. 17:5744; de Bethune, 2010, Antiviral Res. 85:75). There are five FDA-approved NNRTI drugs: nevirapine, delavirdine, efavirenz, etravirine, and rilpivirine. In view of the rapid mutation of the virus, NNRTIs are given in combination therapies. Though the NNRTI class has demonstrated utility in treating HIV, further improvements are necessary to address issues of safety, administration and virologic failure (Chiao et al., 2009, Curr. Opin. Drug Disc. Dev. 12:53; Adams et al., 2010, Ann. Pharmacotherapy 44:157; Molina et al., 2011, Lancet 378:238). There is also need to respond to the emergence of pan-resistant viral variants and unknown effects of long-term treatment (Richman et al., 2009, Science 323:1304).

Among the five FDA-approved NNRTI drugs, the most recent drugs are etravirine and rilpivirine. These diarylpyrimidines are very active in cell assays against variant forms of HIV-1 that incorporate mutations in the vicinity of the NNRTI binding site (Gillemont et al., 2005, J. Med. Chem. 48:2072; Janssen et al., 2005, J. Med. Chem. 48:1901). The earliest approved NNRTIs (nevirapine and delavirdine) have poor activity against most common mutations. Though the second-generation compound efavirenz performs well against variants bearing the clinically prevalent Tyr181 Cys mutation, resistance arises from other common variants such as those including Lys103Asn (de Bethune, 2010, Antiviral Res. 85:75; Gillemont et al., 2005, J. Med. Chem. 48:2072; Janssen et al., 2005, J. Med. Chem. 48:1901). The clinical significance of efavirenz and rilpivirine is particularly great since they are incorporated into the once-a-day combination therapies Atripla and Complera, respectively (Permpalung et al., 2012, Expert Opin. Pharmacotherapy 13:2301). The other two active components of these pills are the same—the nucleosides emtricitabine and tenofovir. Though the performance in cell-based assays is far better for rilpivirine than for efavirenz, surprisingly more virologic failure is observed for patients under treatment with Complera than Atripla (Permpalung et al., 2012, Expert Opin. Pharmacotherapy 13:2301; Molina et al., 2011, Lancet 378:238; Lyseng-Willamson and Scott, 2012, Clin. Drug Investig. 32:715). These results highlight the need for improvements in the NNRTI class, including novel agents that allow for lower dosages and side effects. In particular, aminoazine NNRTIs have poor solubility, which often leads to low bioavailability, difficulties in formulation, and accumulation in fatty tissues (Lipinski et al., 2001, Adv. Drug Deliv. Rev. 46:3; Jorgensen and Duffy, 2002, Adv. Drug Deliv. Rev. 54:355).

Most oral drugs have aqueous solubility (S) in the range $10^{-5}$ to $10^{-2}$ M, which for a drug with a molecular weight of 400 corresponds to 4 to 4,000 μg/mL. Rarely does an FDA-approved oral drug have S near neutral pH below $10^{-6}$ M (Jorgensen and Duffy, 2002, Adv. Drug Deliv. Rev. 54:355). However, rilpivirine is practically insoluble in water (20 ng/mL at pH 7.0) (Janssen et al., 2005, J. Med. Chem. 48:1901), which translates to S of $5 \times 10^{-8}$ M. This drug appears to have an unusual absorption mechanism involving aggregates (Frenkel et al., 2005, J. Med. Chem. 48:1974). For etravirine, the solubility is also much lower than 1 μg/mL, and extensive formulation work was needed to bring the daily dosage to 0.4 g per day (Weuts et al., 2011, J. Pharm. Sci. 100:260).

In view of its low solubility, dapivirine is being evaluated as a vaginal microbicide (Saxena et al., 2009, AIDS 23:917). This was also the fate of UC-781, an early NNRTI with poor solubility (<30 ng/mL) (Yang et al., 2008, AAPS J. 10:606). Interestingly, the daily dosage for nevirapine, like etravirine, is 0.4 g despite the fact that its potency towards wild-type HIV-1 is ca. 100-fold less than for etravirine. An important factor is undoubtedly that the observed aqueous solubility of nevirapine is 167 μg/mL (Morelock et al., 1994, J. Pharm. Sci. 83:948). This observation demonstrates that it is possible to have a viable NNRTI that has an $EC_{50}$ of ca. 100 nM in cell assays, if the compound has good solubility and bioavailability.

There is a need in the art for non-nucleoside compounds with improved solubility that inhibit HIV-1 reverse transcriptase. These compounds should be useful for the treatment of HIV-1 infection. The present invention addresses this unmet need.

SUMMARY OF THE INVENTION

The present invention includes a composition comprising at least one compound of formula (I):

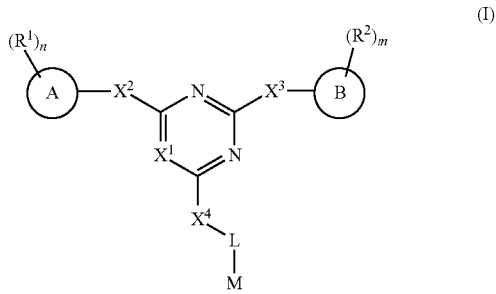

wherein in formula (I):
ring A and ring B are each independently aryl or heterocyclic;
each occurrence of $R^1$, $R^2$ and $R^3$ is independently selected from the group consisting of H, —$C_1$-$C_6$ alkyl, —$C_1$-$C_6$ cycloalkyl, —$C_1$-$C_6$ alkenyl, —$C_1$-$C_6$ fluoroalkyl, —$C_1$-$C_6$ heteroalkyl, —F, —Cl, —Br, —I, —CN, —$NO_2$, —$R^6$, —$OR^6$, —$SR^6$, —S(=O)$R^6$, —S(=O)$_2R^6$, —NHS(=O)$_2R^6$, —C(=O)$R^6$, —OC(=O)$R^6$, —$CO_2R^6$, —$OCO_2R^6$, —CH($R^6$)$_2$, —N($R^6$)$_2$, —C(=O)N($R^6$)$_2$, —OC (=O)N(R$^6$)$_2$, —NHC(=O)NH(R$^6$), —NHC(=O)R$^6$, —NHC(=O)OR$^6$, —C(OH)(R$^6$)$_2$, and —C(NH$_2$)(R$^6$)$_2$, wherein the alkyl, cycloalkyl, and alkenyl groups are optionally substituted;

each occurrence of R$^4$ and R$^5$ is each independently selected from the group consisting of H, C$_1$-C$_6$ alkyl, C$_1$-C$_6$ heteroalkyl, C$_3$-C$_{10}$ cycloalkyl, —C$_1$-C$_3$ alkyl-(C$_3$-C$_6$ cycloalkyl), (C$_4$-C$_{10}$)heterocyclyl, —C$_1$-C$_3$ alkyl-(C$_4$-C$_{10}$ heterocyclyl), (C$_6$-C$_{10}$)aryl, —C$_1$-C$_3$ alkyl-(C$_6$-C$_{10}$ aryl), (C$_5$-C$_{10}$)heteroaryl, and —C$_1$-C$_3$ alkyl-(C$_5$-C$_{10}$ heteroaryl), wherein the alkyl, heteroalkyl, cycloalkyl, heterocyclyl, aryl and heteroaryl groups are optionally substituted;

each occurrence of R$^6$ is independently selected from the group consisting of H, C$_1$-C$_6$ alkyl, C$_1$-C$_6$ heteroalkyl, C$_2$-C$_6$ alkenyl, 2-cyanovinyl, and —C$_1$-C$_3$ alkyl-(C$_3$-C$_6$ alkenyl), wherein the alkyl, heteroalkyl, or alkenyl groups are optionally substituted;

X$^1$ is CR$^3$ or N;

X$^2$, X$^3$ and X$^4$ are each independently selected from the group consisting of —O—, —C(R$^3$)$_2$—, —S— and —NR$^4$—;

L is —(CH$_2$)$_y$—, wherein one or more —CH$_2$— groups in L are independently and optionally replaced with —O—, —S— or —NR$^4$—,
with the provisos that: no heteroatom-heteroatom bond exist within L, and L is not covalently linked to X$^4$ or M through a heteroatom-heteroatom bond;

M is —OR$^5$, —SR$^5$, —N(R$^5$)$_2$—, aryl or heterocyclyl, wherein the aryl or heterocyclyl are independently optionally substituted;

m and n are each independently an integer from 0-5; and,
y is an integer from 0-19,
a salt, solvate, or N-oxide thereof.

In one embodiment, the at least one compound of formula (I) is a compound of formula (Ia):

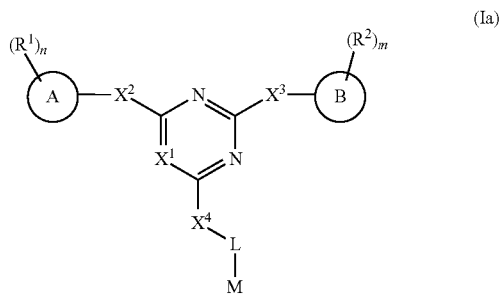

(Ia)

wherein in formula (Ia):
ring A and ring B are each independently aryl or heterocyclic;

each occurrence of R$^1$, R$^2$ and R$^3$ is independently selected from the group consisting of H, —C$_1$-C$_6$ alkyl, —C$_1$-C$_6$ cycloalkyl, —C$_1$-C$_6$ alkenyl, —C$_1$-C$_6$ fluoroalkyl, —C$_1$-C$_6$ heteroalkyl, —F, —Cl, —Br, —I, —CN, —NO$_2$, —R$^6$, —OR$^6$, —SR$^6$, —S(=O)R$^6$, —S(=O)$_2$R$^6$, —NHS(=O)$_2$R$^6$, —C(=O)R$^6$, —OC(=O)R$^6$, —CO$_2$R$^6$, —OCO$_2$R$^6$, —CH(R$^6$)$_2$, —N(R$^6$)$_2$, —C(=O)N(R$^6$)$_2$, —OC(=O)N(R$^6$)$_2$, —NHC(=O)NH(R$^6$), —NHC(=O)R$^6$, —NHC(=O)OR$^6$, —C(OH)(R$^6$)$_2$, and —C(NH$_2$)(R$^6$)$_2$, wherein the alkyl, cycloalkyl, and alkenyl groups are optionally substituted;

each occurrence of R$^4$ and R$^5$ is each independently selected from the group consisting of H, C$_1$-C$_6$ alkyl, C$_1$-C$_6$ heteroalkyl, C$_3$-C$_{10}$ cycloalkyl, —C$_1$-C$_3$ alkyl-(C$_3$-C$_6$ cycloalkyl), (C$_4$-C$_{10}$)heterocyclyl, —C$_1$-C$_3$ alkyl-(C$_4$-C$_{10}$ heterocyclyl), (C$_6$-C$_{10}$)aryl, —C$_1$-C$_3$ alkyl-(C$_6$-C$_{10}$ aryl), (C$_5$-C$_{10}$)heteroaryl, and —C$_1$-C$_3$ alkyl-(C$_5$-C$_{10}$ heteroaryl), wherein the alkyl, heteroalkyl, cycloalkyl, heterocyclyl, aryl and heteroaryl groups are optionally substituted;

each occurrence of R$^6$ is independently selected from the group consisting of H, C$_1$-C$_6$ alkyl, C$_1$-C$_6$ heteroalkyl, C$_2$-C$_6$ alkenyl, 2-cyanovinyl, and —C$_1$-C$_3$ alkyl-(C$_3$-C$_6$ alkenyl), wherein the alkyl, heteroalkyl, or alkenyl groups are optionally substituted;

X$^1$ is CR$^3$ or N;

X$^2$, X$^3$ and X$^4$ are each independently selected from the group consisting of —O—, —C(R$^3$)$_2$—, —S— and —NR$^4$—;

L is —(CH$_2$)$_y$—, wherein one or more —CH$_2$— groups in L are independently and optionally replaced with —O—, —S— or —NR$^4$—,
with the provisos that: no heteroatom-heteroatom bond exist within L, and L is not covalently linked to X$^4$ or M through a heteroatom-heteroatom bond;

M is —OR$^5$, —SR$^5$, —N(R$^5$)$_2$—, aryl or heterocyclyl, wherein the aryl or heterocyclyl are independently optionally substituted,
with the proviso that if X$^1$ is CR$^3$, and R$^3$ is H or (C$_1$-C$_4$)alkyl, then X$^4$ is —O— or —S—, y is an integer from 2-19, and L contains at least one heteroatom;

m and n are each independently an integer from 0-5; and,
y is an integer from 0-19,
a salt, solvate, or N-oxide thereof.

In another embodiment, L is selected from the group consisting of —(CH$_2$)$_2$—, —(CH$_2$)$_3$—, —(CH$_2$)$_2$(OCH$_2$CH$_2$)—, —(CH$_2$)$_2$(OCH$_2$CH$_2$)$_2$—, —(CH$_2$)$_2$(OCH$_2$CH$_2$)$_3$—, and —(CH$_2$)$_2$(OCH$_2$CH$_2$)$_5$—.

In another embodiment, L is —(CH$_2$)$_3$—.

In another embodiment, M is monocyclic heterocyclyl.

In another embodiment, M is selected from the group consisting of morpholin-4-yl, imidazol-1-yl, piperidin-1-yl, piperidin-4-yl, tetrahydropyranyl, piperizin-1-yl or 4-methyl-piperizin-1-yl.

In another embodiment, the at least one compound of formula (I) is a compound of formula (II):

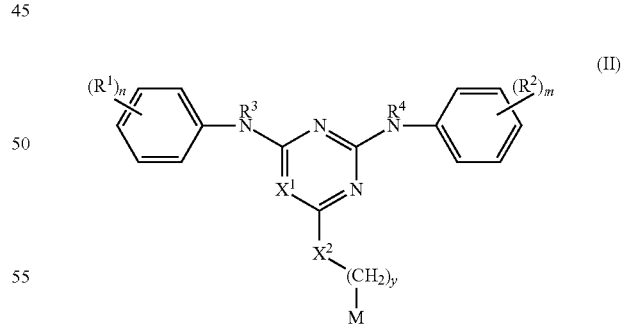

(II)

wherein in formula (II):
each occurrence of R$^1$ and R$^2$ is independently selected from the group consisting of H, —C$_1$-C$_6$ alkyl, —C$_1$-C$_6$ cycloalkyl, —C$_1$-C$_6$ alkenyl, —C$_1$-C$_6$ fluoroalkyl, —C$_1$-C$_6$ heteroalkyl, —F, —Cl, —Br, —I, —CN, —NO$_2$, —R$^6$, —OR$^6$, —SR$^6$, —S(=O)R$^6$, —S(=O)$_2$R$^6$, —NHS(=O)$_2$R$^6$, —C(=O)R$^6$, —OC(=O)R$^6$, —CO$_2$R$^6$, —OCO$_2$R$^6$, —CH(R$^6$)$_2$, —N(R$^6$)$_2$, —C(=O)N(R$^6$)$_2$, —OC(=O)N(R$^6$)$_2$, —NHC(=O)NH(R$^6$), —NHC(=O)R$^6$, —NHC(=O)OR⁶, —C(OH)(R⁶)₂, and —C(NH₂)(R⁶)₂, wherein the alkyl, cycloalkyl, and alkenyl groups are optionally substituted;

R³, R⁴, and R⁵ are each independently selected from the group consisting of hydrogen and $C_1$-$C_6$ alkyl;

each occurrence of R⁶ is independently selected from the group consisting of H, $C_1$-$C_6$ alkyl, $C_1$-$C_6$ heteroalkyl, $C_2$-$C_6$ alkenyl, 2-cyanovinyl, and —$C_1$-$C_3$ alkyl-($C_3$-$C_6$ alkenyl), wherein the alkyl, heteroalkyl, or alkenyl groups are optionally substituted;

X¹ is CH or N;

X² is selected from the group consisting of —O—, —S— and —NH—;

M is heterocyclyl, wherein the heterocyclyl is optionally substituted;

m and n are each independently an integer from 0-5; and, y is an integer from 1-5, a salt, solvate, or N-oxide thereof.

In another embodiment, the at least one compound of formula (I) is a compound of formula (IIa):

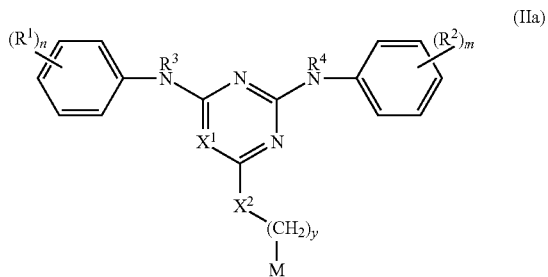

(IIa)

wherein in formula (IIa):

each occurrence of R¹ and R² is independently selected from the group consisting of H, —$C_1$-$C_6$ alkyl, —$C_1$-$C_6$ cycloalkyl, —$C_1$-$C_6$ alkenyl, —$C_1$-$C_6$ fluoroalkyl, —$C_1$-$C_6$ heteroalkyl, —F, —Cl, —Br, —I, —CN, —NO₂, —R⁶, —OR⁶, —SR⁶, —S(=O)R⁶, —S(=O)₂R⁶, —NHS(=O)₂R⁶, —C(=O)R⁶, —OC(=O)R⁶, —CO₂R⁶, —OCO₂R⁶, —CH(R⁶)₂, —N(R⁶)₂, —C(=O)N(R⁶)₂, —OC(=O)N(R⁶)₂, —NHC(=O)NH(R⁶), —NHC(=O)R⁶, —NHC(=O)OR⁶, —C(OH)(R⁶)₂, and —C(NH₂)(R⁶)₂, wherein the alkyl, cycloalkyl, and alkenyl groups are optionally substituted;

R³, R⁴, and R⁵ are each independently selected from the group consisting of hydrogen and $C_1$-$C_6$ alkyl;

each occurrence of R⁶ is independently selected from the group consisting of H, $C_1$-$C_6$ alkyl, $C_1$-$C_6$ heteroalkyl, $C_2$-$C_6$ alkenyl, 2-cyanovinyl, and —$C_1$-$C_3$ alkyl-($C_3$-$C_6$ alkenyl), wherein the alkyl, heteroalkyl, or alkenyl groups are optionally substituted;

X¹ is CH or N;

X² is selected from the group consisting of —O—, —S— and —NH—;

M is heterocyclyl, wherein the heterocyclyl is optionally substituted, with the proviso that if X¹ is CH, then X² is —O— or —S—;

m and n are each independently an integer from 0-5; and, y is an integer from 1-5, a salt, solvate, or N-oxide thereof.

In another embodiment, the compound is at least one selected from the group consisting of 4-((4-(mesitylamino)-6-(2-morpholinoethoxy) pyrimidin-2-yl)amino)benzonitrile, 4-((4-(mesitylamino)-6-(3-morpholinopropoxy) pyrimidin-2-yl)amino)benzonitrile, 4-((4-(mesitylamino)-6-(2-morpholinoethoxy)-1,3,5-triazin-2-yl)amino)benzonitrile, 4-((4-(mesitylamino)-6-(3-morpholinopropoxy)-1,3,5-triazin-2-yl)amino)benzonitrile, 4-((4-((4-cyanophenyl)amino)-6-(3-morpholino propoxy)-1,3,5-triazin-2-yl)amino)-3,5-dimethylbenzonitrile, (E)-4-((4-((4-(2-cyanovinyl)-2,6-dimethylphenyl)amino)-6-(3-morpholinopropoxy)-1,3,5-triazin-2-yl)amino)benzonitrile, 4-((4-((2,6-difluoro-4-methylphenyl)amino)-6-(3-morpholino propoxy)-1,3,5-triazin-2-yl)amino)benzonitrile, 4-((4-((4-ethyl-2,6-difluorophenyl)amino)-6-(3-morpholinopropoxy)-1,3,5-triazin-2-yl)amino)benzonitrile, 4-((4-((2,6-difluoro-4-isopropylphenyl)amino)-6-(3-morpholinopropoxy)-1,3,5-triazin-2-yl)amino)benzonitrile, 4-((4-((4-cyclopropyl-2,6-difluorophenyl)amino)-6-(3-morpholinopropoxy)-1,3,5-triazin-2-yl)amino)benzonitrile, 4-((4-((4-(2-cyanoethyl)-2,6-difluorophenyl)amino)-6-(3-morpholinopropoxy)-1,3,5-triazin-2-yl)amino)benzonitrile, 4-((4-(mesitylamino)-6-(2-(piperidin-4-yl)ethoxy)-1,3,5-triazin-2-yl)amino) benzonitrile, 4-((4-(mesitylamino)-6-(3-(piperidin-4-yl) propoxy)-1,3,5-triazin-2-yl)amino)benzonitrile, (E)-4-((4-((4-(2-cyanovinyl)-2,6-difluorophenyl)amino)-6-(3-morpholinopropoxy)-1,3,5-triazin-2-yl)amino)benzonitrile, (E)-4-((4-((4-(2-cyanovinyl)-2,6-dimethylphenyl)amino)-6-((3-morpholinopropyl)amino)-1,3,5-triazin-2-yl)amino) benzonitrile, (E)-4-((4-((4-(2-cyanovinyl)-2,6-difluorophenyl)amino)-6-((3-morpholinopropyl)amino)-1,3,5-triazin-2-yl)amino)benzonitrile, (E)-4-((4-((4-(2-cyanovinyl)-2,6-dimethylphenyl)amino)-6-(3-morpholinopropoxy) pyrimidin-2-yl)amino)benzonitrile, (E)-4-((4-((4-(2-cyanovinyl)-2,6-difluorophenyl)amino)-6-(3-morpholinopropoxy)pyrimidin-2-yl)amino)benzonitrile, (E)-4-((4-((4-(2-cyanovinyl)-2,6-dimethylphenyl)amino)-6-((3-morpholinopropyl)amino)pyrimidin-2-yl)amino)benzonitrile, (E)-4-((4-((4-(2-cyanovinyl)-2,6-difluorophenyl)amino)-6-((3-morpholinopropyl)amino)pyrimidin-2-yl)amino)benzonitrile, and a salt thereof.

The compositions of the present invention may include certain embodiments. In one embodiment, the composition further comprises at least one pharmaceutically acceptable carrier. In another embodiment, the composition further comprises at least one additional therapeutic agent. In another embodiment, the at least one additional therapeutic is at least one selected from the group consisting of nevirapine, delavirdine, efavirenz, etravirine, rilpivirine, and a salt thereof.

The present invention also includes a method of preventing or treating an HIV-1 infection in a subject in need thereof, the method comprising administering to the subject a therapeutically effective amount of a pharmaceutical composition comprising at least one compound of formula (I):

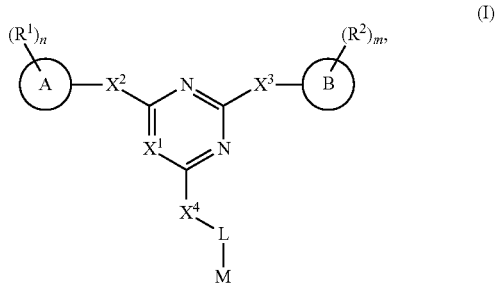

(I)

wherein in (I):

ring A and ring B are each independently aryl or heterocyclic;

each occurrence of $R^1$, $R^2$ and $R^3$ is independently selected from the group consisting of H, $-C_1-C_6$ alkyl, $-C_1-C_6$ cycloalkyl, $-C_1-C_6$ alkenyl, $-C_1-C_6$ fluoroalkyl, $-C_1-C_6$ heteroalkyl, $-F$, $-Cl$, $-Br$, $-I$, $-CN$, $-NO_2$, $-R^6$, $-OR^6$, $-SR^6$, $-S(=O)R^6$, $-S(=O)_2R^6$, $-NHS(=O)_2R^6$, $-C(=O)R^6$, $-OC(=O)R^6$, $-CO_2R^6$, $-OCO_2R^6$, $-CH(R^6)_2$, $-N(R^6)_2$, $-C(=O)N(R^6)_2$, $-OC(=O)N(R^6)_2$, $-NHC(=O)NH(R^6)$, $-NHC(=O)R^6$, $-NHC(=O)OR^6$, $-C(OH)(R^6)_2$, and $-C(NH_2)(R^6)_2$, wherein the alkyl, cycloalkyl, and alkenyl groups are optionally substituted;

each occurrence of $R^4$ and $R^5$ is each independently selected from the group consisting of H, $C_1-C_6$ alkyl, $C_1-C_6$ heteroalkyl, $C_3-C_{10}$ cycloalkyl, $-C_1-C_3$ alkyl-($C_3-C_6$ cycloalkyl), ($C_4-C_{10}$)heterocyclyl, $-C_1-C_3$ alkyl-($C_4-C_{10}$ heterocyclyl), ($C_6-C_{10}$)aryl, $-C_1-C_3$ alkyl-($C_6-C_{10}$ aryl), ($C_5-C_{10}$)heteroaryl, and $-C_1-C_3$ alkyl-($C_5-C_{10}$ heteroaryl), wherein the alkyl, heteroalkyl, cycloalkyl, heterocyclyl, aryl and heteroaryl groups are optionally substituted;

each occurrence of $R^6$ is independently selected from the group consisting of H, $C_1-C_6$ alkyl, $C_1-C_6$ heteroalkyl, $C_2-C_6$ alkenyl, 2-cyanovinyl, and $-C_1-C_3$ alkyl-($C_3-C_6$ alkenyl), wherein the alkyl, heteroalkyl, or alkenyl groups are optionally substituted;

$X^1$ is $CR^3$ or N;

$X^2$, $X^3$ and $X^4$ are each independently selected from the group consisting of $-O-$, $-C(R^3)_2-$, $-S-$ and $-NR^4-$;

L is $-(CH_2)_y-$, wherein one or more $-CH_2-$ groups in L are independently and optionally replaced with $-O-$, $-S-$ or $-NR^4-$, with the provisos that: no heteroatom-heteroatom bond exist within L, and L is not covalently linked to $X^4$ or M through a heteroatom-heteroatom bond;

M is $-OR^5$, $-SR^5$, $-N(R^5)_2-$, aryl or heterocyclyl, wherein the aryl or heterocyclyl are independently optionally substituted;

m and n are each independently an integer from 0-5; and, y is an integer from 0-19, a salt, solvate, or N-oxide thereof.

In one embodiment, the at least one compound of formula (I) is a compound of formula (Ia):

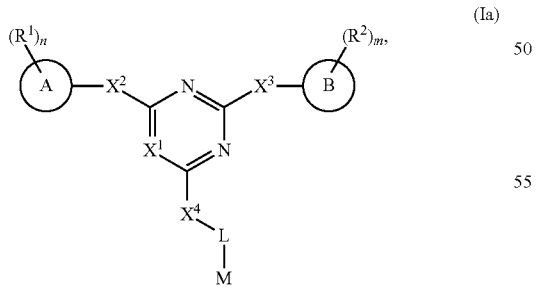

(Ia)

wherein in (Ia):

ring A and ring B are each independently aryl or heterocyclic;

each occurrence of $R^1$, $R^2$ and $R^3$ is independently selected from the group consisting of H, $-C_1-C_6$ alkyl, $-C_1-C_6$ cycloalkyl, $-C_1-C_6$ alkenyl, $-C_1-C_6$ fluoroalkyl, $-C_1-C_6$ heteroalkyl, $-F$, $-Cl$, $-Br$, $-I$, $-CN$, $-NO_2$, $-R^6$, $-OR^6$, $-SR^6$, $-S(=O)R^6$, $-S(=O)_2R^6$, $-NHS(=O)_2R^6$, $-C(=O)R^6$, $-OC(=O)R^6$, $-CO_2R^6$, $-OCO_2R^6$, $-CH(R^6)_2$, $-N(R^6)_2$, $-C(=O)N(R^6)_2$, $-OC(=O)N(R^6)_2$, $-NHC(=O)NH(R^6)$, $-NHC(=O)R^6$, $-NHC(=O)OR^6$, $-C(OH)(R^6)_2$, and $-C(NH_2)(R^6)_2$, wherein the alkyl, cycloalkyl, and alkenyl groups are optionally substituted;

each occurrence of $R^4$ and $R^5$ is each independently selected from the group consisting of H, $C_1-C_6$ alkyl, $C_1-C_6$ heteroalkyl, $C_3-C_{10}$ cycloalkyl, $-C_1-C_3$ alkyl-($C_3-C_6$ cycloalkyl), ($C_4-C_{10}$)heterocyclyl, $-C_1-C_3$ alkyl-($C_4-C_{10}$ heterocyclyl), ($C_6-C_{10}$)aryl, $-C_1-C_3$ alkyl-($C_6-C_{10}$ aryl), ($C_5-C_{10}$)heteroaryl, and $-C_1-C_3$ alkyl-($C_5-C_{10}$ heteroaryl), wherein the alkyl, heteroalkyl, cycloalkyl, heterocyclyl, aryl and heteroaryl groups are optionally substituted;

each occurrence of $R^6$ is independently selected from the group consisting of H, $C_1-C_6$ alkyl, $C_1-C_6$ heteroalkyl, $C_2-C_6$ alkenyl, 2-cyanovinyl, and $-C_1-C_3$ alkyl-($C_3-C_6$ alkenyl), wherein the alkyl, heteroalkyl, or alkenyl groups are optionally substituted;

$X^1$ is $CR^3$ or N;

$X^2$, $X^3$ and $X^4$ are each independently selected from the group consisting of $-O-$, $-C(R^3)_2-$, $-S-$ and $-NR^4-$;

L is $-(CH_2)_y-$, wherein one or more $-CH_2-$ groups in L are independently and optionally replaced with $-O-$, $-S-$ or $-NR^4-$, with the provisos that: no heteroatom-heteroatom bond exist within L, and L is not covalently linked to $X^4$ or M through a heteroatom-heteroatom bond;

M is $-OR^5$, $-SR^5$, $-N(R^5)_2-$, aryl or heterocyclyl, wherein the aryl or heterocyclyl are independently optionally substituted, with the proviso that if $X^1$ is $CR^3$, and $R^3$ is H or $(C_1-C_4)$alkyl, then $X^4$ is $-O-$ or $-S-$, y is an integer from 2-19, and L contains at least one heteroatom;

m and n are each independently an integer from 0-5; and, y is an integer from 0-19, a salt, solvate, or N-oxide thereof.

In another embodiment, the at least one compound of formula (I) is a compound of formula (II):

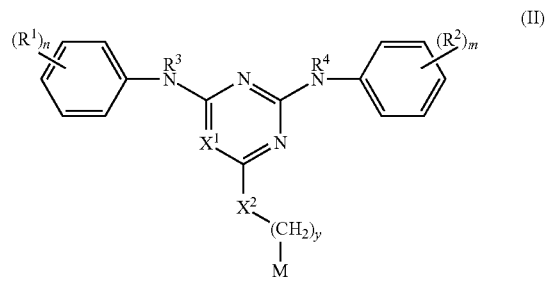

(II)

wherein in formula (II):

each occurrence of $R^1$ and $R^2$ is independently selected from the group consisting of H, $-C_1-C_6$ alkyl, $-C_1-C_6$ cycloalkyl, $-C_1-C_6$ alkenyl, $-C_1-C_6$ fluoroalkyl, $-C_1-C_6$ heteroalkyl, $-F$, $-Cl$, $-Br$, $-I$, $-CN$, $-NO_2$, $-R^6$, $-OR^6$, $-SR^6$, $-S(=O)R^6$, $-S(=O)_2R^6$, $-NHS(=O)_2R^6$, $-C(=O)R^6$, $-OC(=O)R^6$, $-CO_2R^6$, $-OCO_2R^6$, $-CH(R^6)_2$, $-N(R^6)_2$, $-C(=O)N(R^6)_2$, $-OC(=O)N(R^6)_2$, $-NHC(=O)NH(R^6)$, $-NHC(=O)R^6$, $-NHC(=O)OR^6$, $-C(OH)(R^6)_2$, and $-C(NH_2)(R^6)_2$, wherein the alkyl, cycloalkyl, and alkenyl groups are optionally substituted;

R³, R⁴, and R⁵ are each independently selected from the group consisting of hydrogen and C₁-C₆ alkyl;

each occurrence of R⁶ is independently selected from the group consisting of H, C₁-C₆ alkyl, C₁-C₆ heteroalkyl, C₂-C₆ alkenyl, 2-cyanovinyl, and —C₁-C₃ alkyl-(C₃-C₆ alkenyl), wherein the alkyl, heteroalkyl, or alkenyl groups are optionally substituted;

X¹ is CH or N;

X² is selected from the group consisting of —O—, —S— and —NH—;

M is heterocyclyl, wherein the heterocyclyl is optionally substituted;

m and n are each independently an integer from 0-5; and, y is an integer from 1-5, a salt, solvate, or N-oxide thereof.

In another embodiment, the at least one compound of formula (I) is a compound of formula (IIa):

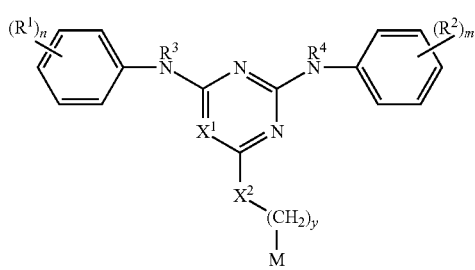

(IIa)

wherein in formula (IIa):

each occurrence of R¹ and R² is independently selected from the group consisting of H, —C₁-C₆ alkyl, —C₁-C₆ cycloalkyl, —C₁-C₆ alkenyl, —C₁-C₆ fluoroalkyl, —C₁-C₆ heteroalkyl, —F, —Cl, —Br, —I, —CN, —NO₂, —R⁶, —OR⁶, —SR⁶, —S(=O)R⁶, —S(=O)₂R⁶, —NHS(=O)₂R⁶, —C(=O)R⁶, —OC(=O)R⁶, —CO₂R⁶, —OCO₂R⁶, —CH(R⁶)₂, —N(R⁶)₂, —C(=O)N(R⁶)₂, —OC(=O)N(R⁶)₂, —NHC(=O)NH(R⁶), —NHC(=O)R⁶, —NHC(=O)OR⁶, —C(OH)(R⁶)₂, and —C(NH₂)(R⁶)₂, wherein the alkyl, cycloalkyl, and alkenyl groups are optionally substituted;

R³, R⁴, and R⁵ are each independently selected from the group consisting of hydrogen and C₁-C₆ alkyl;

each occurrence of R⁶ is independently selected from the group consisting of H, C₁-C₆ alkyl, C₁-C₆ heteroalkyl, C₂-C₆ alkenyl, 2-cyanovinyl, and —C₁-C₃ alkyl-(C₃-C₆ alkenyl), wherein the alkyl, heteroalkyl, or alkenyl groups are optionally substituted;

X¹ is CH or N;

X² is selected from the group consisting of —O—, —S— and —NH—;

M is heterocyclyl, wherein the heterocyclyl is optionally substituted, with the proviso that if X¹ is CH, then X² is —O— or —S—;

m and n are each independently an integer from 0-5; and, y is an integer from 1-5, a salt, solvate, or N-oxide thereof.

In another embodiment, M is selected from the group consisting of morpholin-4-yl, imidazol-1-yl, piperidin-1-yl, piperidin-4-yl, tetrahydropyranyl, piperizin-1-yl or 4-methyl-piperizin-1-yl.

In another embodiment, the compound is at least one selected from the group consisting of 4-((4-(mesitylamino)-6-(2-morpholinoethoxy) pyrimidin-2-yl)amino)benzonitrile, 4-((4-(mesitylamino)-6-(3-morpholinopropoxy) pyrimidin-2-yl)amino)benzonitrile, 4-((4-(mesitylamino)-6-(2-morpholinoethoxy)-1,3,5-triazin-2-yl)amino)benzonitrile, 4-((4-(mesitylamino)-6-(3-morpholinopropoxy)-1,3,5-triazin-2-yl)amino)benzonitrile, 4-((4-((4-cyanophenyl)amino)-6-(3-morpholino propoxy)-1,3,5-triazin-2-yl)amino)-3,5-dimethylbenzonitrile, (E)-4-((4-((4-(2-cyanovinyl)-2,6-dimethylphenyl)amino)-6-(3-morpholinopropoxy)-1,3,5-triazin-2-yl)amino)benzonitrile, 4-((4-((2,6-difluoro-4-methylphenyl)amino)-6-(3-morpholino propoxy)-1,3,5-triazin-2-yl)amino)benzonitrile, 4-((4-((4-ethyl-2,6-difluorophenyl)amino)-6-(3-morpholinopropoxy)-1,3,5-triazin-2-yl)amino)benzonitrile, 4-((4-((2,6-difluoro-4-isopropylphenyl)amino)-6-(3-morpholinopropoxy)-1,3,5-triazin-2-yl)amino)benzonitrile, 4-((4-((4-cyclopropyl-2,6-difluorophenyl)amino)-6-(3-morpholinopropoxy)-1,3,5-triazin-2-yl)amino)benzonitrile, 4-((4-((4-(2-cyanoethyl)-2,6-difluorophenyl)amino)-6-(3-morpholinopropoxy)-1,3,5-triazin-2-yl)amino)benzonitrile, 4-((4-(mesitylamino)-6-(2-(piperidin-4-yl)ethoxy)-1,3,5-triazin-2-yl)amino) benzonitrile, 4-((4-(mesitylamino)-6-(3-(piperidin-4-yl)propoxy)-1,3,5-triazin-2-yl)amino)benzonitrile, (E)-4-((4-((4-(2-cyanovinyl)-2,6-difluorophenyl)amino)-6-(3-morpholinopropoxy)-1,3,5-triazin-2-yl)amino)benzonitrile, (E)-4-((4-((4-(2-cyanovinyl)-2,6-dimethylphenyl)amino)-6-((3-morpholinopropyl)amino)-1,3,5-triazin-2-yl)amino) benzonitrile, (E)-4-((4-((4-(2-cyanovinyl)-2,6-difluorophenyl)amino)-6-((3-morpholinopropyl)amino)-1,3,5-triazin-2-yl)amino)benzonitrile, (E)-4-((4-((4-(2-cyanovinyl)-2,6-dimethylphenyl)amino)-6-(3-morpholinopropoxy) pyrimidin-2-yl)amino)benzonitrile, (E)-4-((4-((4-(2-cyanovinyl)-2,6-difluorophenyl)amino)-6-(3-morpholinopropoxy)pyrimidin-2-yl)amino)benzonitrile, (E)-4-((4-((4-(2-cyanovinyl)-2,6-dimethylphenyl)amino)-6-((3-morpholinopropyl)amino)pyrimidin-2-yl)amino)benzonitrile, (E)-4-((4-((4-(2-cyanovinyl)-2,6-difluorophenyl)amino)-6-((3-morpholinopropyl)amino)pyrimidin-2-yl)amino)benzonitrile, and a salt thereof.

The methods of the present invention may include certain embodiments. In one embodiment, the method further comprises administering to the subject at least one additional therapeutic agent. In another embodiment, the at least one additional therapeutic is selected from the group consisting of nevirapine, delavirdine, efavirenz, etravirine and rilpivirine. In another embodiment, the pharmaceutical composition and the at least one additional therapeutic agent are co-administered to the subject. In another embodiment, the pharmaceutical composition and the at least one additional therapeutic agent are co-formulated. In another embodiment, the HIV infection in the subject is resistant to at least one therapeutic agent selected from the group consisting of nevirapine, delavirdine, efavirenz, etravirine and rilpivirine. In another embodiment, the subject is human.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION OF THE INVENTION

Figure 1:
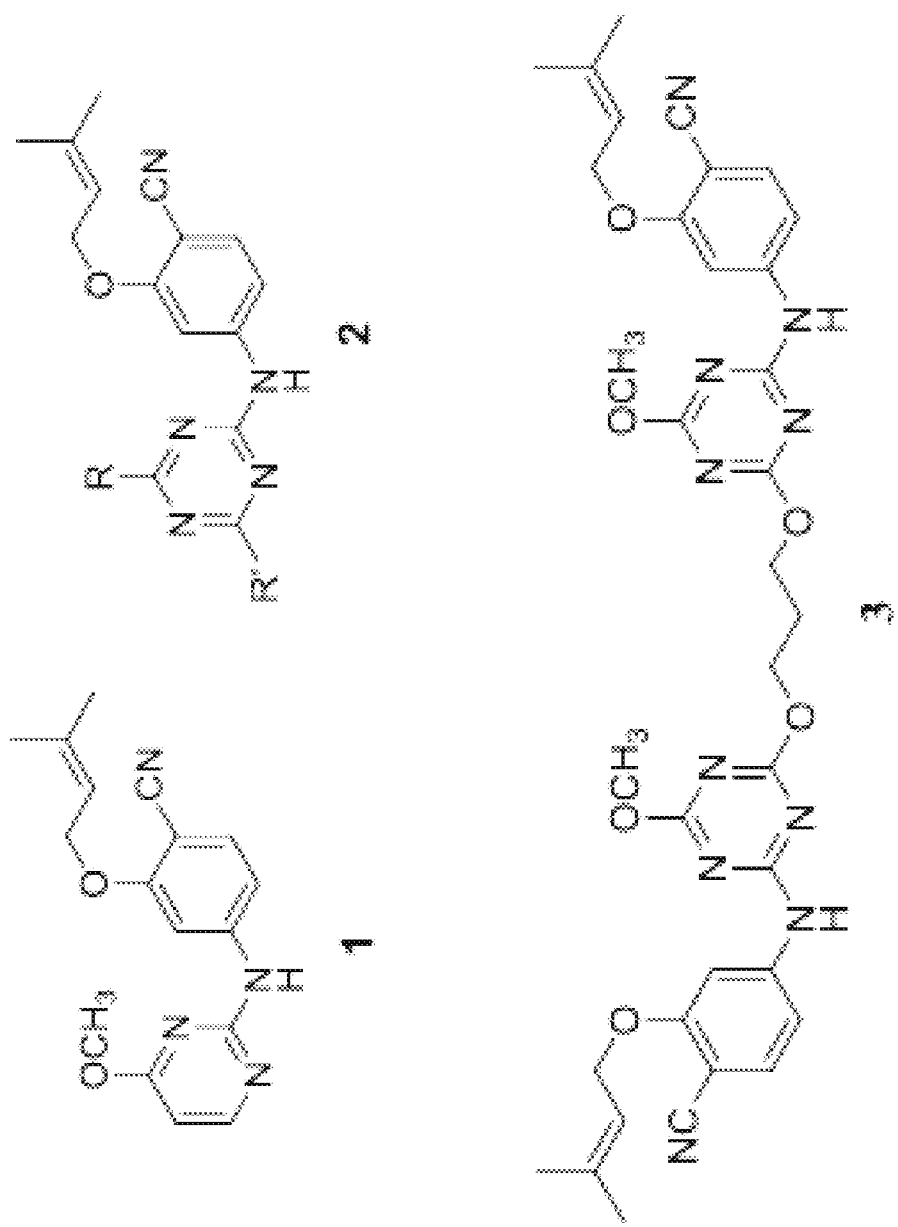
FIG. 1 illustrates the structures of reference compounds 1-3.

The present invention relates to the unexpected discovery of novel compounds with enhanced aqueous solubility and high anti-HIV-1 activity. In one embodiment, the compounds of the present invention inhibit the activity of HIV-1 reverse transcriptase. In another embodiment, the compounds of the invention are used to treat HIV-1 infection in a subject in need thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein.

Such treatments may be specifically tailored or modified, based on knowledge obtained from the field of pharmacogenomics.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

An "effective amount" of a delivery vehicle is that amount sufficient to effectively bind or deliver a compound.

As used herein, the term "potency" refers to the dose needed to produce half the maximal response ($ED_{50}$).

As used herein, the term "efficacy" refers to the maximal effect ($E_{max}$) achieved within an assay.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—SS—$CH_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are $(C_1-C_3)$ alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

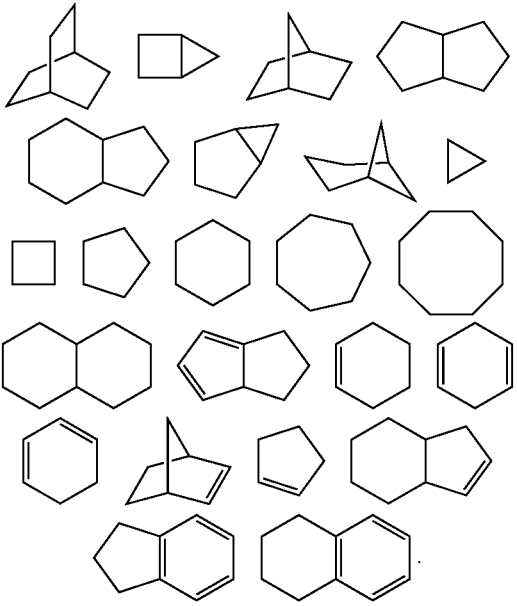

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbomane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

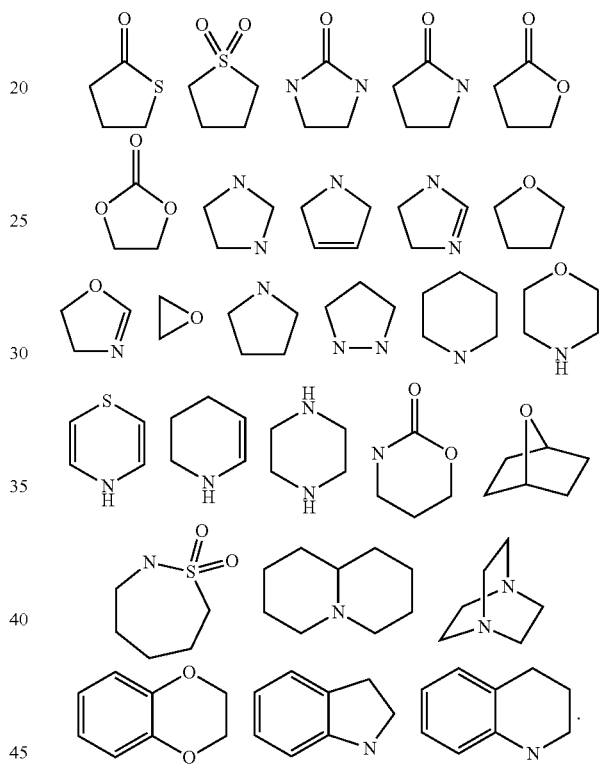

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$) alkyl" means a heteroaryl-($C_1$-$C_3$)alkyl functional group in which the heteroaryl group is substituted. Preferred is substituted heteroaryl-($CH_2$)—.

As used herein, the term "heteroaryl" or "heteroaromatic" refers to a heterocycle having aromatic character. A polycyclic heteroaryl may include one or more rings that are partially saturated. Examples include the following moieties:

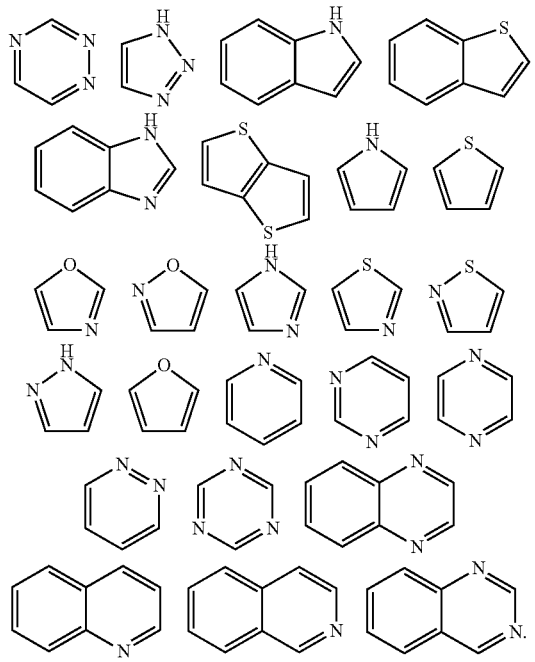

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —$NH_2$, —OH, —$NH(CH_3)$, —$N(CH_3)_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C($NH_2$)[substituted or unsubstituted alkyl]$_2$. In another embodiment, by way of example, an optional substituent is selected from oxo, fluorine, chlorine, bromine, iodine, —CN, —$NH_2$, —OH, —$NH(CH_3)$, —$N(CH_3)_2$, —$CH_3$, —$CH_2CH_3$, —$CH(CH_3)_2$, —$CF_3$, —$CH_2CF_3$, —$OCH_3$, —$OCH_2CH_3$, —$OCH(CH_3)_2$, —$OCF_3$, —$OCH_2CF_3$, —S(=O)$_2$—$CH_3$, —C(=O)$NH_2$, —C(=O)—$NHCH_3$, —NHC(=O)$NHCH_3$, —C(=O)$CH_3$, and —C(=O)OH. In yet one embodiment, the substituents are independently selected from the group consisting of $C_{1-6}$ alkyl, —OH, $C_{1-6}$ alkoxy, halo, amino, acetamido, oxo and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the unexpected discovery of novel compounds with enhanced aqueous solubility and high anti-HIV-1 activity. In one embodiment, the compounds of the present invention inhibit the activity of HIV-1 reverse transcriptase. In another embodiment, the compounds of the invention are used to treat HIV-1 infection in a subject in need thereof.

The present invention relates to novel non-nucleoside inhibitors of HIV-1 reverse transcriptase (NNRTIs). NNRTIs are a central component of highly active antiretroviral therapy (HAART) in spite of significant deficiencies in the currently approved drugs in this class. Current drugs in the NNRTI class suffer from poor solubility, which leads to problems with formulation and administration. Thus, in one aspect, the present invention provides novel NNRTIs that have greatly enhanced solubility over the structurally related drugs etravirine and rilpivirine, while retaining high antiviral activity. In one embodiment, solubility enhancements are derived at least in part from strategic placement of a morpholinoalkoxy substituent or another polar substituent in the entrance channel of the NNRTI binding site.

Compounds

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I), or a salt, solvate, or N-oxide thereof:

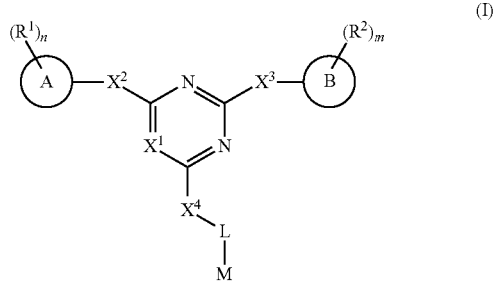

(I)

wherein in formula (I):

ring A and ring B are each independently aryl or heterocyclic;

each occurrence of $R^1$, $R^2$ and $R^3$ is independently selected from the group consisting of H, —$C_1$-$C_6$ alkyl, —$C_1$-$C_6$ cycloalkyl, —$C_1$-$C_6$ alkenyl, —$C_1$-$C_6$ fluoroalkyl, —$C_1$-$C_6$ heteroalkyl, —F, —Cl, —Br, —I, —CN, —$NO_2$, —$R^6$, —$OR^6$, —$SR^6$, —S(=O)$R^6$, —S(=O)$_2R^6$, —NHS(=O)$_2R^6$, —C(=O)$R^6$, —OC(=O)$R^6$, —$CO_2R^6$, —$OCO_2R^6$, —CH($R^6$)$_2$, —N($R^6$)$_2$, —C(=O)N($R^6$)$_2$, —OC(=O)N($R^6$)$_2$, —NHC(=O)NH($R^6$), —NHC(=O)$R^6$, —NHC(=O)O$R^6$, —C(OH)($R^6$)$_2$, and —C($NH_2$)($R^6$)$_2$, wherein the alkyl, cycloalkyl, and alkenyl groups are optionally substituted;

each occurrence of $R^4$ and $R^5$ is each independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), ($C_4$-$C_{10}$)heterocyclyl, —$C_1$-$C_3$ alkyl-($C_4$-$C_{10}$ heterocyclyl), ($C_6$-$C_{10}$)aryl, —$C_1$-$C_3$ alkyl-($C_6$-$C_{10}$ aryl), ($C_5$-$C_{10}$)heteroaryl, and —$C_1$-$C_3$ alkyl-($C_5$-$C_{10}$ heteroaryl), wherein the alkyl, heteroalkyl, cycloalkyl, heterocyclyl, aryl and heteroaryl groups are optionally substituted;

each occurrence of $R^6$ is independently selected from the group consisting of H, $C_1$-$C_6$ alkyl, $C_1$-$C_6$ heteroalkyl, $C_2$-$C_6$ alkenyl, 2-cyanovinyl, and —$C_1$-$C_3$ alkyl-($C_3$-$C_6$ alkenyl), wherein the alkyl, heteroalkyl, or alkenyl groups are optionally substituted;

$X^1$ is $CR^3$ or N;

$X^2$, $X^3$ and $X^4$ are each independently selected from the group consisting of —O—, —C($R^3$)$_2$—, —S— and —$NR^4$—;

L is —($CH_2$)$_y$—, wherein one or more —$CH_2$— groups in L are independently and optionally replaced with —O—, —S— or —$NR^4$—, with the provisos that: no heteroatom-heteroatom bond exist within L, and L is not covalently linked to $X^4$ or M through a heteroatom-heteroatom bond;

M is —$OR^5$, —$SR^5$, —N($R^5$)$_2$—, aryl or heterocyclyl, wherein the aryl or heterocyclyl are independently optionally substituted, m and n are each independently an integer from 0-5; and,
y is an integer from 0-19.

In another aspect, the compound of the invention is a compound of formula (Ia), or a salt, solvate, or N-oxide thereof:

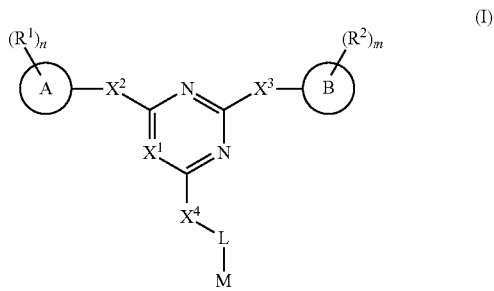

(I)

wherein in formula (Ia):

ring A and ring B are each independently aryl or heterocyclic;

each occurrence of $R^1$, $R^2$ and $R^3$ is independently selected from the group consisting of H, —$C_1$-$C_6$ alkyl, —$C_1$-$C_6$ cycloalkyl, —$C_1$-$C_6$ alkenyl, —$C_1$-$C_6$ fluoroalkyl, —$C_1$-$C_6$ heteroalkyl, —F, —Cl, —Br, —I, —CN, —$NO_2$, —$R^6$, —$OR^6$, —$SR^6$, —S(=O)$R^6$, —S(=O)$_2R^6$, —NHS(=O)$_2R^6$, —C(=O)$R^6$, —OC(=O)$R^6$, —$CO_2R^6$, —$OCO_2R^6$, —CH($R^6$)$_2$, —N($R^6$)$_2$, —C(=O)N($R^6$)$_2$, —OC(=O)N($R^6$)$_2$, —NHC(=O)NH($R^6$), —NHC(=O)$R^6$, —NHC(=O)O$R^6$, —C(OH)($R^6$)$_2$, and —C($NH_2$)($R^6$)$_2$, wherein the alkyl, cycloalkyl, and alkenyl groups are optionally substituted;

each occurrence of $R^4$ and $R^5$ is each independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), ($C_4$-$C_{10}$)heterocyclyl, —$C_1$-$C_3$ alkyl-($C_4$-$C_{10}$ heterocyclyl), ($C_6$-$C_{10}$)aryl, —$C_1$-$C_3$ alkyl-($C_6$-$C_{10}$ aryl), ($C_5$-$C_{10}$)heteroaryl, and —$C_1$-$C_3$ alkyl-($C_5$-$C_{10}$ heteroaryl), wherein the alkyl, heteroalkyl, cycloalkyl, heterocyclyl, aryl and heteroaryl groups are optionally substituted;

each occurrence of $R^6$ is independently selected from the group consisting of H, $C_1$-$C_6$ alkyl, $C_1$-$C_6$ heteroalkyl, $C_2$-$C_6$ alkenyl, 2-cyanovinyl, and —$C_1$-$C_3$ alkyl-($C_3$-$C_6$ alkenyl), wherein the alkyl, heteroalkyl, or alkenyl groups are optionally substituted;

$X^1$ is $CR^3$ or N;

$X^2$, $X^3$ and $X^4$ are each independently selected from the group consisting of —O—, —$C(R^3)_2$—, —S— and —$NR^4$—;

L is —$(CH_2)_y$—, wherein one or more —$CH_2$— groups in L are independently and optionally replaced with —O—, —S— or —$NR^4$—, with the provisos that: no heteroatom-heteroatom bond exist within L, and L is not covalently linked to $X^4$ or M through a heteroatom-heteroatom bond;

M is —$OR^5$, —$SR^5$, —$N(R^5)_2$—, aryl or heterocyclyl, wherein the aryl or heterocyclyl are independently optionally substituted, with the proviso that if $X^1$ is $CR^3$, and $R^3$ is H or ($C_1$-$C_4$)alkyl, then $X^4$ is —O— or —S—, y is an integer from 2-19, and L contains at least one heteroatom;

m and n are each independently an integer from 0-5; and, y is an integer from 0-19.

In one embodiment, ring A is aryl, and ring B is aryl.

In one embodiment, L is selected from the group consisting of —$(CH_2)_2$—, —$(CH_2)_3$—, —$(CH_2)_2(OCH_2CH_2)$—, —$(CH_2)_2(OCH_2CH_2)_2$—, —$(CH_2)_2(OCH_2CH_2)_3$—, and —$(CH_2)_2(OCH_2CH_2)_5$—. In another embodiment, L is —$(CH_2)_3$—.

In one embodiment, M is monocyclic heterocyclyl. In another embodiment, M is morpholin-4-yl. In yet another embodiment, M is imidazol-1-yl. In yet another embodiment, M is piperidin-1-yl. In yet another embodiment, M is piperidin-4-yl. In yet another embodiment, M is tetrahydropyranyl. In yet another embodiment, M is piperizin-1-yl. In yet another embodiment, M is 4-methyl-piperizin-1-yl.

In another aspect, the compound of the invention is a compound of formula (II), or a salt, solvate, or N-oxide thereof:

(II)

wherein in formula (II):

each occurrence of $R^1$ and $R^2$ is independently selected from the group consisting of H, —$C_1$-$C_6$ alkyl, —$C_1$-$C_6$ cycloalkyl, —$C_1$-$C_6$ alkenyl, —$C_1$-$C_6$ fluoroalkyl, —$C_1$-$C_6$ heteroalkyl, —F, —Cl, —Br, —I, —CN, —$NO_2$, —$R^6$, —$OR^6$, —$SR^6$, —$S(=O)R^6$, —$S(=O)_2R^6$, —$NHS(=O)_2R^6$, —$C(=O)R^6$, —$OC(=O)R^6$, —$CO_2R^6$, —$OCO_2R^6$, —$CH(R^6)_2$, —$N(R^6)_2$, —$C(=O)N(R^6)_2$, —$OC(=O)N(R^6)_2$, —$NHC(=O)NH(R^6)$, —$NHC(=O)R^6$, —$NHC(=O)OR^6$, —$C(OH)(R^6)_2$, and —$C(NH_2)(R^6)_2$, wherein the alkyl, cycloalkyl, and alkenyl groups are optionally substituted;

$R^3$, $R^4$, and $R^5$ are each independently selected from the group consisting of hydrogen and $C_1$-$C_6$ alkyl;

each occurrence of $R^6$ is independently selected from the group consisting of H, $C_1$-$C_6$ alkyl, $C_1$-$C_6$ heteroalkyl, $C_2$-$C_6$ alkenyl, 2-cyanovinyl, and —$C_1$-$C_3$ alkyl-($C_3$-$C_6$ alkenyl), wherein the alkyl, heteroalkyl, or alkenyl groups are optionally substituted;

$X^1$ is $CR^5$ or N;

$X^2$ is selected from the group consisting of —O—, —S— and —NH—;

M is heterocyclyl, wherein the heterocyclyl is optionally substituted, m and n are each independently an integer from 0-5; and, y is an integer from 1-5.

In another aspect, the compound of the invention is a compound of formula (IIa), or a salt, solvate, or N-oxide thereof:

(II)

wherein in formula (IIa):

each occurrence of $R^1$ and $R^2$ is independently selected from the group consisting of H, —$C_1$-$C_6$ alkyl, —$C_1$-$C_6$ cycloalkyl, —$C_1$-$C_6$ alkenyl, —$C_1$-$C_6$ fluoroalkyl, —$C_1$-$C_6$ heteroalkyl, —F, —Cl, —Br, —I, —CN, —$NO_2$, —$R^6$, —$OR^6$, —$SR^6$, —$S(=O)R^6$, —$S(=O)_2R^6$, —$NHS(=O)_2R^6$, —$C(=O)R^6$, —$OC(=O)R^6$, —$CO_2R^6$, —$OCO_2R^6$, —$CH(R^6)_2$, —$N(R^6)_2$, —$C(=O)N(R^6)_2$, —$OC(=O)N(R^6)_2$, —$NHC(=O)NH(R^6)$, —$NHC(=O)R^6$, —$NHC(=O)OR^6$, —$C(OH)(R^6)_2$, and —$C(NH_2)(R^6)_2$, wherein the alkyl, cycloalkyl, and alkenyl groups are optionally substituted;

$R^3$, $R^4$, and $R^5$ are each independently selected from the group consisting of hydrogen and $C_1$-$C_6$ alkyl;

each occurrence of $R^6$ is independently selected from the group consisting of H, $C_1$-$C_6$ alkyl, $C_1$-$C_6$ heteroalkyl, $C_2$-$C_6$ alkenyl, 2-cyanovinyl, and —$C_1$-$C_3$ alkyl-($C_3$-$C_6$ alkenyl), wherein the alkyl, heteroalkyl, or alkenyl groups are optionally substituted;

$X^1$ is $CR^5$ or N;

$X^2$ is selected from the group consisting of —O—, —S— and —NH—;

M is heterocyclyl, wherein the heterocyclyl is optionally substituted, with the proviso that if $X^1$ is CH, then $X^2$ is —O— or —S—;

m and n are each independently an integer from 0-5; and, y is an integer from 1-5.

In one embodiment, $X^1$ is CH and $X^2$ is —O—.

In one embodiment, $X^1$ is N, and $X^2$ is selected from the group consisting of —O— and —NH—.

In one embodiment, M is monocyclic heterocyclyl. In another embodiment, M is morpholin-4-yl. In yet another embodiment, M is imidazol-1-yl. In yet another embodiment, M is piperidin-1-yl. In yet another embodiment, M is piperidin-4-yl. In yet another embodiment, M is tetrahydropyranyl. In yet another embodiment, M is piperizin-1-yl. In yet another embodiment, M is 4-methyl-piperizin-1-yl.

In one embodiment, the compound of the invention is selected from the group consisting of:

4-((4-(mesitylamino)-6-(2-morpholinoethoxy)pyrimidin-2-yl)amino)benzonitrile,
4-((4-(mesitylamino)-6-(3-morpholinopropoxy)pyrimidin-2-yl)amino)benzonitrile,
4-((4-(mesitylamino)-6-(2-morpholinoethoxy)-1,3,5-triazin-2-yl)amino)benzonitrile,
4-((4-(mesitylamino)-6-(3-morpholinopropoxy)-1,3,5-triazin-2-yl)amino)benzonitrile,
4-((4-((4-cyanophenyl)amino)-6-(3-morpholinopropoxy)-1,3,5-triazin-2-yl)amino)-3,5-dimethylbenzonitrile,
(E)-4-((4-((4-(2-cyanovinyl)-2,6-dimethylphenyl)amino)-6-(3-morpholinopropoxy)-1,3,5-triazin-2-yl)amino)benzonitrile,
4-((4-((2,6-difluoro-4-methylphenyl)amino)-6-(3-morpholinopropoxy)-1,3,5-triazin-2-yl)amino)benzonitrile,
4-((4-((4-ethyl-2,6-difluorophenyl)amino)-6-(3-morpholinopropoxy)-1,3,5-triazin-2-yl)amino)benzonitrile,
4-((4-((2,6-difluoro-4-isopropylphenyl)amino)-6-(3-morpholinopropoxy)-1,3,5-triazin-2-yl)amino)benzonitrile,
4-((4-((4-cyclopropyl-2,6-difluorophenyl)amino)-6-(3-morpholinopropoxy)-1,3,5-triazin-2-yl)amino)benzonitrile,
4-((4-((4-(2-cyanoethyl)-2,6-difluorophenyl)amino)-6-(3-morpholinopropoxy)-1,3,5-triazin-2-yl)amino)benzonitrile,
4-((4-(mesitylamino)-6-(2-(piperidin-4-yl)ethoxy)-1,3,5-triazin-2-yl)amino benzonitrile,
4-((4-(mesitylamino)-6-(3-(piperidin-4-yl)propoxy)-1,3,5-triazin-2-yl)amino)benzonitrile,
(E)-4-((4-((4-(2-cyanovinyl)-2,6-difluorophenyl)amino)-6-(3-morpholinopropoxy)-1,3,5-triazin-2-yl)amino)benzonitrile,
(E)-4-((4-((4-(2-cyanovinyl)-2,6-dimethylphenyl)amino)-6-((3-morpholinopropyl)amino)-1,3,5-triazin-2-yl)amino)benzonitrile,
(E)-4-((4-((4-(2-cyanovinyl)-2,6-difluorophenyl)amino)-6-((3-morpholinopropyl)amino)-1,3,5-triazin-2-yl)amino)benzonitrile,
(E)-4-((4-((4-(2-cyanovinyl)-2,6-dimethylphenyl)amino)-6-(3-morpholinopropoxy)pyrimidin-2-yl)amino)benzonitrile,
(E)-4-((4-((4-(2-cyanovinyl)-2,6-difluorophenyl)amino)-6-(3-morpholinopropoxy)pyrimidin-2-yl)amino)benzonitrile,
(E)-4-((4-((4-(2-cyanovinyl)-2,6-dimethylphenyl)amino)-6-((3-morpholinopropyl)amino)pyrimidin-2-yl)amino)benzonitrile,
(E)-4-((4-((4-(2-cyanovinyl)-2,6-difluorophenyl)amino)-6-((3-morpholinopropyl)amino)pyrimidin-2-yl)amino)benzonitrile,
a salt thereof and any mixtures thereof.

In one embodiment, the compound of the invention is (E)-4-((4-((4-(2-cyanovinyl)-2,6-dimethylphenyl)amino)-6-(3-morpholinopropoxy)pyrimidin-2-yl)amino)benzonitrile or a salt thereof.

The invention also includes a pharmaceutical composition comprising at least one compound of the invention and at least one pharmaceutically acceptable carrier.

The structures and corresponding names of the compounds are illustrated in Table 1.

TABLE 1

| Compounds of the present invention | | |
|---|---|---|
| Structure | Name | Compound Name |
| 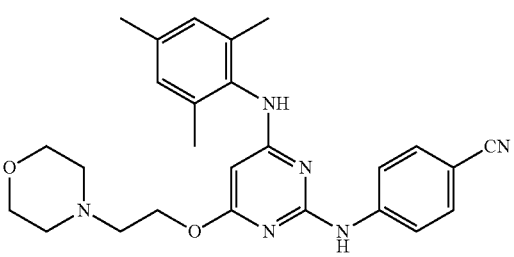 [SMILES: Cc1cc(C)c(Nc2cc(OCCN3CCOCC3)nc(Nc3ccc(C#N)cc3)n2)c(C)c1] | 4-((4-(mesitylamino)-6-(2-morpholinoethoxy)pyrimidin-2-yl)amino)benzonitrile | 5a |
| 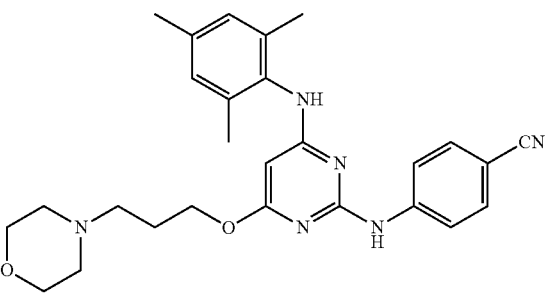 [SMILES: Cc1cc(C)c(Nc2cc(OCCCN3CCOCC3)nc(Nc3ccc(C#N)cc3)n2)c(C)c1] | 4-((4-(mesitylamino)-6-(3-morpholinopropoxy)pyrimidin-2-yl)amino)benzonitrile | 5b |

TABLE 1-continued

Compounds of the present invention

| Structure | Name | Compound Name |
|---|---|---|
| 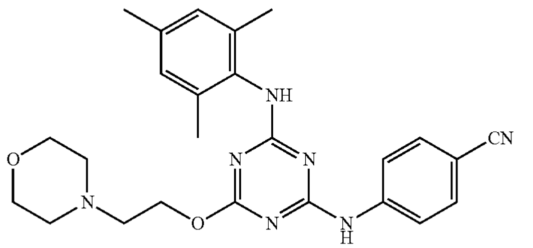 [SMILES: Cc1cc(C)c(Nc2nc(Nc3ccc(C#N)cc3)nc(OCCN3CCOCC3)n2)c(C)c1] | 4-((4-(mesitylamino)-6-(2-morpholinoethoxy)-1,3,5-triazin-2-yl)amino)benzonitrile | 6a |
| 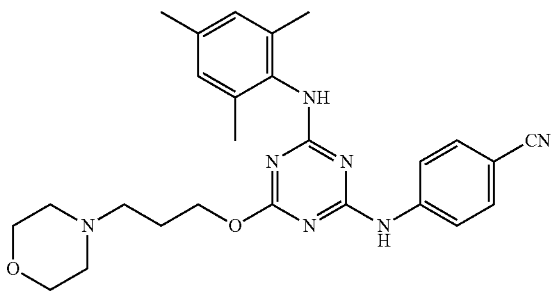 [SMILES: Cc1cc(C)c(Nc2nc(Nc3ccc(C#N)cc3)nc(OCCCN3CCOCC3)n2)c(C)c1] | 4-((4-(mesitylamino)-6-(3-morpholinopropoxy)-1,3,5-triazin-2-yl)amino)benzonitrile | 6b |
| 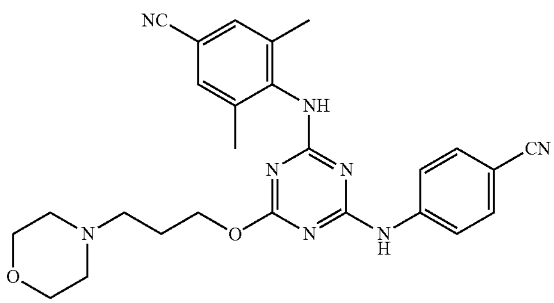 [SMILES: Cc1cc(C#N)cc(C)c1Nc1nc(Nc2ccc(C#N)cc2)nc(OCCCN2CCOCC2)n1] | 4-((4-((4-cyanophenyl)amino)-6-(3-morpholinopropoxy)-1,3,5-triazin-2-yl)amino)-3,5-dimethylbenzonitrile | 6c |
| 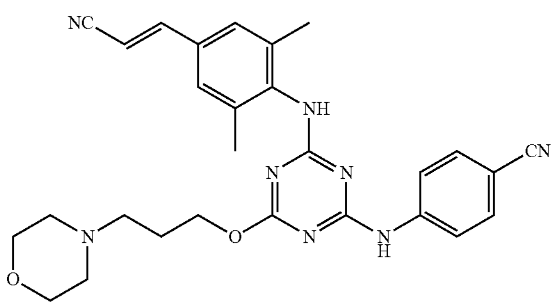 [SMILES: Cc1cc(/C=C/C#N)cc(C)c1Nc1nc(Nc2ccc(C#N)cc2)nc(OCCCN2CCOCC2)n1] | (E)-4-((4-((4-(2-cyanovinyl)-2,6-dimethylphenyl)amino)-6-(3-morpholinopropoxy)-1,3,5-triazin-2-yl)amino)benzonitrile | 6d |
| 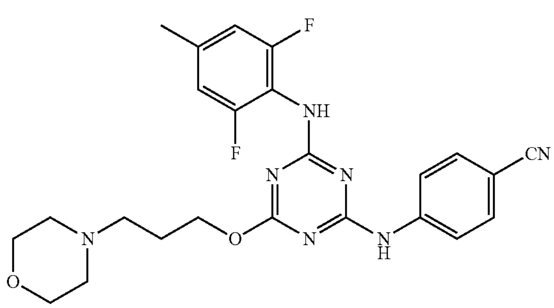 [SMILES: Cc1cc(F)c(Nc2nc(Nc3ccc(C#N)cc3)nc(OCCCN3CCOCC3)n2)c(F)c1] | 4-((4-((2,6-difluoro-4-methylphenyl)amino)-6-(3-morpholinopropoxy)-1,3,5-triazin-2-yl)amino)benzonitrile | 6e |

TABLE 1-continued

Compounds of the present invention

| Structure | Name | Compound Name |
|---|---|---|
| 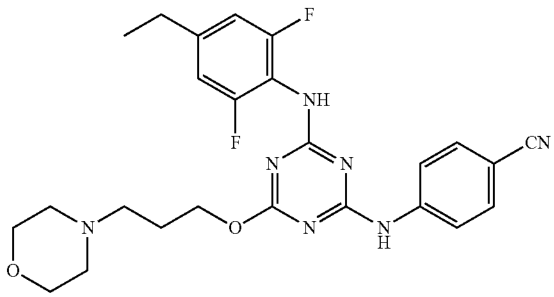 [SMILES: CCc1cc(F)c(Nc2nc(Nc3ccc(C#N)cc3)nc(OCCCN3CCOCC3)n2)c(F)c1] | 4-((4-((4-ethyl-2,6-difluorophenyl)amino)-6-(3-morpholinopropoxy)-1,3,5-triazin-2-yl)amino)benzonitrile | 6f |
| 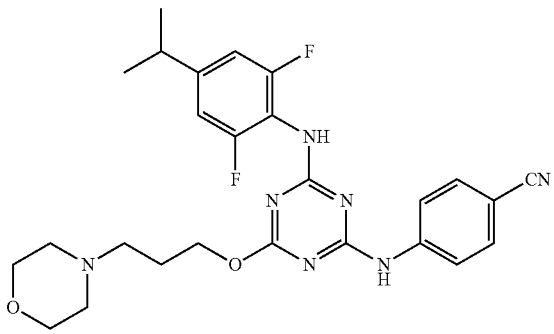 [SMILES: CC(C)c1cc(F)c(Nc2nc(Nc3ccc(C#N)cc3)nc(OCCCN3CCOCC3)n2)c(F)c1] | 4-((4-((2,6-difluoro-4-isopropylphenyl)amino)-6-(3-morpholinopropoxy)-1,3,5-triazin-2-yl)amino)benzonitrile | 6g |
| 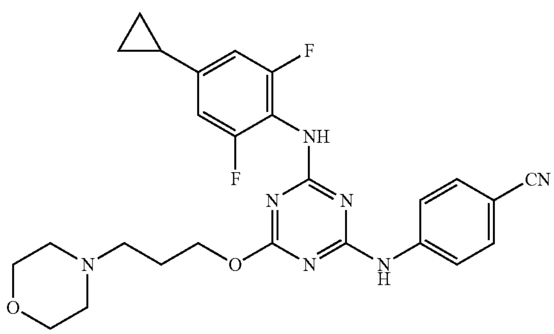 [SMILES: N#Cc1ccc(Nc2nc(Nc3c(F)cc(C4CC4)cc3F)nc(OCCCN3CCOCC3)n2)cc1] | 4-((4-((4-cyclopropyl-2,6-difluorophenyl)amino)-6-(3-morpholinopropoxy)-1,3,5-triazin-2-yl)amino)benzonitrile | 6h |
| 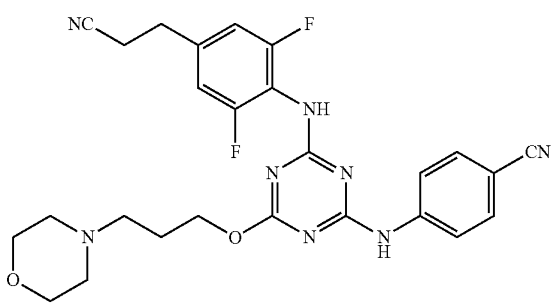 [SMILES: N#CCCc1cc(F)c(Nc2nc(Nc3ccc(C#N)cc3)nc(OCCCN3CCOCC3)n2)c(F)c1] | 4-((4-((4-(2-cyanoethyl)-2,6-difluorophenyl)amino)-6-(3-morpholinopropoxy)-1,3,5-triazin-2-yl)amino)benzonitrile | 6i |
| 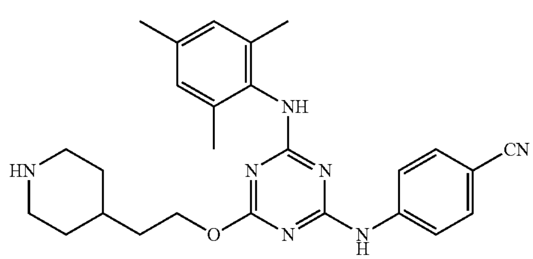 [SMILES: Cc1cc(C)c(Nc2nc(Nc3ccc(C#N)cc3)nc(OCCC3CCNCC3)n2)c(C)c1] | 4-((4-(mesitylamino)-6-(2-(piperidin-4-yl)ethoxy)-1,3,5-triazin-2-yl)amino)benzonitrile | 12a |

TABLE 1-continued

Compounds of the present invention

| Structure | Name | Compound Name |
|---|---|---|
| 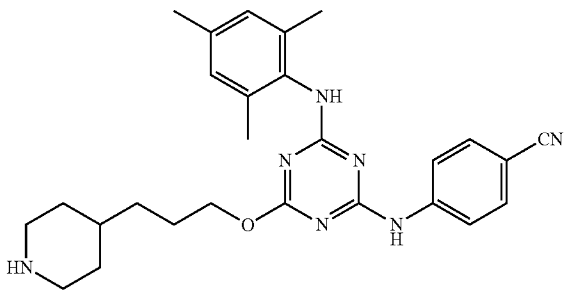 [SMILES: Cc1cc(C)c(Nc2nc(Nc3ccc(C#N)cc3)nc(OCCCC3CCNCC3)n2)c(C)c1] | 4-((4-(mesitylamino)-6-(3-(piperidin-4-yl)propoxy)-1,3,5-triazin-2-yl)amino)benzonitrile | 12b |
| 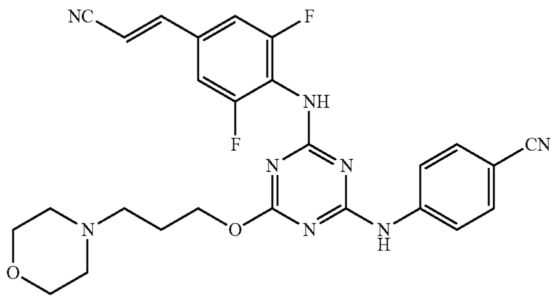 [SMILES: N#C/C=C/c1cc(F)c(Nc2nc(Nc3ccc(C#N)cc3)nc(OCCCN3CCOCC3)n2)c(F)c1] | (E)-4-((4-((4-(2-cyanovinyl)-2,6-difluorophenyl)amino)-6-(3-morpholinopropoxy)-1,3,5-triazin-2-yl)amino)benzonitrile | JLJ0562; 6j |
| 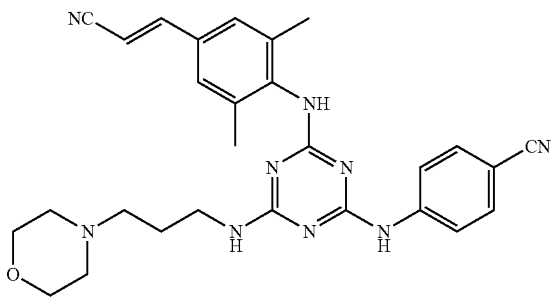 [SMILES: Cc1cc(/C=C/C#N)cc(C)c1Nc1nc(NCCCN2CCOCC2)nc(Nc2ccc(C#N)cc2)n1] | (E)-4-((4-((4-(2-cyanovinyl)-2,6-dimethylphenyl)amino)-6-((3-morpholinopropyl)amino)-1,3,5-triazin-2-yl)amino)benzonitrile | JLJ0596 |
| 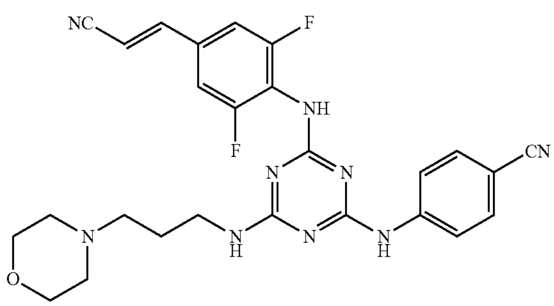 [SMILES: N#C/C=C/c1cc(F)c(Nc2nc(NCCCN3CCOCC3)nc(Nc3ccc(C#N)cc3)n2)c(F)c1] | (E)-4-((4-((4-(2-cyanovinyl)-2,6-difluorophenyl)amino)-6-((3-morpholinopropyl)amino)-1,3,5-triazin-2-yl)amino)benzonitrile | JLJ0597 |
| 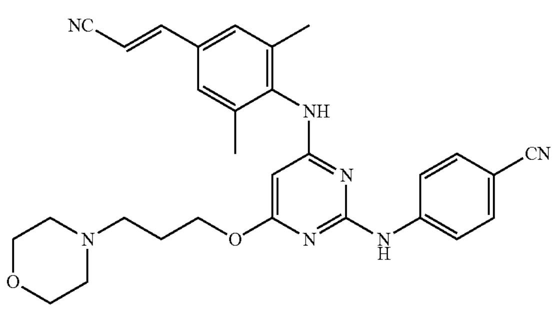 | (E)-4-((4-((4-(2-cyanovinyl)-2,6-dimethylphenyl)amino)-6-(3-morpholinopropoxy)pyrimidin-2-yl)amino)benzonitrile | JLJ0617; 5c |

TABLE 1-continued

Compounds of the present invention

| Structure | Name | Compound Name |
|---|---|---|
| 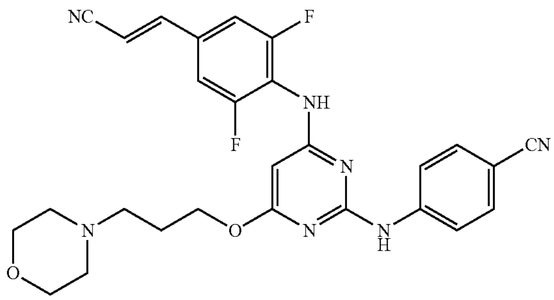 [SMILES: N#C/C=C/c1cc(F)c(Nc2cc(OCCCN3CCOCC3)nc(Nc3ccc(C#N)cc3)n2)c(F)c1] | (E)-4-((4-((4-(2-cyanovinyl)-2,6-difluorophenyl)amino)-6-(3-morpholinopropoxy)pyrimidin-2-yl)amino)benzonitrile | JLJ0625; 5d |
| 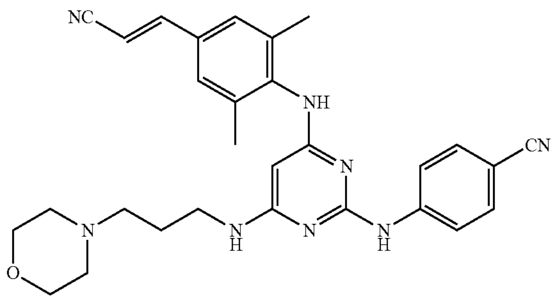 [SMILES: Cc1cc(/C=C/C#N)cc(C)c1Nc1cc(NCCCN2CCOCC2)nc(Nc2ccc(C#N)cc2)n1] | (E)-4-((4-((4-(2-cyanovinyl)-2,6-dimethylphenyl)amino)-6-((3-morpholinopropyl)amino)pyrimidin-2-yl)amino)benzonitrile | JLJ0618 |
| 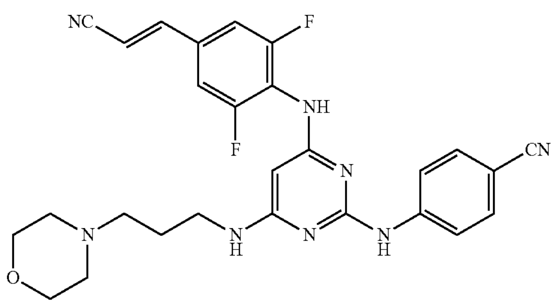 [SMILES: N#C/C=C/c1cc(F)c(Nc2cc(NCCCN3CCOCC3)nc(Nc3ccc(C#N)cc3)n2)c(F)c1] | (E)-4-((4-((4-(2-cyanovinyl)-2,6-difluorophenyl)amino)-6-((3-morpholinopropyl)amino)pyrimidin-2-yl)amino)benzonitrile | JLJ0619 |

Preparation of the Compounds of the Invention

Compounds of formula (I)-(Ia) and formula (II)-(IIa) may be prepared by the general schemes described herein, using the synthetic method known by those skilled in the art. The following examples illustrate non-limiting embodiments of the invention.

In a non-limiting embodiment, the synthesis of pyrimidines and triazines of the present invention is accomplished by coupling a 2,4,6-trichloropyrimidine or a 2,4,6-trichlorotriazine with two anilines and an alcohol. The two anilines may be identical or two different anilines. In some embodiments, the reaction may be performed in the presence of a base. Non-limiting examples of bases include diisoproyplethylamine (DIPEA), triethylamine (TEA), pyridine, sodium hydride, and the like, and any combination thereof. In one embodiment, the base is DIPEA. In another embodiment, the base is sodium hydride. The reaction may also be performed in the presence of an organic solvent. Examples of organic solvents include, but are not limited to, ethanol, methanol, isopropanol, tetrahydrofuran, acetonitrile, dichloromethane, 1,4-dioxane, 1,2,-dimethoxyethane, and the like, and any combination thereof. In one embodiment, the organic solvent is tetrahydrofuran. In another embodiment, the organic solvent is acetonitrile. In another embodiment, the organic solvent is dichloromethane. In one embodiment, the coupling reaction takes place at an elevated temperature ranging from 50° C. to 250° C. Non-limiting examples of coupling methods include heating in tetrahydrofuran at 65° C., heating in acetonitrile at 70° C., and heating in a microwave.

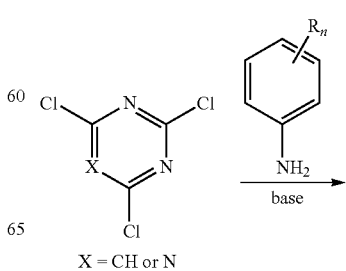

X = CH or N

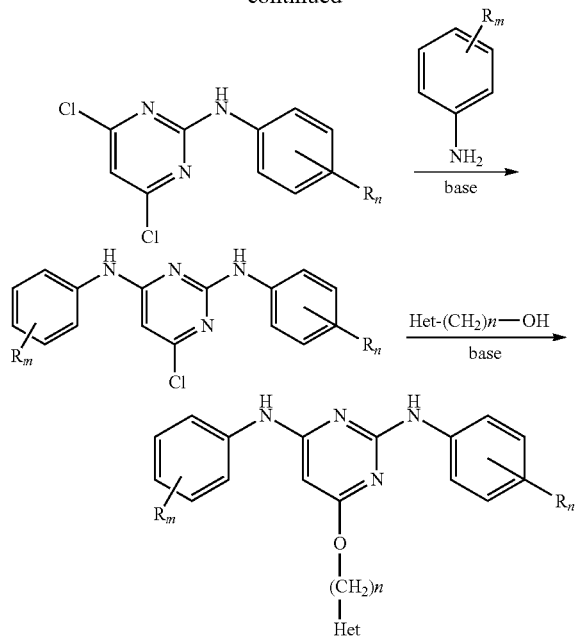

The compounds of the invention may possess one or more stereocenters, and each stereocenter may exist independently in either the (R) or (S) configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxy benzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

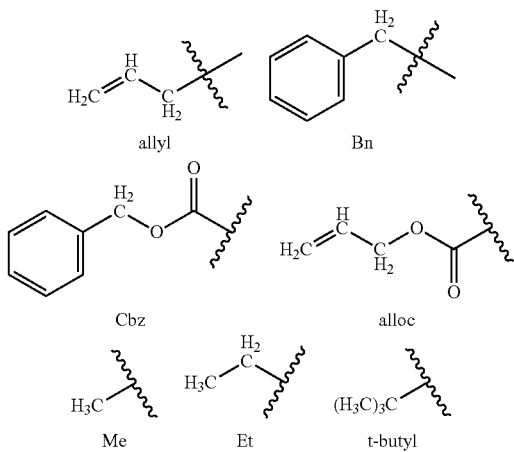

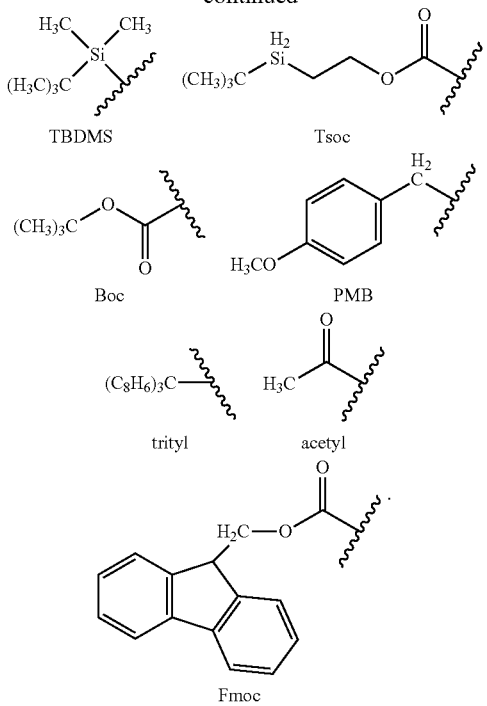

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Methods of the Invention

The invention includes a method of treating or preventing an HIV-1 infection in a subject in need thereof. The method comprises administering to the subject an effective amount of a therapeutic composition comprising a compound of the invention. In one embodiment, the method further comprises administering to the subject an additional therapeutic agent useful in treating HIV-1 infection.

In one embodiment, administering the compound of the invention to the subject allows for administering a lower dose of the additional therapeutic agent compared to the dose of the additional therapeutic agent alone that is required to achieve similar results in treating or preventing an HIV-1 infection in the subject. For example, in one embodiment, the compound of the invention enhances the anti-HIV-1 activity of the additional therapeutic compound, thereby allowing for a lower dose of the therapeutic compound to provide the same effect.

In one embodiment, the compound of the invention and the additional therapeutic agent are co-administered to the subject. In another embodiment, the compound of the invention and the additional therapeutic agent are co-formulated and co-administered to the subject.

In one embodiment, the subject is a mammal. In another embodiment, the mammal is a human.

Combination Therapies

The compounds useful within the methods of the invention may be used in combination with one or more additional compounds useful for treating HIV infections. These additional compounds may comprise compounds that are commercially available or synthetically accessible to those skilled in the art. These additional compounds are known to treat, prevent, or reduce the symptoms of HIV infections.

In non-limiting examples, the compounds useful within the invention may be used in combination with one or more of the following anti-HIV drugs:

HIV Combination Drugs: efavirenz, emtricitabine or tenofovir disoproxil fumarate (Atripla®/BMS, Gilead); emtricitabine, rilpivirine, tenofovir (Complera®/Gilead); lamivudine or zidovudine (Combivir®/GSK); abacavir or lamivudine (Epzicom®/GSK); abacavir, lamivudine or zidovudine (Trizivir®/GSK); emtricitabine, tenofovir disoproxil fumarate (Truvada®/Gilead).

Entry and Fusion Inhibitors: maraviroc (Celsentri®, Selzentry®/Pfizer); pentafuside or enfuvirtide (Fuzeon®/Roche, Trimeris).

Integrase Inhibitors: raltegravir or MK-0518 (Isentress®/Merck).

Non-Nucleoside Reverse Transcriptase Inhibitors: delavirdine mesylate or delavirdine (Rescriptor®/Pfizer); nevirapine (Viramune®/Boehringer Ingelheim); stocrin or efavirenz (Sustiva®/BMS); etravirine (Intelence®/Tibotec); rilpivirine (Edurant®/Tibotec).

Nucleoside Reverse Transcriptase Inhibitors: lamivudine or 3TC (Epivir®/GSK); FTC, emtricitabine or coviracil (Emtriva®/Gilead); abacavir (Ziagen®/GSK); zidovudina, ZDV, azidothymidine or AZT (Retrovir®/GSK); ddI, dideoxyinosine or didanosine (Videx®/BMS); abacavir sulfate plus lamivudine (Epzicom®/GSK); stavudine, d4T, or estavudina (Zerit®/BMS); tenofovir, PMPA prodrug, or tenofovir disoproxil fumarate (Viread®/Gilead).

Protease Inhibitors: amprenavir (Agenerase®/GSK, Vertex); atazanavir (Reyataz®/BMS); tipranavir (Aptivus®/Boehringer Ingelheim); darunavir (Prezist®/Tibotec); fos-amprenavir (Telzir®, Lexiva®/GSK, Vertex); indinavir sulfate (Crixivan®/Merck); saquinavir mesylate (Invirase®/Roche); lopinavir or ritonavir (Kaletra®/Abbott); nelfinavir mesylate (Viracept®/Pfizer); ritonavir (Norvir®/Abbott).

A synergistic effect may be calculated, for example, using suitable methods such as, for example, the Sigmoid-$E_{max}$ equation (Holford & Scheiner, 1981, Clin. Pharmacokinet 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of an HIV infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat HIV infections in the patient. An effective amount of the therapeutic compound necessary to achieve a therapeutic effect may vary according to factors such as the state of the disease or disorder in the patient; the age, sex, and weight of the patient; and the ability of the therapeutic compound to treat HIV infections in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of HIV infections in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of HIV infections in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of HIV infections in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as from about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In one embodiment, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art recognizes, or is able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Extension into the Entrance Channel of HIV-1 Reverse Transcriptase-Crystallography and Enhanced Solubility The results described herein demonstrate that it is possible to extend anilinylazine NNRTIs, such as compounds 2j and 2k, into the entrance channel of the NNRTI binding site to achieve profound improvements in aqueous solubility. As demonstrated herein, compounds 2j and 2k are similar in anti-HIV activity to the drug nevirapine, but they have 200 to 500-fold greater solubility than the parent compound 2a and the diarylpyrimidines dapivirine and rilpivirine. These results suggest that the analogous application of this approach to the diarylpyrimidines may be expected to yield similar benefits for solubility, while retaining their excellent activity towards viral variants.

Initial Modeling Studies

Efforts to discover new series of NNRTIs have combined computer-aided design, synthesis, and biological assaying (Jorgensen et al., 2006, Bioorg. Med. Chem. Lett. 16:663; Jorgensen, 2009, Acc. Chem. Res. 42:724). For two picomolar inhibitors, which feature a catechol diether substructure (Bollini et al., 2011, J. Med. Chem. 54:8582), X-ray crystal structures for their complexes with wild-type (WT) HIV-RT have been reported (Frey et al., 2012, J. Am. Chem. Soc. 134:19501). One of the earliest series that had been investigated was anilinylazines containing a dimethylallyloxy substituent. This work culminated in the pyrimidine 1 and the corresponding 1,3,5-triazine (2a; FIG. 1), which yield EC$_{50}$ values of, respectively, 2 and 11 nM in a standard assay using MT-2 cells infected with wild-type HIV-1 (Thakur et al., 2006, Bioorg. Med. Chem. Lett. 16:5664). Though results of molecular modeling, starting from the 1S9E crystal structure of an anilinyltriazene (Das et al., 2004, J. Med. Chem., 47:2550), were reported for complexes of the inhibitors with HIV-RT, the binding mode for 1 was confirmed by an X-ray crystal structure. This structure is illustrated in FIGS. 2 and 3.

Figure 2:
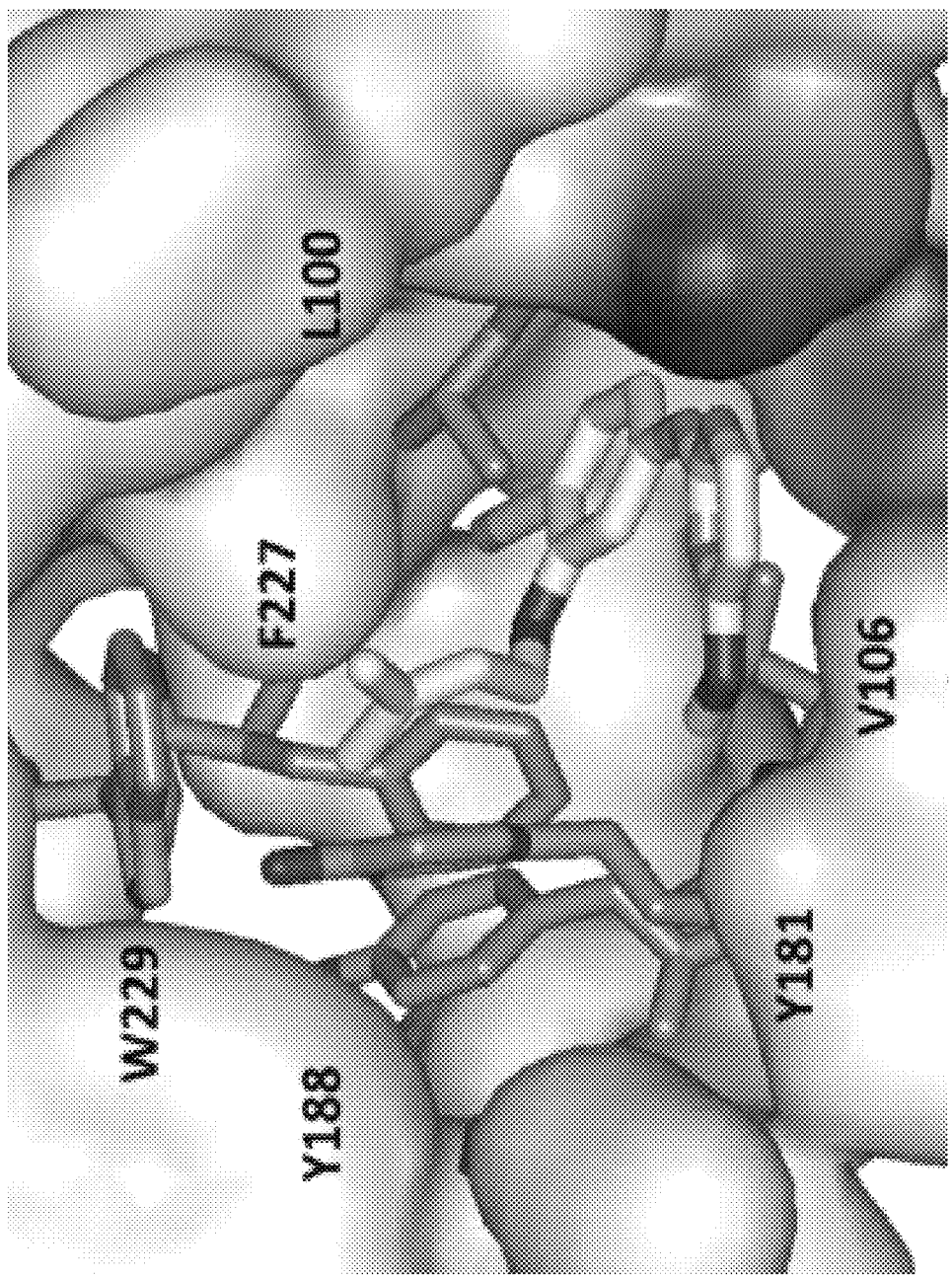
FIG. 2 is an image illustrating the 1.95-Å crystal structure of compound 1 with wild-type HIV-RT. Carbon atoms of compound 1 are in light gray. Some protein residues are omitted for clarity.
Figure 3:
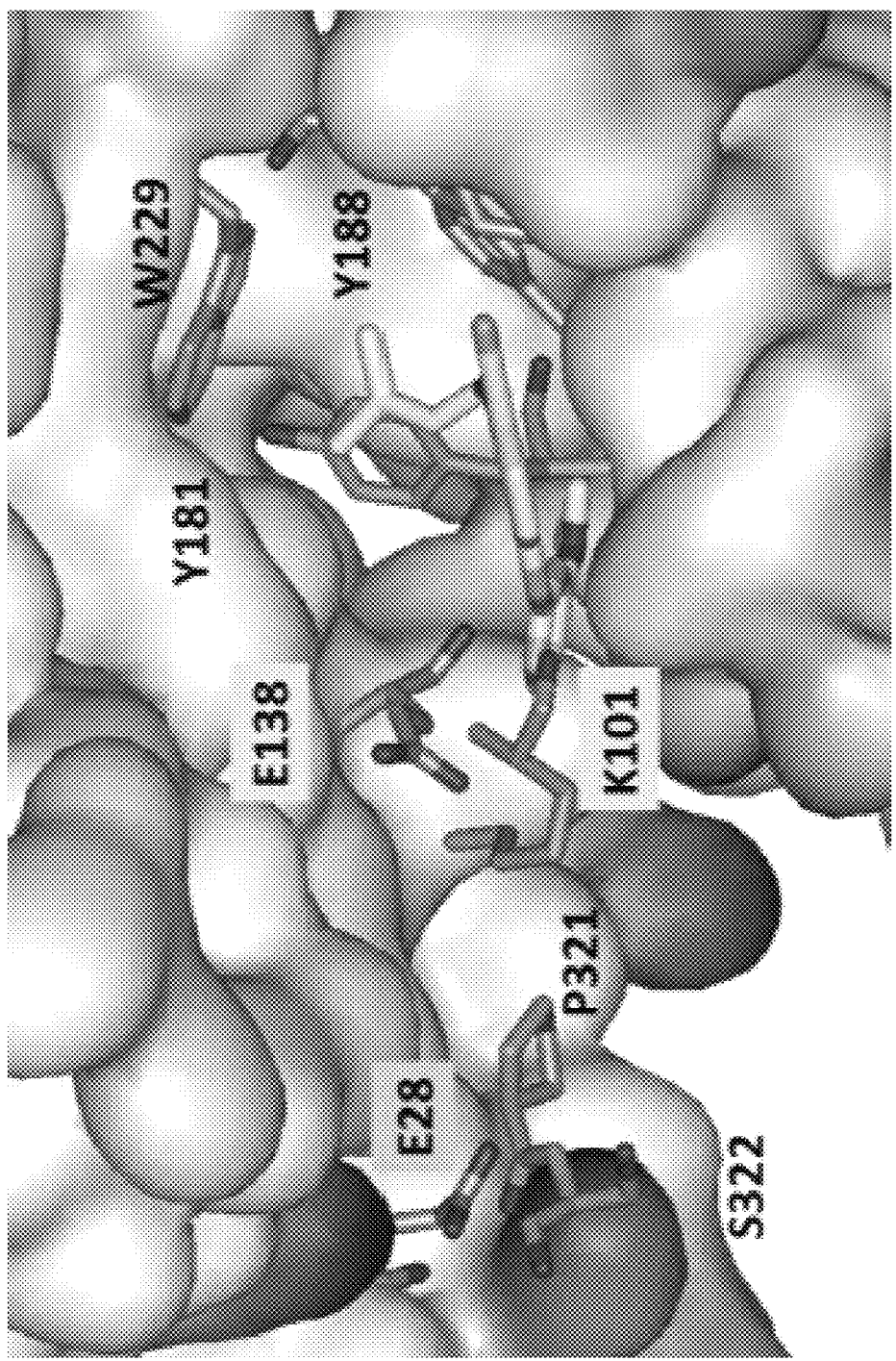
FIG. 3 is an image illustrating the right-side view of the crystal structure of compound 1 bound to wild-type HIV-RT in FIG. 2. Some residues are omitted for clarity. Coordinates are deposited in the PDB as structure 4KO0.

Consistent with the 1S9E structure and the modeling, compound 1 resides in the NNRTI binding site with the hydrophobic dimethylallyl group positioned in the π-box formed by Tyr181, Tyr188, Phe227, and Trp229 (FIG. 2). There are also hydrogen bonds between the backbone 0 and N of Lys101 and the amidine moiety of compound 1, which are clearer from the orthogonal view in FIG. 3. FIG. 3 also highlights a salt bridge between the side chains of Glu138 and Lys101, a feature that is not always found in NNRTI complexes, e.g., the 1S9E structure (Das et al., 2004, J. Med. Chem., 47:2550). The X-ray results provide important validation of the structure-activity patterns that were obtained for compound 1 and its analogs (Thakur et al., 2006, Bioorg. Med. Chem. Lett. 16:5664). Although not wishing to be bound by any particular theory, these results suggest that the poor activity of these compounds towards viral variants containing the clinically important Tyr181Cys mutation owing to the substantial contact of Tyr181 with the dimethylallyl group of compound 1 (Thakur et al., 2006, Bioorg. Med. Chem. Lett. 16:5664; Jorgensen et al., 2011, J. Am. Chem. Soc. 22:15686).

Subsequent efforts included the probing of relatively unexplored regions including the 'eastern channel' or 'groove' (Leung et al., 2010, Bioorg. Med. Chem. Lett. 20:2485) extending back and down from the cyano group of compound 1 in FIG. 2 and the 'entrance channel' extending into the solvent-exposed region to the left of Lys101 in FIG. 3 (Ekkati et al., 2012, Bioorg. Med. Chem. Lett. 22:1565). In one embodiment, such extensions may (1) improve potency towards both wild-type HIV-1 and variants containing common NNRTI-induced point mutations, and/or (2) improve physical properties of the NNRTIs. Extension into the entrance channel for compounds 1 and 2 would require attachment of a substituent at C6 of the azine rings (FIG. 2). It was not clear that this would be successful owing to possible unfavorable contacts, especially with Glu138 (FIG. 3). However, various substituents could be attached at this position, although with some loss of potency (Ekkati et al., 2012, Bioorg. Med. Chem. Lett. 22:1565). For example, as summarized in Table 2, the methoxyethoxy and methoxytriethoxy containing compounds 2c and 2e yield EC$_{50}$ values of 97 and 380 nM in the MT-2 cell assay, while the parent compound 2a and dimethoxy analog 2b were 11-nM and 22-nM inhibitors. Large, dimeric NNRTIs could be accommodated. For example, compound 3 (FIG. 1) yielded an EC$_{50}$ of 170 nM (Ekkati et al., 2012, Bioorg. Med. Chem. Lett. 22:1565).

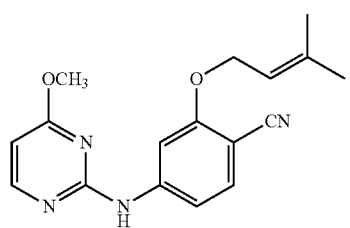

1

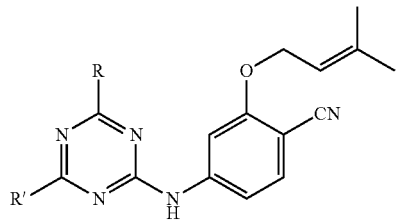

2

TABLE 2

Anti-HIV-1 Activity (EC$_{50}$) and cytotoxicity (CC$_{50}$), μM[a]

| Compound | R | R' | EC$_{50}$ | CC$_{50}$ |
|---|---|---|---|---|
| 2a[b] | OCH$_3$ | H | 0.011 | 42 |
| 2b[b] | OCH$_3$ | OCH$_3$ | 0.022 | >100 |
| 2c[c] | OCH$_3$ | OCH$_2$CH$_2$OCH$_3$ | 0.097 | 8.6 |
| 2d[c] | CH$_2$CH$_3$ | OCH$_2$CH$_2$OCH$_3$ | 0.057 | 2.1 |
| 2e[c] | OCH$_3$ | (OCH$_2$CH$_2$)$_3$OCH$_3$ | 0.380 | 4.2 |
| 2f | OCH$_3$ | (OCH$_2$CH$_2$)$_4$NH$_2$ | 2.2 | 23 |
| 2g | OCH$_3$ | (OCH$_2$CH$_2$)$_6$NH$_2$ | 5.0 | 18 |
| 2h[c] | OCH$_3$ | OCH$_2$CH$_2$-4-MePip | 0.320 | 7.0 |
| 2i[c] | OCH$_3$ | OCH$_2$CH$_2$-2-THP | 1.2 | 4.2 |
| 2j | OCH$_3$ | OCH$_2$CH$_2$-Morph | 0.092 | 2.5 |
| 2k | OCH$_3$ | OCH$_2$CH$_2$CH$_2$-Morph | 0.095 | 3.6 |
| 2l | CH$_2$CH$_3$ | OCH$_2$CH$_2$-Morph | 0.150 | 0.8 |
| 2m | c-C$_3$H$_5$ | OCH$_2$CH$_2$-Morph | 0.100 | 0.9 |
| nevirapine | | | 0.110 | >100 |
| efavirenz | | | 0.002 | 15 |
| rilpivirine | | | 0.001 | 8 |

[a]4-MePip = N-methylpiperazinyl; 2-THP = 2-tetrahydropyranyl (racemic); Morph = N-morpholinyl.
[b]Thakur et al., 2006, Bioorg. Med. Chem. Lett. 16: 5664.
[c]Ekkati et al., 2012, Bioorg. Med. Chem. Lett. 22: 1565.

Investigation of the Entrance Channel

Figure 4:
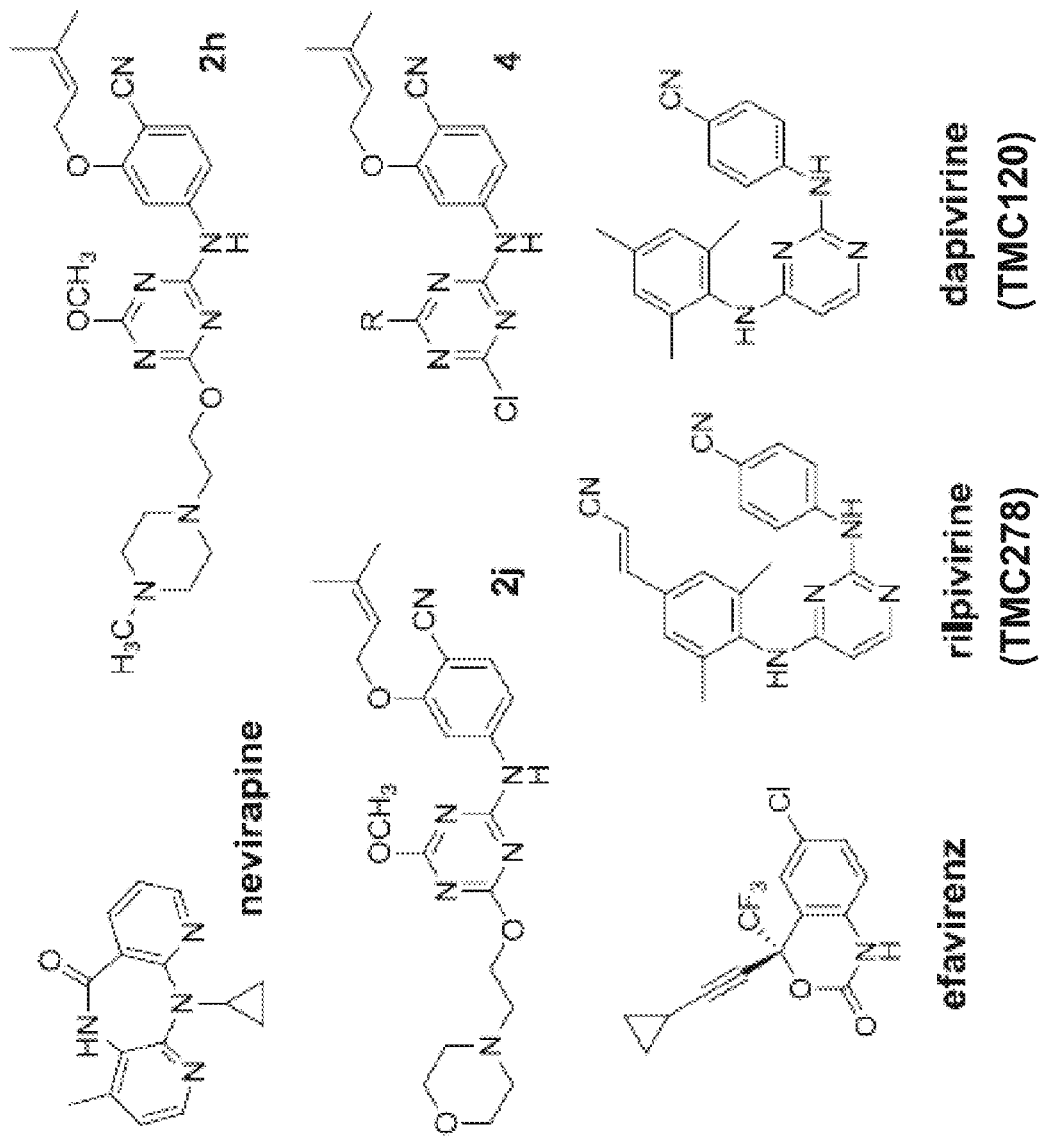
FIG. 4 illustrates the structures of nevirapine, efavirenz, rilpivirine (TMC278), dapivirine (TMC120), reference compounds 2h and 4, and 4-((4-methoxy-6-(2-morpholinoethoxy)-1,3,5-triazin-2-yl)amino)-2-((3-methylbut-2-en-1-yl)oxy)benzonitrile (compound 2j).
Figure 5:
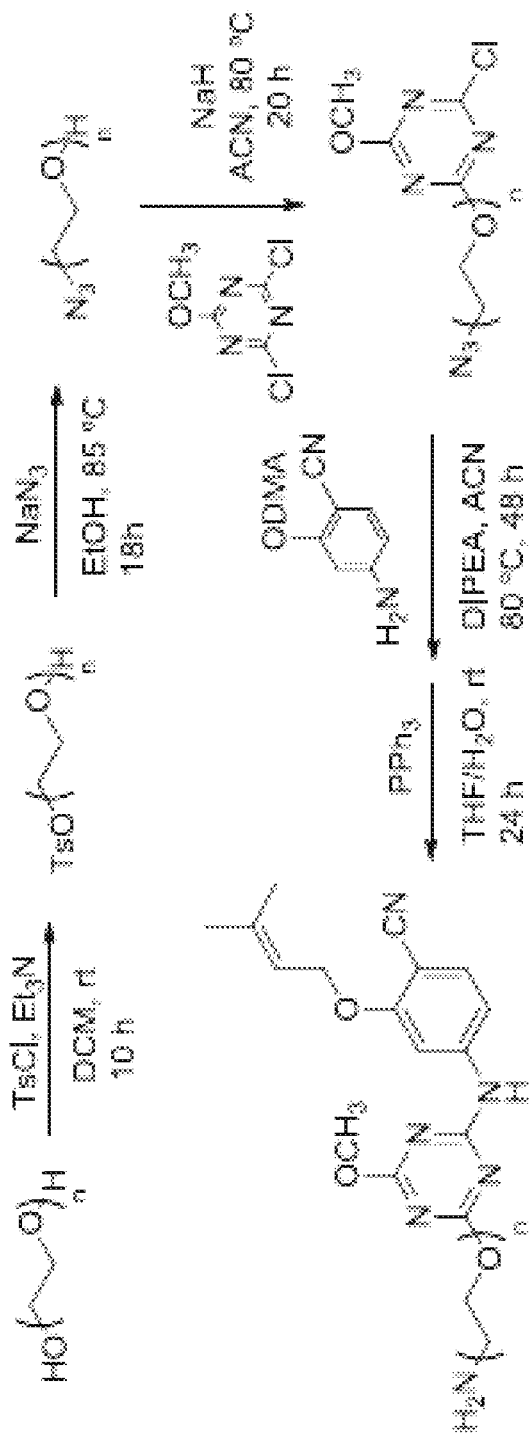
FIG. 5 is an image illustrating an exemplary synthesis of compounds 2f (n=4) and 2g (n=6) of the present invention.

Additional compounds were synthesized and assayed, specifically, the amino-terminating compounds 2f and 2g and the morpholinoethoxy and -propoxy analogs 2j-2m (FIG. 4; Table 2). The latter compounds were prepared using methods previously described via S$_N$Ar reactions of alkoxides with the intermediate compound 4 (FIG. 4) (Molina et al., 2011, Lancet 378:238; Ekkati et al., 2012, Bioorg. Med. Chem. Lett. 22:1565); however, an alternative route was developed for the amines (FIG. 5). The S$_N$Ar reaction was performed earlier in the sequence to install the side chain on dichloromethoxytriazene, and the amino group was unmasked in the last step.

Activities against the IIIB strain of HIV-1 were measured using MT-2 human T-cells using methods previously described (Jorgensen et al., 2006, Bioorg. Med. Chem. Lett. 16:663; Jorgensen, 2009, Acc. Chem. Res. 42:724; Bollini et al., 2011, J. Med. Chem. 54:8582; Frey et al., 2012, J. Am. Chem. Soc. 134:19501; Thakur et al., 2006, Bioorg. Med. Chem. Lett. 16:5664; Jorgensen et al., 2011, J. Am. Chem. Soc. 133:15686; Leung et al., 2010, Bioorg. Med. Chem. Lett. 20:2485; Ekkati et al., 2012, Bioorg. Med. Chem. Lett. 22:1565); EC$_{50}$ values are obtained as the dose required to achieve 50% protection of the infected cells by the MTT colorimetric method. Simultaneously, CC$_{50}$ values for inhibition of MT-2 cell growth by 50% are obtained. The identity of all assayed compounds was confirmed by $^1$H and $^{13}$C NMR spectroscopy and high-resolution mass spectrometry; purity was >95% as judged by high-performance liquid chromatography.

The amines 2f and 2g were of interest to test the effects of a positive charge at the end of the side chains and increases in length beyond compound 2e. The results for compounds 2f and 2g in Table 2 show that these modifications are not beneficial for activity. The interest in the morpholine-containing compounds was particularly high since this modification would likely improve the solubility of the compounds. Indeed, good activity was observed for compounds 2j (92 nM) and 2k (95 nM). This represents significant improvement over the methylpiperazinyl analog 2h and and THP analog 2i.

Furthermore, the aqueous solubilities of compounds 2a, 2j, 2k, dapivirine (TMC120), and efavirenz were quantified using a previously described shake-flask method with UV detection (Agilent 8453; Baka et al., 2008, J. Pharm. Biomed. Anal. 46:335). The results are shown in Table 3, which also includes previous reports for rilpivirine. Addition of the morpholinoalkoxy substituent to compound 2a to yield compounds 2j or 2k delivers a 400 to 500-fold improvement in solubility. The results for compounds 2j and 2k are similar to that for evafirenz and place them within the normal range observed for oral drugs (Jorgensen and Duffy, 2002, Adv. Drug Deliv. Rev. 54:335). In contrast, the sub-µg/mL solubilities for dapivirine and rilpivirine are well outside the normal range. Thus, compounds 2j and 2k have good aqueous solubility and potencies similar to that of nevirapine. Though their activities in the wild-type cell assay are 100-fold less than for rilpivirine or dapivirine, their solubilities are 175 to 350-fold greater.

TABLE 3

| Aqueous Solubility at pH 6.5 (S) | | | |
|---|---|---|---|
| Compound | S, µg/mL | Compound | S, µg/mL |
| 2a | 0.1 | efavirenz | 68.0 |
| 2j | 42.2 | dapivirine | 0.15 |
| 2k | 52.3 | rilpivirine | 0.24[a], 0.02[b] |

[a]Sun et al., 2012, Bioorg. Med. Chem. Lett. 22: 2376, pH 7.4.
[b]Janssen et al., 2005, J. Med. Chem. 48: 1901, pH 7.

Figure 6:
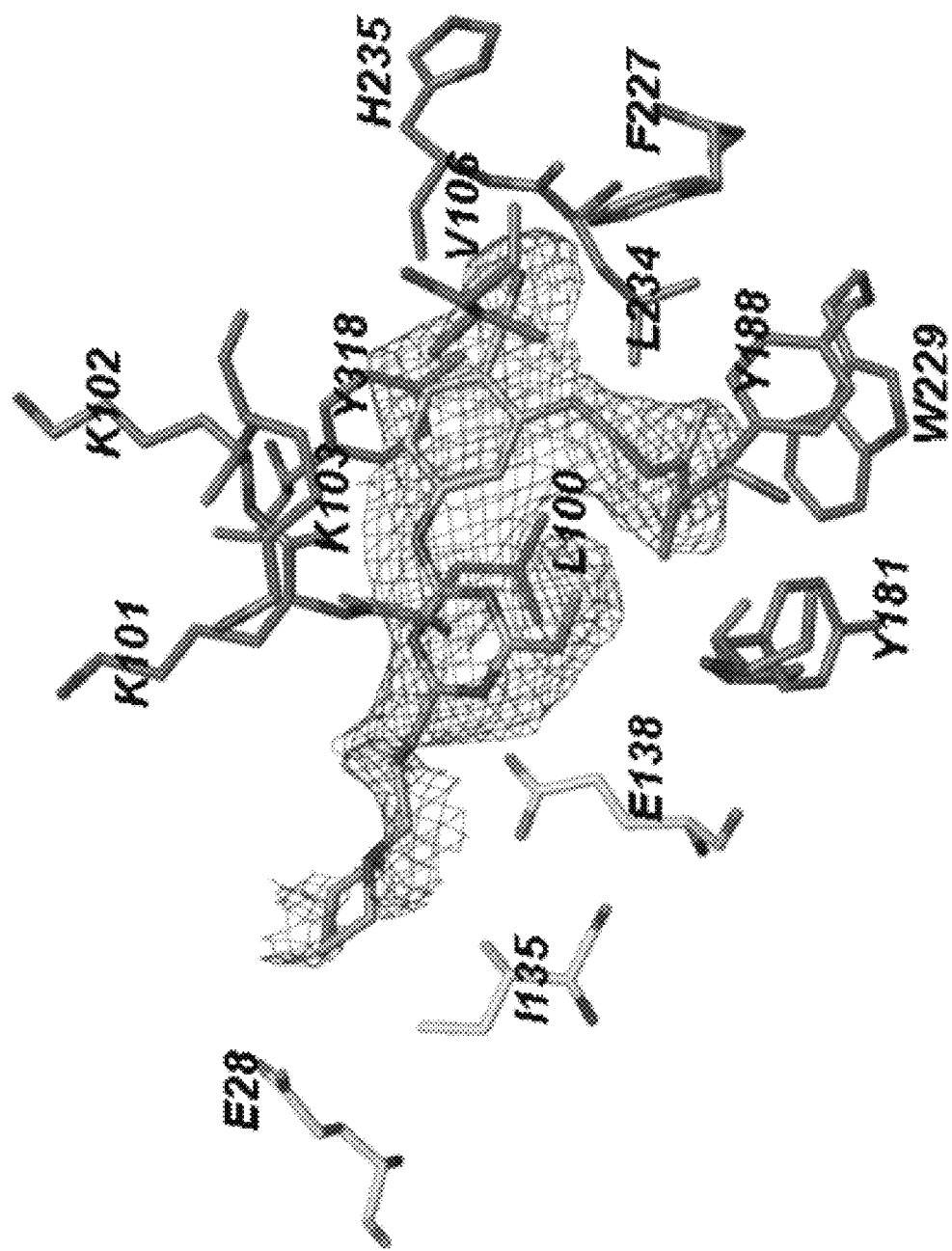
FIG. 6 is an image illustrating an omit Fo-Fc electron density map at a contour level of 3.0 σ showing compound 2j in the NNRTI binding site of HIV-1 RT with extension towards Glu28 in the entrance channel.
Figure 7:
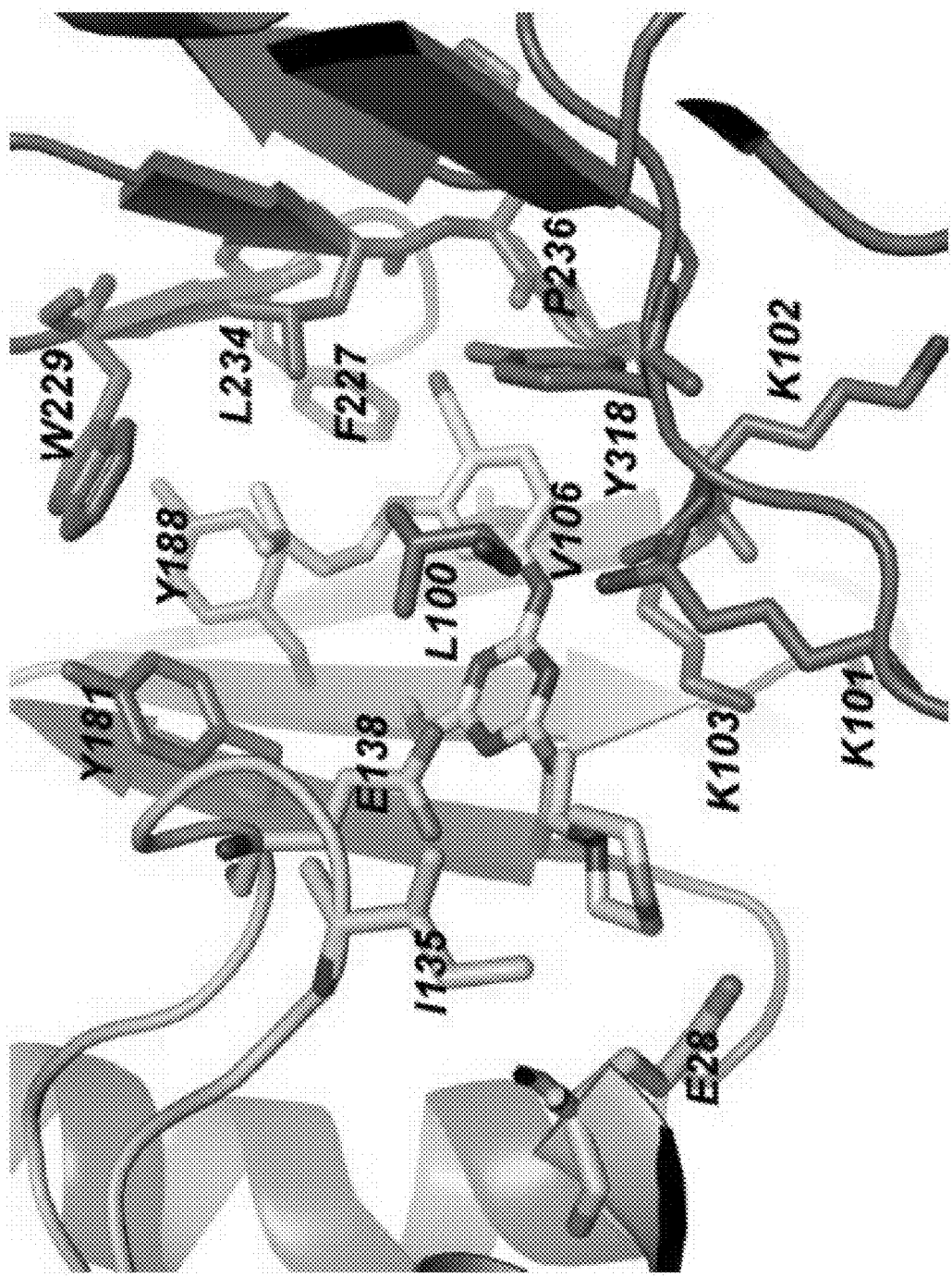
FIG. 7 is an image illustrating the crystal structure of compound 2j with HIV-1 RT; the morpholinoethoxy side chain projects towards Glu28B. Coordinates are deposited in the PDB as structure 4KKO.

Finally, to confirm the expectation of the placement of the morpholinoethoxy side chain in the entrance channel and to elucidate its contacts, a co-crystal structure of compound 2j and wild-type HIV-RT was pursued using similar methods as those previously reported (Frey et al., 2012, J. Am. Chem. Soc. 134:19501). Crystals with the recombinant RT52A enzyme diffracted to 2.9-Å resolution, data were collected at the Brookhaven NSLS on beam line X25, and the structure was solved by molecular replacement using the 2ZD1 structure of rilpivirine with HIV-RT25 as the search model. The electron density for the non-nucleoside binding region was ordered and provides clear characterization of the interactions with the inhibitor (FIG. 6). An alternative rendering of the structure is provided in FIG. 7.

The positioning of compound 2j in the NNRTI binding site is the same as for compound 1 including the hydrogen bonds with Lys101 and the placement of the dimethylallyl group in the π-box; however, the salt bridge between Glu138 and Lys101 is no longer present (FIG. 6). Overall, the co-crystal structures reported here for compounds 1 and 2j have an rmsd of only 1.4 Å for an all-atom alignment. Since the contact between Tyr181 and the dimethylallyl group is retained, compound 2j does not show activity towards the Y181C-containing viral variant. Most notably, the structure for compound 2j confirms the anticipated extension of the morpholinoethoxy side chain into the entrance channel towards Glu28. The carboxylate group of Glu138 contacts the carbon atoms of the ethoxy subunit with O—C separations of 2.8-3.6 Å. The carboxylate oxygens are also 3.8 and 4.4 Å from the morpholine nitrogen, which is presumably protonated. In addition, the morpholine oxygen is proximal to the carboxylate carbon (4.1 Å) and oxygens (3.4 and 4.3 Å) of Glu28.

Though it might seem that replacement of the oxygen of the morpholine with a positively charged group would enhance binding, beneficial effects were not apparent for the 4-methylpiperazinyl analog 2h (Table 2). In this case, only one of the tertiary nitrogens would be protonated near pH 7, since the pKa values for 1,4-dimethylpiperazine are 8.4 and 3.8 (Khalili et al., 2009, J. Chem. Eng. Data 54:2914). Thus, a favorable electrostatic interaction with either Glu138 or Glu28 has to be sacrificed.

Figure 8:
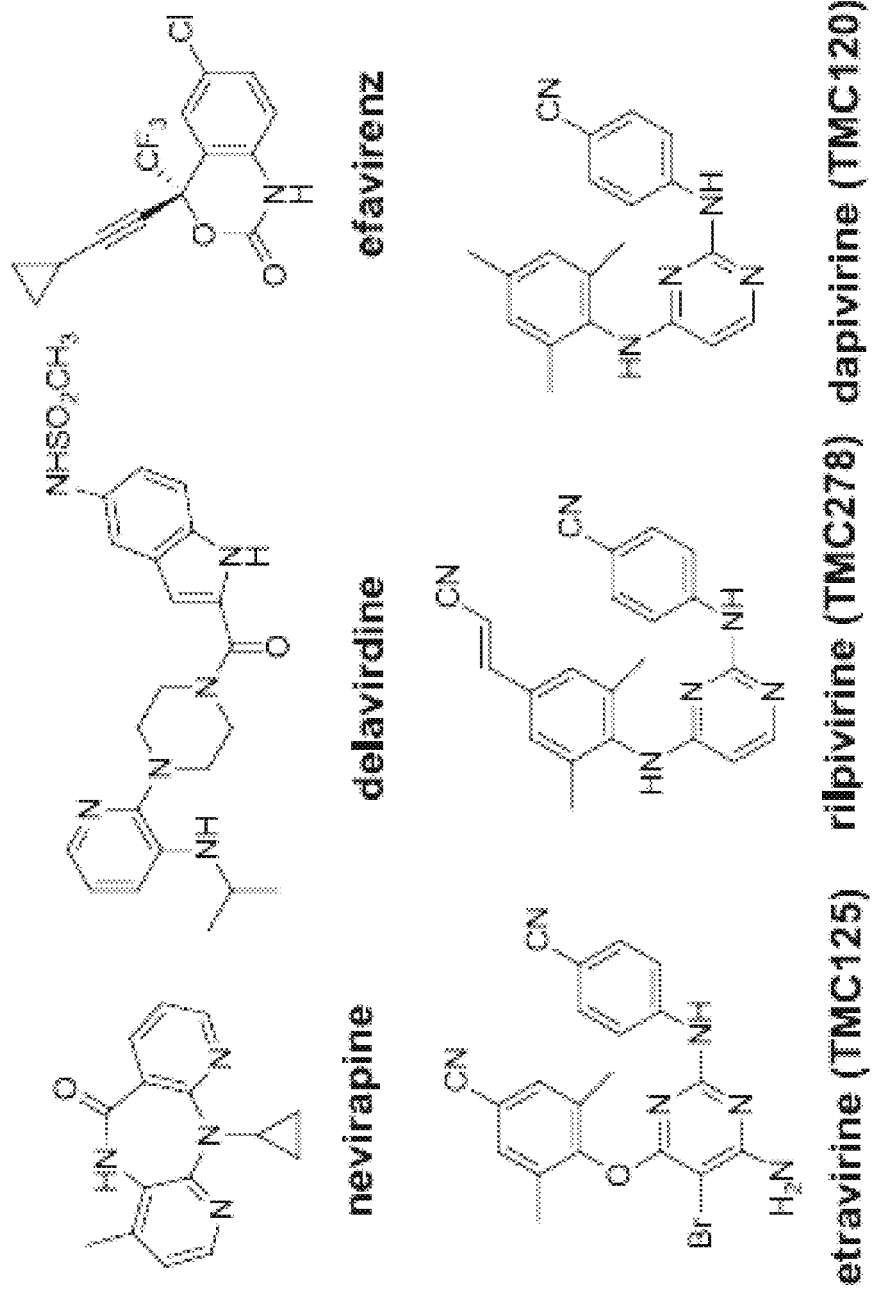
FIG. 8 illustrates the structures of nevirapine, delavirdine, efavirenz, etravirine (TMC125), rilpivirine (TMC278), and dapivirine (TMC120).

Example 2: Optimization of Diarylazines as Anti-HIV Agents with Dramatically Enhanced Solubility The results described herein provide promising, new NNRTIs derived from structural analyses suggesting the possibility of appending solubilizing groups to the diarylazine class of NNRTIs at the 6-position in the azine ring. Notably, compound 6d has similar potency as etravirine in infected T-cell assays using wild-type HIV-1 (IIIB) as well as viral variants that incorporate the two most commonly found resistance mutations in the RT enzyme, Tyr181Cys and Lys103Asn. However, the solubility of 6d was found to be about 100-fold greater than the solubility observed for the diarylpyrimidines dapivirine (10a), etravirine, and rilpivirine (FIG. 8).

Initial Studies

Figure 9:
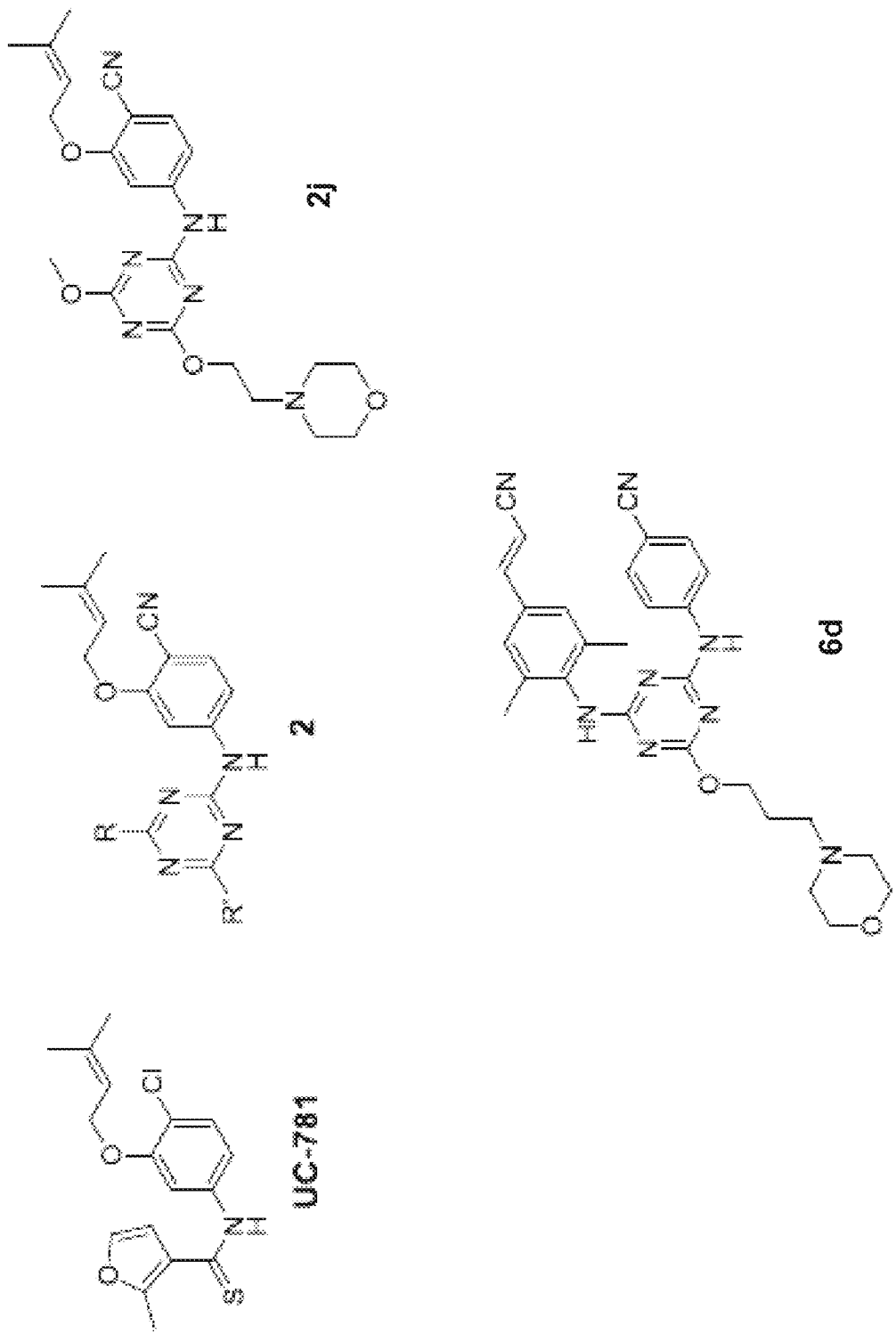
FIG. 9 illustrates the structures of reference compound UC-781, and compounds 2, 2j and 6d.

Poor solubility has been an issue with aminoazine-containing NNRTIs, such as compound 2. In view of the structural overlap of compound 2, the TMC compounds, and UC-781, it is not surprising that the measured solubility of compound 2a (R═H, R'═Me) is 0.1 µg/mL (Table 3; FIG. 9). In order to improve the solubility of such aminoazines, extensive modeling, synthesis, assaying and crystallography were undertaken. These studies demonstrated that it was possible to attach a solubilizing substituent as OR' that would extend into the entrance channel of the NNRTI binding site (Example 1). Specifically, compound 2j has S=42 µg/mL, while retaining an $EC_{50}$ of 92 nM in a standard assay using MT-2 cells infected with wild-type HIV-1 (Table 2; FIG. 9).

Investigating Improvements in Solubility of NNRTIs

Figure 10:
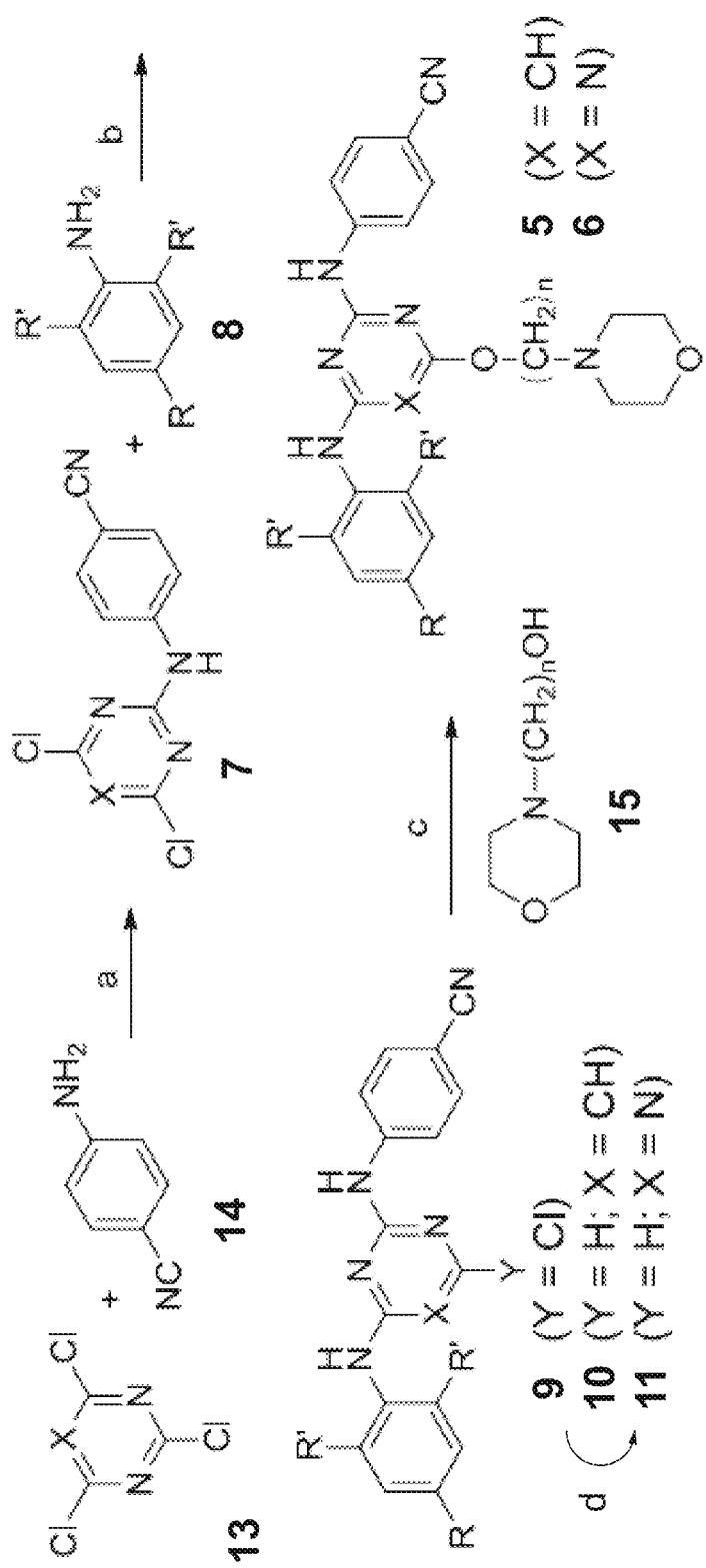
FIG. 10 is a synthetic scheme illustrating an exemplary synthesis of compounds 5 (X=CH) and 6 (X=N). Reagents: (a) diisopropylethylamine (DIPEA), tetrahydrofuran (THF), rt, overnight; (b) DIPEA, THF, 65° C., 2 days; (c) sodium hydride (NaH), THF, rt, overnight; (d) $H_2$/Pd—C.

Investigations into improving the solubility of diarylpyrimidines and triazines began by investigating compounds 5 and 6 (FIG. 10). Synthesis of the compounds proceeded as indicated via three SNAr reactions (Example 3). The final intermediate 7 was also reduced ($H_2$/Pd—C) to obtain the corresponding analogs 10 and 11 lacking the morpholinoalkoxy group. The identities of all assayed compounds were confirmed by $^1$H and $^{13}$C NMR and high-resolution mass spectrometry; purity was >95% as judged by high-performance liquid chromatography.

Activities against the IIIB and variant strains of HIV-1 were measured using MT-2 human T-cells, using previously described methods (Ekkati et al., 2012, Bioorg. Med. Chem. Lett. 22:1565; Bollini et al., 2011, J. Med. Chem. 54:8582). $EC_{50}$ values are obtained at the dose required to achieve 50% protection of the infected cells by the MTT colorimetric method. $CC_{50}$ values for inhibition of MT-2 cell growth by 50% are obtained simultaneously. Solubility measurements used a previously described shake-flask protocol with triplicate samples (Baka et al., 2008, J. Pharm. Biomed. Anal. 46:335). The compounds were dissolved in Britton-Robinson buffer and stirred in vials for 48 hours at 25° C. The pH of the buffer solutions was measured by a Corning General Purpose pH Combination probe (4136L21). The solution containing excess solid was filtered using a Whatman Mini-UniPrep syringeless filter device with a 0.45 μm pore size, and the supernatant was analyzed by UV-vis spectrophotometry (Agilent 8453). Piroxicam was used as a reference compound, and its observed solubility (7.2 μg/mL) was comparable to previously reported values (6.4 μg/mL; Baka et al., 2008, J. Pharm. Biomed. Anal. 46:335).

The results of the anti-viral assays are presented in Table 4. The synthesized TMC 120 (compound 10a) yielded 0.7 nM potency in the wild-type assay and 39 nM results for both the Y181C and K103N/Y181C variants. This is comparable to previously reported results of 1.2 nM, 7 nM, and 54 nM using MT-4 cells (Janssen et al., 2005, J. Med. Chem. 48:1901). Triazine 11a was found to have 2.3 nM, 47 nM, and 90 nM $EC_{50}$ values, while previously reported results in MT-4 assays yielded 0.3 nM, 8 nM, and 50 nM (Ludovici et al., 2001, Bioorg. Med. Chem. Lett. 11:2229). These results demonstrate that the anti-viral assays provide acceptable results. Although not wishing to be bound by any particular theory, these results suggest that the Y181C-containing strain used in this assay is more challenging.

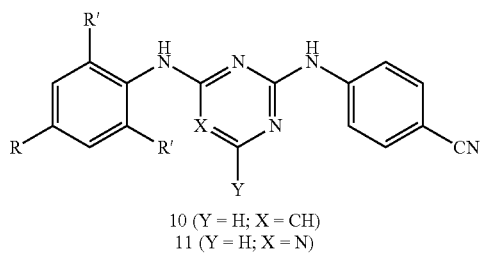

10 (Y = H; X = CH)
11 (Y = H; X = N)

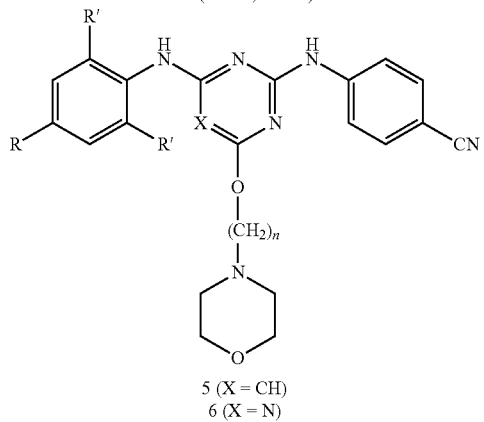

5 (X = CH)
6 (X = N)

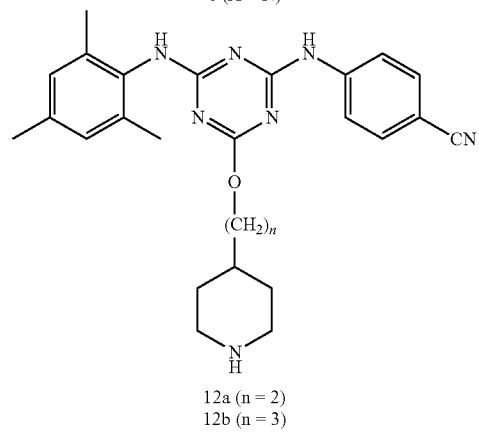

12a (n = 2)
12b (n = 3)

TABLE 4

Anti-HIV-1 Activity ($EC_{50}$) and cytotoxicity ($CC_{50}$), μM[a]

| Compnd | n | R' | R | WT | Y181C | K103N/Y181C | $CC_{50}$ |
|---|---|---|---|---|---|---|---|
| 10a[b] | — | Me | Me | 0.0007 | 0.039 | 0.039 | 2.0 |
| 5a | 2 | Me | Me | 0.019 | 0.700 | 0.060 | 9.0 |
| 5b | 3 | Me | Me | 0.0086 | 0.480 | 0.038 | 3.1 |
| 5c | 3 | Me | CV | 0.0037 | 0.015 | 0.003 | 6.4 |
| 5d | 3 | F | CV | 0.0041 | 0.150 | 0.0071 | 18.0 |
| 11a | — | Me | Me | 0.0023 | 0.047 | 0.090 | 7.0 |
| 6a | 2 | Me | Me | 0.012 | 0.700 | 0.110 | 95 |
| 6b | 3 | Me | Me | 0.0081 | 0.310 | 0.031 | 8.0 |
| 6c | 3 | Me | CN | 0.0068 | 1.0 | 0.042 | >100 |
| 6d | 3 | Me | CV[c] | 0.0012 | 0.012 | 0.0013 | 4.5 |
| 6e | 3 | F | Me | 0.00019 | 0.350 | 0.070 | 10.0 |
| 6f | 3 | F | Et | 0.0016 | 0.500 | 0.050 | 13.0 |
| 6g | 3 | F | i-Pr | 0.0022 | 0.270 | 0.030 | 1.5 |
| 6h | 3 | F | c-Pr | 0.0028 | 1.100 | 0.150 | 2.2 |
| 6i | 3 | F | CE[d] | 0.005 | 0.230 | 0.020 | 27.0 |
| 6j | 3 | F | CV | 0.014 | 0.630 | 0.046 | 6.5 |
| 12a | 2 | Me | Me | 0.024 | 1.000 | 0.042 | 4.2 |
| 12b | 3 | Me | Me | 0.024 | 1.200 | 0.140 | 4.0 |
| JLJ0596 | | | | 0.007 | 0.510 | 0.068 | 1.8 |
| JLJ0597 | | | | 0.0057 | 0.075 | 0.016 | 7.0 |
| JLJ0618 | | | | 0.003 | 0.017 | 0.002 | 4.5 |
| JLJ0619 | | | | 0.0045 | 0.470 | 0.034 | 2.2 |
| nevirapine | | | | 0.11 | NA | NA | >100 |
| efavirenz | | | | 0.002 | 0.010 | 0.030 | 15 |
| etravirine | | | | 0.001 | 0.008 | 0.005 | 11 |
| rilpivirine | | | | 0.00067 | 0.00065 | 0.002 | 8 |

[a]Results using human MT-2 cells. Antiviral and toxicity curves used triplicate samples at each concentration.
NA = not active.
[b]Compound 10a = TMC120.
[c]CV = E-cyanovinyl.
[d]CE = 2-cyanoethyl.

Appendage of the morpholinoethoxy substituent to compound 2 (R=H, R'=Me) to yield compound 2j resulted in a 9-fold reduction in wild-type potency (Table 2), while the modification of pyrimidine 10a to yield compounds 5a and 5b results in 10- to 20-fold declines. Though the compounds are still potent NNRTIs towards wild-type virus, Y181C-bearing variants had $EC_{50}$ values of 700 and 480 nM. However, compound 5b displayed impressive activity towards the challenging double mutant. The corresponding triazine 6b fared even better with $EC_{50}$ values of 8, 310, and 31 nM. Thus, these results encouraged further study of triazine analogs.

Replacement of the 4-Me substituent of the mesityl group by cyano and cyanovinyl was explored, resulting in the remarkably potent compound 6d with $EC_{50}$ results of 1, 12, and 1 nM for the wild-type and mutant HIV-1 strains. 6d may be viewed as a triazine relative of rilpivirine with a strategically added morpholinopropoxy group, having very similar activity results to those observed for etravirine. 2,6-difluorophenyl alternatives 6e-6i with various 4-R groups were also examined. However, the 4-methyl analog 6e was strikingly potent (190 pM) in the wild-type assay. Only one NNRTI with greater anti-HIV activity has been previously reported (Bollini et al., 2011, J. Med. Chem. 54:8528).

The solubility results are summarized in Table 5. Consistent with the results for compounds 2 and 3 (Table 3), the addition of the morpholinoalkoxy groups had profound effects, with 83- and 182-fold increases in S observed when going from TMC120 (10a) to compounds 5a and 5b. The aqueous solubility of the corresponding triazine 11a was also very low (0.2 μg/mL); large enhancements in solubility were again observed when using the morpholinoalkoxy analogs. Notably, 6d had a solubility of 14.2 µg/mL, which is 100-fold greater than that for dapivirine (TMC120, 10a) and 59- and 710-fold greater than the prior reports for rilpivirine.

TABLE 5

Aqueous Solubility at pH 6.5 (S)

[Structures of compounds 10 (Y = H; X = CH), 11 (Y = H; X = N), 5 (X = CH), 6 (X = N)]

| Compound | S, µg/mL |
|---|---|
| 10a | 0.15 |
| 5a | 12.5 |
| 5b | 27.3 |
| 5c | 2.0 |
| 11a | 0.20 |
| 6a | 4.42 |
| 6b | 15.3 |
| 6c | 13.3 |
| 6d | 14.2 |
| 6e | 22.9 |
| 6i | 25.4 |
| nevirapine | 167[a] |
| efavirenz | 68.0 |
| etravirine | <<1[b] |
| rilpivirine | 0.02[c], 0.24[d] |

[a]Morelock et al., 1994, J. Pharm. Sci. 83:948.
[b]Weuts et al., 2011, J. Pharm. Sci. 100:260.
[c]Janssen et al., 2005, J. Med. Chem. 48:1901, pH 7.
[d]Sun et al., 2012, Bioorg. Med. Chem. Lett. 22:2376, pH 7.4.

Crystallographic Studies

Figure 11:
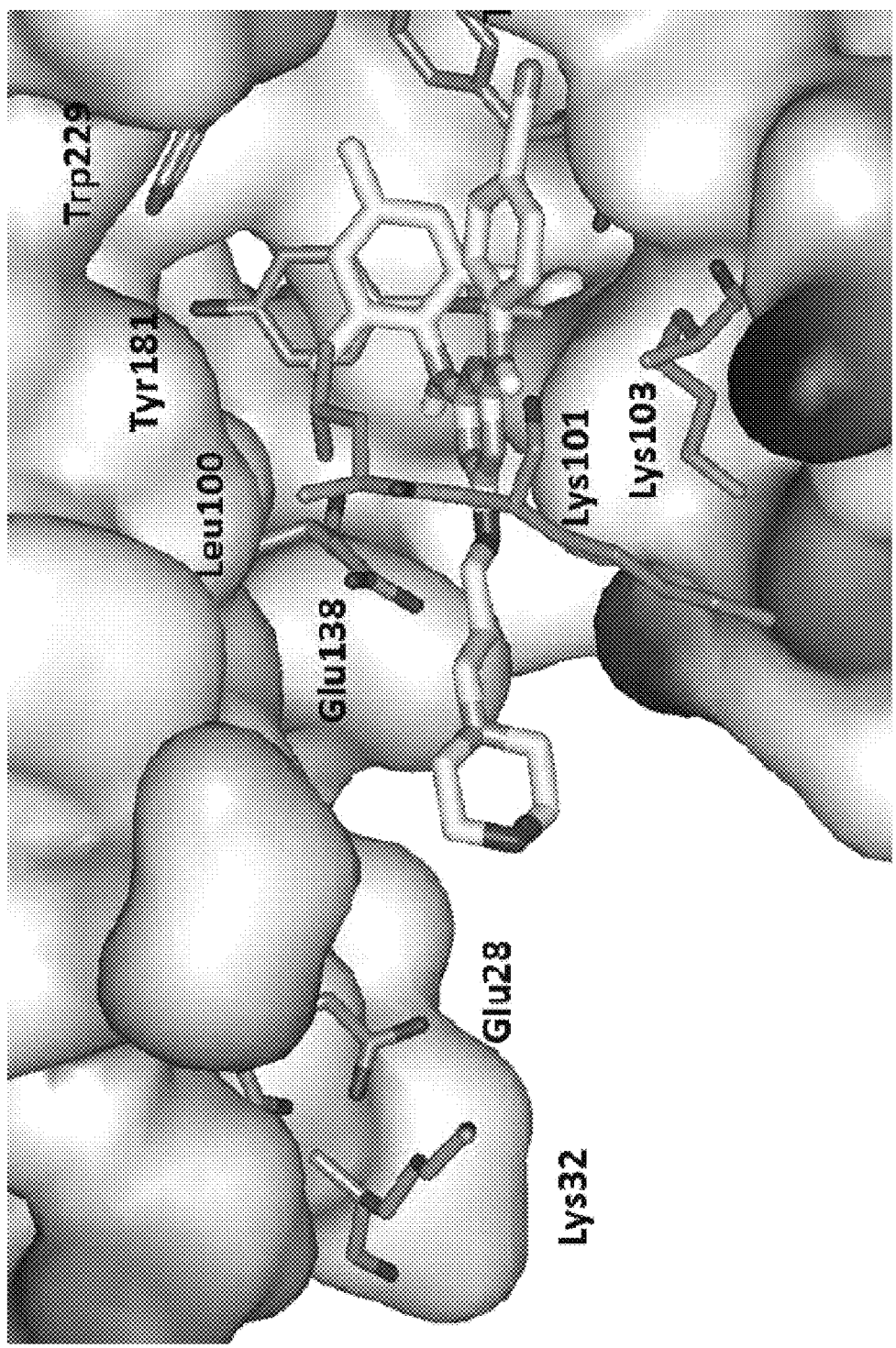
FIG. 11 is an image illustrating the computed structure for the complex of compound 6b with wild-type HIV-1 reverse transcriptase. Carbon atoms of compound 6b are in yellow. Some protein residues have been removed for clarity.
Figure 12:
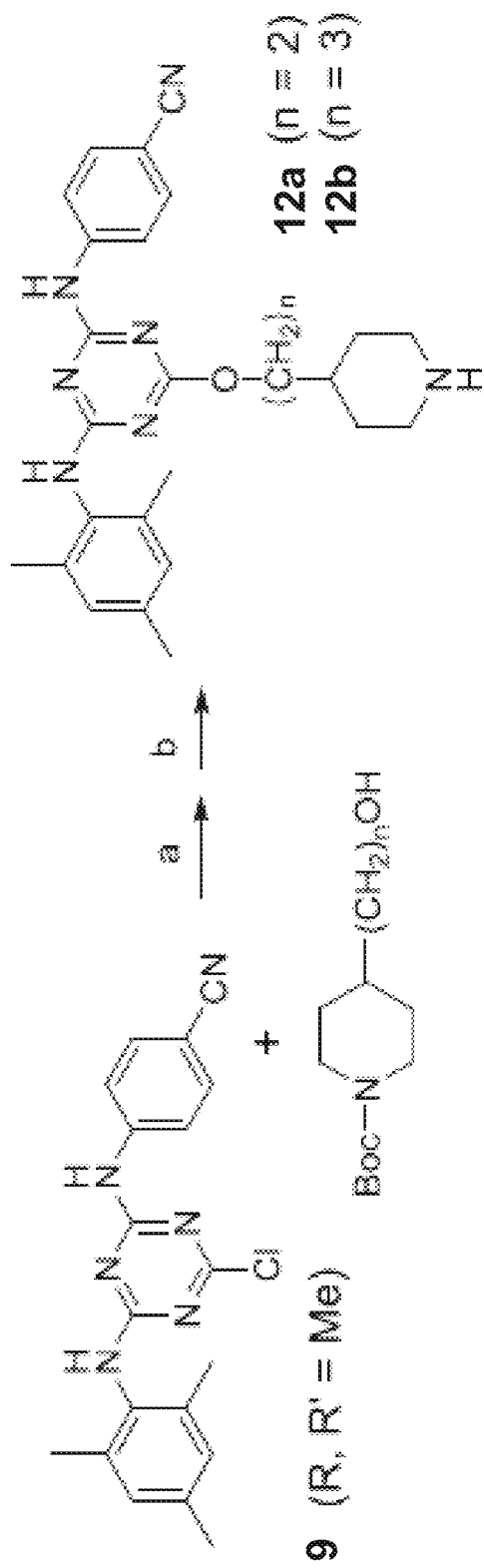
FIG. 12 is a synthetic scheme illustrating an exemplary synthesis of compounds 12a and 12b. Reagents: (a) NaH, ACN, 70° C., overnight; (b) TFA, DCM, 0° C. to rt, 15 min.
Figure 13:
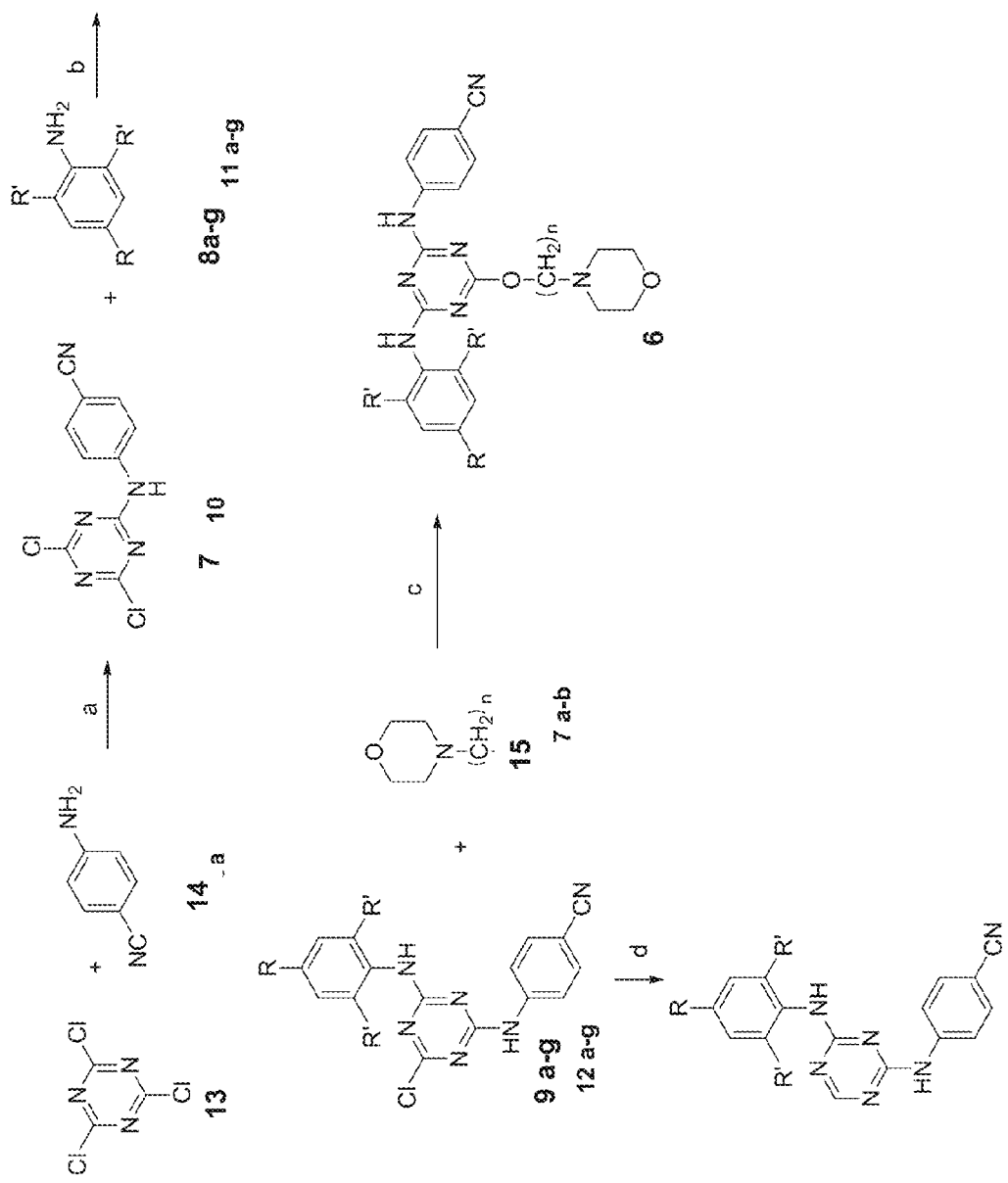
FIG. 13 is a synthetic scheme illustrating an exemplary synthesis of compound JLJ527 (reference compound 11a). Reagents: (a) DIPEA, THF, rt, overnight; (b) DIPEA, THF, 65° C., 2 days; (c) NaH, THF, rt, overnight; (d) $H_2$/Pd—C.

As demonstrated crystallographically for compound 3, the morpholinoalkoxy side chains for the present compounds in complex with HIV-1 reverse transcriptase may extend past Glu138 into the entrance channel of the NNRTI binding site (Example 1). An illustration for 6b is provided in FIG. 11, as created by modeling with the BOMB and MCPRO programs using previously described methods (Jorgensen, 2009, Acc. Chem. Res. 42:724; Jorgensen and Tirado-Rives, 2005, J. Comput. Chem. 26:1689) using the OPLS/CM1A force field (Jorgensen and Tirado-Rives, 2005, Proc. Natl. Acad. Sci. USA 103:6665) starting with the 1S9E crystal structure, which has an anilinyltriazine as the ligand (Das et al., 2004, J. Med. Chem. 47:2550). Consistent with the modeling and crystallography for compound 3 (Example 1), the contacts in the NNRTI binding site are normal and the morpholinopropoxy side chain extends past Glu138 towards Glu28. A salt bridge, which is sometimes observed between Glu138 and Lys101, cannot be present to allow the passage. If Glu28 reoriented, it could be in close contact with the morpholine terminus. Although not wishing to be bound by any particular theory, this result suggested the possible benefit of replacing the ether oxygen with a positively charged group. Thus, the piperidine analogs 12a and 12b were synthesized (FIG. 12). However, these compounds were observed to be less potent than the corresponding morpholine analogs 6a and 6b (Table 4). The intended salt-bridge is largely solvent-exposed and in competition with the Glu28-Lys32 interaction.

Example 3: Exemplary Procedure for the Synthesis of Compound 6

Compound 7 (0.34 g, 1.2 mmol) was dissolved in anhydrous THF (10 mL), following by addition of the corresponding aniline 8 (1.2 mmol) and DIPEA (0.18 g, 1.44 mmol). The reaction mixture was stirred at room temperature or refluxed overnight. THF was removed under pressure; the crude was purified on silica gel to yield the corresponding compound 9. Then, to a solution of the hydroxyalkyl-morpholine (12.8 mmol) in anhydrous THF, NaH (95%, 7.1 mmol) was added in portions at 0° C. After 30 min, a solution of compound 9 in dioxane was added dropwise and stirred at room temperature or at 80° C. overnight. The solvent was then removed under pressure; the crude was purified on silica gel to yield the target compound 6d (FIG. 10).

Compound 6d: $^1$H NMR (500 MHz, CDCl$_3$) δ 7.81-7.58 (m, 2H), 7.42 (t, J=24.0 Hz, 4H), 7.17 (s, 1H), 6.73 (s, 1H), 5.91 (d, J=16.8 Hz, 1H), 4.42 (s, 2H), 4.22 (s, 1H), 3.72 (s, 4H), 2.46 (t, J=33.9 Hz, 6H), 2.29 (d, J=9.2 Hz, 6H), 1.98 (s, 2H). $^{13}$C NMR (101 MHz, DMSO) δ 173.77, 166.10, 150.29, 143.64, 136.48, 132.60, 127.27, 119.45, 118.47, 66.17, 64.45, 55.21, 53.33, 48.58, 40.12, 39.91, 39.70, 39.49, 38.86, 18.24. HR-MS (ES) calculated for $C_{28}H_{30}N_8O_2$ [M+1]$^+$ 511.0009. found 511.0011.

Example 4: Chemical Synthetic Procedures for Compounds

General Information

NMR spectra were recorded on a Bruker Avance DRX-500 (500 MHz) and DRX-400 (400 MHz) instruments. Column chromatography was carried out using CombiFlash over redisep column cartridges employing Merck silica gel (Kieselgel 60, 63-200 µm). Precoated silica gel plates F-254 were used for thin-layer analytical chromatography. Mass determination was performed using Waters Xevo QTOF equipped with Z-spray electrospray ionization source. The purity (≥95%) of final synthesized compound was determined by reverse phase HPLC, using a Waters 2487 dual λ absorbance detector with a Waters 1525 binary pump and a Phenomenex Luna 5µ C18(2) 250×4.6 mm column. Sample was run at 1 mL/min using gradient mixtures of 5-100% of water with 0.1% trifluoroacetic acid (TFA) (A) and 10:1 acetonitrile:water with 0.1% TFA (B) for 22 min followed by 3 min at 100% B.

For measurement of aqueous solubility, the pH of the buffer solutions was measured by Corning Combination pH Electrodes (4136L21) pH meter with Ag/AgCl glass electrode. The temperature of the samples was maintained at 25° C. during the solubility measurements. An Ika® RCT basic magnetic stirrer was used to mix the two phases. Samples were filtered using a syringeless filter device Mini-Uniprep (0.45 μm pore size). The concentration in the supernatant of the samples was measured spectrophotometrically using Agilent 8453 UV-Vis spectrophotometer.

Synthesis of 4-((4,6-dichloro-1,3,5-triazin-2-yl) amino)benzonitrile (intermediate 7)

To a mixture of cyanuric chloride 13 (1.5 g, 8.2 mmol) and 4-aminobenzonitrile 14 (0.96 g, 8.2 mmol) in anhydrous THF (10 mL) at 0° C. was slowly added DIPEA (1.25 g, 9.84 mmol). The resulting mixture was stirred at room temperature for 3 h. The solvent was removed under pressure; the crude was purified on silica gel to yield 7 as a white solid. Yield 1.2 g, 57%. $^1$H NMR (400 MHz, DMSO) δ 11.02 (s, 1H), 7.98 (d, J=8.8 Hz, 2H), 7.93 (d, J=8.8 Hz, 2H).

General Procedure for the Synthesis of Compounds 9a-9j

Intermediate 7 (0.34 g, 1.2 mmol) was dissolved in anhydrous THF (10 mL), following by addition of the corresponding aniline 8a-g (1.2 mmol) and DIPEA (0.18 g, 1.44 mmol). The reaction mixture was stirred at room temperature or reflux overnight. THF was removed under pressure; the crude was purified on silica gel to afford the corresponding compounds 9a-9g.

4-((4-chloro-6-(mesitylamino)-1,3,5-triazin-2-yl) amino)benzonitrile (9a or 9b)

white powder, yield: 52%. $^1$H NMR (500 MHz, DMSO) δ 10.76 (s, 1H), 10.14 (s, 1H), 8.09 (d, J=8.6 Hz, 1H), 7.83 (d, 8.8 Hz, 2H), 7.57 (s, 1H), 6.99 (d, J=2.09 Hz, 1H), 2.16 (s, 9H). LC-MS (ES) for $C_{19}H_{17}ClN_6$ [M+1]$^+$ 365.24

4-((4-chloro-6-((4-cyanophenyl)amino)-1,3,5-triazin-2-yl)amino)-3,5-dimethylbenzonitrile (9c)

white powder, yield: 42%. $^1$H NMR (400 MHz, DMSO) δ 10.22 (s, 1H), 10.01 (s, 1H), 8.21 (d, J=2.0 Hz, 2H), 7.51 (d, J=8.0 Hz, 2H), 7.01 (m, 2H), 2.22 (s, 3H). LC-MS (ES) for $C_{19}H_{14}ClN_7$ [M+1]$^+$ 376.21.

(E)-4-((4-chloro-6-((4-(2-cyanovinyl)-2,6-dimethylphenyl)amino)-1,3,5-triazin-2-yl)amino)benzonitrile (9d)

4-((4-chloro-6-((4-methyl-2,6-fluorophenyl)amino)-1,3,5-triazin-2-yl)amino)benzonitrile (9e)

white powder, yield: 65%. $^1$H NMR (400 MHz, DMSO) δ 10.59 (s, 1H), 9.73 (s, 1H), 8.09 (d, J=8.0 Hz, 2H), 7.86 (d, J=8.9 Hz, 1H), 7.74 (m, 2H), 7.02 (d, J=22.1 Hz, 2H), 2.50 (s, 3H). LC-MS (ES) for $C_{17}H_{11}ClF_2N_6$ [M+1]$^+$ 373.99

4-((4-chloro-6-((4-ethyl-2,6-fluorophenyl)amino)-1,3,5-triazin-2-yl)amino)benzonitrile (9f)

white powder, yield: 77%. $^1$H NMR (400 MHz, DMSO) δ 10.22 (s, 1H), 9.47 (s, 1H), 8.22-7.45 (m, 4H), 7.36-7.04 (m, 2H), 1.99 (t, J=21.5 Hz, 2H), 1.27 (dd, J=15.7, 8.3 Hz, 3H). LC-MS (ES) for $C_{18}H_{13}ClF_2N_6$ [M+1]$^+$ 387.91

4-((4-chloro-6-((4-isopropyl-2,6-fluorophenyl) amino)-1,3,5-triazin-2-yl)amino)benzonitrile (9g)

white powder, yield: 70%. $^1$H NMR (400 MHz, DMSO) δ 10.00 (s, 1H), 9.70 (s, 1H), 8.1 (d, J=8.0 Hz, 2H), 7.49 (m, 2H), 7.13 (m, 2H), 2.82 (m, 1H), 1.15 (dd, J=20.2, 7.0 Hz, 6H). LC-MS (ES) for $C_{19}H_{15}ClF_2N_6$ [M+1]$^+$ 401.10

4-((4-chloro-6-((4-cyclopropyl-2,6-difluorophenyl) amino)-1,3,5-triazin-2-yl)amino)benzonitrile (9h)

white powder, yield: 84%. $^1$H NMR (400 MHz, DMSO) δ 10.76 (s, 1H), 10.14 (s, 1H), 8.22-7.80 (m, 2H), 7.66 (d, 8.8 Hz, 2H), 7.06 (dd, J=2.04, 8.7 Hz, 2H), 3.93 (s, 1H), 1.12 (d, J=7.8 Hz, 2H), 0.86 (s, 2H). LC-MS (ES) for $C_{19}H_{15}ClF_2N_6$ [M+1]$^+$ 399.00

4-((4-chloro-6-((4-(2-cyanoethyl)-2,6-difluorophenyl)amino)-1,3,5-triazin-2-yl)amino)benzonitrile (9i)

E)-4-((4-chloro-6-((4-(2-cyanovinyl)-2,6-difluorophenyl)amino)-1,3,5-triazin-2-yl)amino)benzonitrile (9j)

white powder, yield: 12%. $^1$H NMR (400 MHz, CDCl$_3$) δ 7.19 (d, J=16.5 Hz, 1H), 7.18-7.07 (m, 3H), 6.95 (dd, J=7.0, 2.1 Hz, 1H), 5.65 (d, J=16.5 Hz, 1H), 4.27 (1H, s), 4.09 (1H, s). LC-MS (ES) for $C_{19}H_{10}ClF_2N_7$ [M+1]$^+$ 409.21.

General Procedure for the Synthesis of Compounds 6a-6j

To a solution of 4-(3-hydroxypropyl) or (3-hydroxyethyl) morpholine (12.8 mmol) in anhydrous THF, NaH (95%, 7.1 mmol) was added in portions at 0° C. After 30 min, a solution of compound 9a-9j in dioxane was added dropwise and stirred at room temperature or at 80° C. overnight. After this period, the solvent was removed under pressure; the crude was purified on silica gel to give the targets compounds.

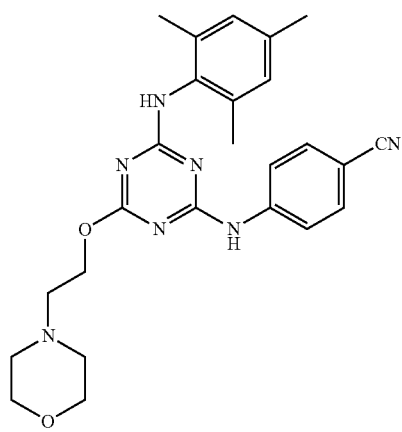 [SMILES: Cc1cc(C)c(Nc2nc(Nc3ccc(C#N)cc3)nc(OCCN3CCOCC3)n2)c(C)c1]

Compound 6a: $^1$H NMR (500 MHz, DMSO) δ 8.09 (d, J=8.6 Hz, 1H), 7.80 (d, J=8.8 Hz, 1H), 7.78 (s, 1H), 7.57 (s, 1H), 6.99 (d, J=20.9 Hz, 2H), 4.50 (t, J=5.7 Hz, 1H), 4.26 (t, J=6.1 Hz, 1H), 4.09 (q, J=7.1 Hz, 1H), 3.65-3.62 (m, 2H), 3.60-3.49 (m, 2H), 2.73 (dd, J=17.2, 11.5 Hz, 2H), 2.54 (s, 2H), 2.35 (s, 3H), 2.30 (s, 1H), 2.16 (d, J=9.9 Hz, 6H). $^{13}$C NMR (101 MHz, DMSO) δ 170.24, 166.31, 144.32, 135.64, 135.43, 132.91, 132.56, 128.38, 128.27, 119.41, 119.32, 103.23, 103.08, 66.19, 66.07, 63.67, 62.92, 56.78, 56.47, 53.56, 53.35, 20.52, 18.13. HR-MS (ES) calcd for $C_{25}H_{29}N_7O_2[M+1]^+$ 460.2249. found 459.2251.

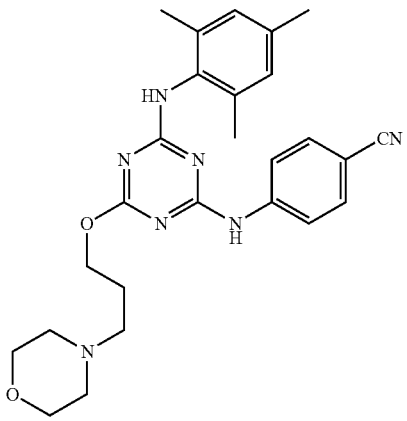 [SMILES: Cc1cc(C)c(Nc2nc(Nc3ccc(C#N)cc3)nc(OCCCN3CCOCC3)n2)c(C)c1]

Compound 6b: $^1$H NMR (400 MHz, DMSO) δ 8.17 (d, J=8.3 Hz, 1H), 7.87 (d, J=7.5 Hz, 1H), 7.83-7.73 (m, 1H), 7.64 (s, 1H), 7.05 (d, J=16.7 Hz, 2H), 4.47 (s, 2H), 4.26 (s, 1H), 3.70 (s, 3H), 3.65 (s, 2H), 3.53 (s, 1H), 2.59-2.44 (m, 3H), 2.39 (d, J=14.9 Hz, 5H), 2.23 (s, 6H). $^{13}$C NMR (126 MHz, DMSO) δ 170.29, 166.32, 144.38, 135.57, 135.39, 132.83, 128.31, 119.37, 119.26, 119.13, 103.00, 66.14, 66.02, 65.99, 64.78, 54.79, 54.70, 53.29, 53.17, 46.01, 41.16, 25.46, 25.29, 20.94, 20.46, 18.06. HR-MS (ES) calcd for $C_{26}H_{31}N_7O_2[M+1]^+$ 474.3321. found 474.3327.

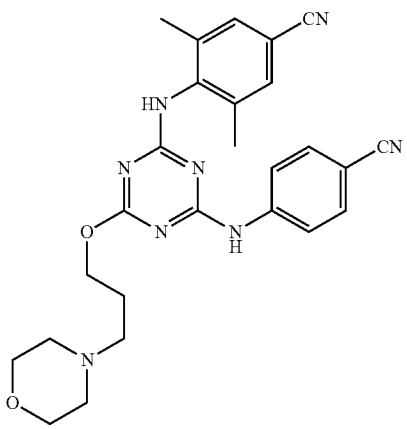 [SMILES: Cc1cc(C#N)cc(C)c1Nc1nc(Nc2ccc(C#N)cc2)nc(OCCCN2CCOCC2)n1]

Compound 6c: $^1$NMR (400 MHz, DMSO) δ 9.45 (s, 1H), 8.03 (s, 1H), 7.76 (s, 2H), 7.70-7.53 (m, 4H), 4.37 (s, 2H), 4.06 (dd, J=28.1, 21.1 Hz, 1H), 3.56 (d, J=18.9 Hz, 4H), 2.38 (dd, J=51.2, 29.4 Hz, 7H), 2.21 (s, 6H), 1.90 (s, 1H), 1.74 (s, 1H). $^{13}$C NMR (101 MHz, DMSO) δ 170.97, 167.11, 165.58, 159.82, 157.42, 150.28, 144.44, 133.04, 120.03, 112.72, 110.31, 103.98, 66.66, 65.59, 55.23, 53.79, 40.61, 40.40, 40.19, 39.98, 39.77, 39.57, 39.36, 33.71, 25.88, 23.87. HR-MS (ES) calcd for $C_{26}H_{28}N_8O_2$ $[M+1]^+$ 483.6623. found 483.6625.

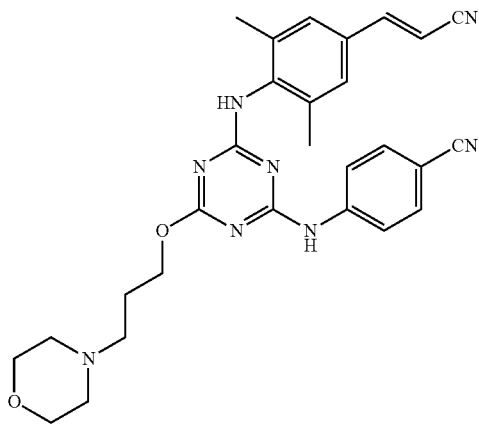 [SMILES: Cc1cc(/C=C/C#N)cc(C)c1Nc1nc(Nc2ccc(C#N)cc2)nc(OCCCN2CCOCC2)n1]

Compound 6d: $^1$H NMR (500 MHz, CDCl$_3$) δ 7.81-7.58 (m, 2H), 7.42 (t, J=24.0 Hz, 4H), 7.17 (s, 1H), 6.73 (s, 1H), 5.91 (d, J=16.8 Hz, 1H), 4.42 (s, 2H), 4.22 (s, 1H), 3.72 (s, 4H), 2.46 (t, J=33.9 Hz, 6H), 2.29 (d, J=9.2 Hz, 6H), 1.98 (s, 2H). $^{13}$C NMR (101 MHz, DMSO) δ 173.77, 166.10, 150.29, 143.64, 136.48, 132.60, 127.27, 119.45, 118.47, 66.17, 64.45, 55.21, 53.33, 48.58, 40.12, 39.91, 39.70, 39.49, 38.86, 18.24. HR-MS (ES) calcd for $C_{28}H_{30}N_8O_2$ $[M+1]^+$ 511.0009. found 511.0011.

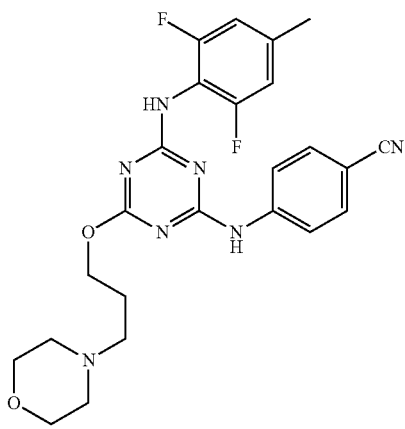 [SMILES: Cc1cc(F)c(Nc2nc(Nc3ccc(C#N)cc3)nc(OCCCN3CCOCC3)n2)c(F)c1]

Compound 6e: $^1$H NMR (400 MHz, DMSO) δ 8.15 (s, 1H), 7.80 (d, J=58.1 Hz, 3H), 7.20 (s, 2H), 4.40 (d, J=65.9 Hz, 2H), 3.69 (s, 4H), 3.30 (d, J=5.3 Hz, 1H), 2.50 (s, 7H), 2.01 (s, 3H). $^{13}$C NMR (126 MHz, DMSO) δ 170.53, 170.29, 166.32, 165.22, 164.96, 144.38, 144.31, 135.57, 132.91, 132.63, 132.48, 128.31, 119.37, 119.13, 103.16, 66.09, 64.78, 53.29, 46.01, 41.16, 25.29, 20.94, 20.46, 18.06. HR-MS (ES) calcd for $C_{24}H_{25}F_2N_7O_2$ $[M+1]^+$ 482.2201. found 482.2200.

57

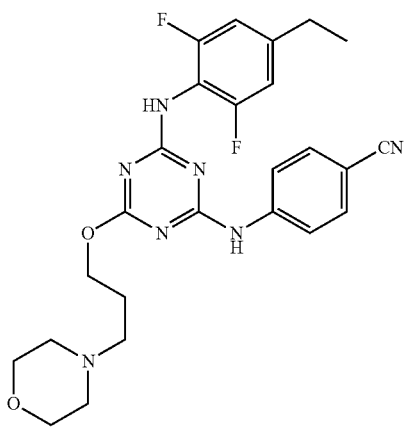 [SMILES: CCc1cc(F)c(Nc2nc(Nc3ccc(C#N)cc3)nc(OCCCN3CCOCC3)n2)c(F)c1]

Compound 6f: ¹H NMR (400 MHz, DMSO) δ 9.47 (s, 1H), 8.10 (s, 1H), 7.72 (d, J=70.2 Hz, 4H), 7.12 (d, J=37.6 Hz, 2H), 4.34 (d, J=63.4 Hz, 3H), 3.62 (s, 5H), 2.73 (s, 2H), 2.42 (s, 4H), 1.96 (d, J=10.9 Hz, 2H), 1.27 (dd, J=15.7, 8.3 Hz, 3H). ¹³C NMR (126 MHz, DMSO) δ 171.12, 171.00, 165.25, 159.38, 151.21, 135.78, 119.65, 117.97, 113.1, 108.67, 67.89, 66.78, 65.92, 58.90, 54.02, 53.56, 27.7, 18.16, 14.50. HR-MS (ES) calcd for $C_{25}H_{27}F_2N_7O_2$ $[M+1]^+$ 496.1698. found 496.1670.

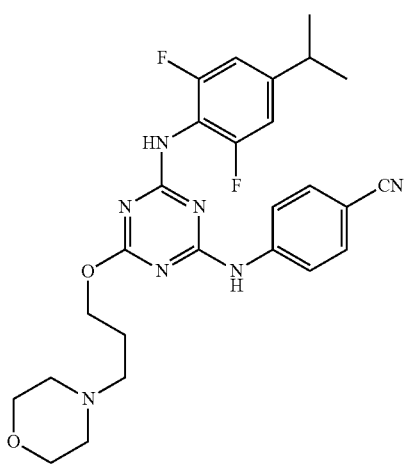 [SMILES: CC(C)c1cc(F)c(Nc2nc(Nc3ccc(C#N)cc3)nc(OCCCN3CCOCC3)n2)c(F)c1]

Compound 6g: ¹H NMR (400 MHz, DMSO) δ 10.09 (s, 1H), 9.40 (s, 1H), 8.04 (s, 1H), 7.63 (d, J=61.2 Hz, 3H), 7.13 (s, 2H), 4.28 (d, J=58.7 Hz, 2H), 3.56 (s, 4H), 2.97 (s, 1H), 2.35 (s, 6H), 1.94 (d, J=43.6 Hz, 2H), 1.21 (dd, J=20.2, 7.0 Hz, 6H). ¹³C NMR (126 MHz, DMSO) δ 171.23, 166.00, 164.27, 159.32, 146.65, 144.30, 132.61, 120.50, 110.62, 109.46, 101.22 66.10, 65.03, 59.68, 54.69, 53.23, 28.33, 33.21, 23.32. HR-MS (ES) calcd for $C_{26}H_{29}F_2N_7O_2$ $[M+1]^+$ 510.0013. found 510.0014.

58

Compound 6h: ¹H NMR (400 MHz, DMSO) δ 10.17 (s, 1H), 9.44 (s, 1H), 8.18-7.53 (m, 4H), 7.05 (s, 2H), 4.35 (d, J=65.0 Hz, 2H), 3.65 (d, J=5.2 Hz, 3H), 2.44 (s, 5H), 2.07 (t, J=41.4 Hz, 3H), 1.33 (s, 1H), 1.11 (s, 2H), 0.97-0.92 (m, 1H), 0.87 (s, 2H). ¹³C NMR (126 MHz, DMSO) δ 170.44, 166.84, 165.07, 157.32, 145.63, 143.29, 132.61, 119.48, 108.62, 103.46, 103.17, 66.10, 65.03, 59.68, 54.69, 53.23, 25.33, 20.68, 15.00, 14.01, 10.15. HR-MS (ES) calcd for $C_{26}H_{27}F_2N_7O_2$ $[M+1]^+$ 508.2123. found 508.2120.

Compound 6i: ¹H NMR (500 MHz, CDCl₃) δ 7.59 (m, 4H), 7.37 (s, 1H), 6.93 (d, J=8.0 Hz, 2H), 6.73 (s, 1H), 4.38 (s, 2H), 3.75-3.67 (m, 4H), 3.00 (t, J=7.0 Hz, 2H), 2.70 (t, J=7.1 Hz, 2H), 2.50-2.43 (m, 4H), 1.94 (dd, J=17.4, 11.0 Hz, 4H). ¹³C NMR (101 MHz, DMSO) δ 174.46, 166.10, 150.29, 146.95, 144.33, 136.48, 132.60, 127.27, 119.45, 95.63, 77.37, 66.17, 64.15, 54.84, 53.33, 48.58, 40.64, 40.12, 39.91, 39.70, 39.49, 39.28, 39.07, 38.86, 18.24. HR-MS (ES) calcd for $C_{26}H_{26}F_2N_8O_2$ $[M+1]^+$ 521.5409. found 521.5411.

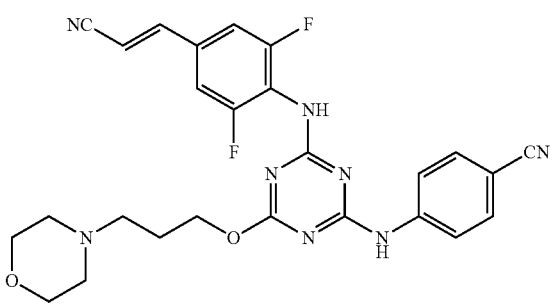

Compound 6j (JLJ0562) ((E)-4-((4-((4-(2-cyanovinyl)-2,6-difluorophenyl)amino)-6-(3-morpholinopropoxy)-1,3,5-triazin-2-yl)amino)benzonitrile) may be prepared using compound 9j.

Solubility Assay

The equilibrium solubility of the non-ionized form of the samples was determined by the shake flask method. For each reported solubility result, two or three independent shake-flask experiments were carried out in parallel. For each experiment the 5 mg of the solid was added to 5 mL of the buffer in a vial. The solution containing solid excess of the sample was stirred for 48 h at 25° C. before separating saturated solution and precipitate by filtration. For the quantitative determination methanol: Buffer BR (1:1) is used to dilute the filtrate (1.5×, 2×, 5×, 10×) normally all of these dilutions fall into the lineal range of the calibration curve. For the calibration curve 1 mg/mL of each compound was diluted with methanol: Buffer BR (1:1) (100 μg/mL, 50 μg/mL, 25 μg/mL, 12.5 μg/mL, 6.25 μg/mL, 1.5 μg/mL, 0.39 μg/mL, 0.09 μg/mL, 0.025 μg/mL). The standards and samples were measured by UV spectrophotometry at the maximum wavelength of the individual compounds.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising at least one pharmaceutically acceptable carrier and at least one compound of formula (I):

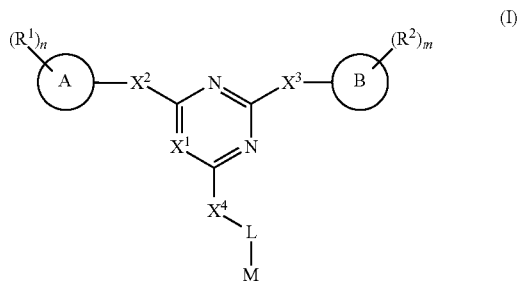

wherein in formula (I):
ring A and ring B are each independently aryl;
each occurrence of $R^1$, and $R^2$ is independently selected from the group consisting of H, —$C_1$-$C_6$ alkyl, —$C_3$-$C_6$ cycloalkyl, —$C_2$-$C_6$ alkenyl, —F, —Cl, —CN, 2-cyanoethyl, and 2-cyanovinyl, wherein the alkyl, cycloalkyl, and alkenyl groups are optionally substituted;
$X^1$ is CH or N;
$X^2$ and $X^3$ are each —NH—;
$X^4$ is —O—;
L is —$(CH_2)_y$—, wherein one or more —$CH_2$— groups in L are independently and optionally replaced with —O—,
with the provisos that: no heteroatom-heteroatom bond exist within L, and L is not covalently linked to $X^4$ or M through a heteroatom-heteroatom bond;
M is morpholinyl, piperidinyl, piperazinyl, tetrahydropyranyl or imidazolyl, wherein the morpholinyl, piperidinyl, piperazinyl, tetrahydropyranyl or imidazolyl is independently optionally substituted;
m and n are each independently an integer from 0-5; and,
y is an integer from 0-19,
a salt, solvate, or N-oxide thereof.

2. The composition of claim 1, wherein L is selected from the group consisting of —$(CH_2)_2$—, —$(CH_2)_3$—, —$(CH_2)_2(OCH_2CH_2)$—, —$(CH_2)_2(OCH_2CH_2)_2$—, —$(CH_2)_2(OCH_2CH_2)_3$—, and —$(CH_2)_2(OCH_2CH_2)_5$—.

3. The composition of claim 2, wherein L is —$(CH_2)_3$—.

4. The composition of claim 1, wherein M is selected from the group consisting of morpholin-4-yl, imidazol-1-yl, piperidin-1-yl, piperidin-4-yl, tetrahydropyranyl, piperizin-1-yl or 4-methyl-piperizin-1-yl.

5. The composition of claim 1, wherein the at least one compound of formula (I) is a compound of formula (II):

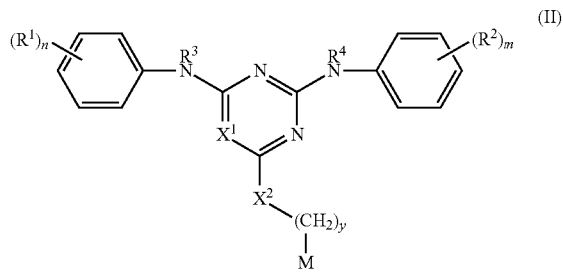

wherein in formula (II):
each occurrence of $R^1$ and $R^2$ is independently selected from the group consisting of H, —$C_1$-$C_6$ alkyl, —$C_3$-$C_6$ cycloalkyl, —$C_2$-$C_6$ alkenyl, —F, —Cl, —CN, 2-cyanoethyl, and 2-cyanovinyl, wherein the alkyl, cycloalkyl, and alkenyl groups are optionally substituted;
$R^3$, and $R^4$ are each hydrogen;
$X^1$ is CH or N;
$X^2$ is —O—;
M is morpholinyl, piperidinyl, piperazinyl, tetrahydropyranyl or imidazolyl, wherein the morpholinyl, piperidinyl, piperazinyl, tetrahydropyranyl or imidazolyl is independently optionally substituted;
m and n are each independently an integer from 0-5; and,
y is an integer from 1-5,
a salt, solvate, or N-oxide thereof.

6. The composition of claim 1, wherein the compound is at least one selected from the group consisting of 4-((4-(mesitylamino)-6-(2-morpholinoethoxy) pyrimidin-2-yl)amino)benzonitrile, 4-((4-(mesitylamino)-6-(3-morpholinopropoxy) pyrimidin-2-yl)amino)benzonitrile, 4-((4-

(mesitylamino)-6-(2-morpholinoethoxy)-1,3,5-triazin-2-yl) amino)benzonitrile, 4-((4-(mesitylamino)-6-(3-morpholinopropoxy)-1,3,5-triazin-2-yl)amino)benzonitrile, 4-((4-((4-cyanophenyl)amino)-6-(3-morpholino propoxy)-1,3,5-triazin-2-yl)amino)-3,5-dimethylbenzonitrile, (E)-4-((4-((4-(2-cyanovinyl)-2,6-dimethylphenyl)amino)-6-(3-morpholinopropoxy)-1,3,5-triazin-2-yl)amino)benzonitrile, 4-((4-((2,6-difluoro-4-methylphenyl)amino)-6-(3-morpholino propoxy)-1,3,5-triazin-2-yl)amino)benzonitrile, 4-((4-((4-ethyl-2,6-difluorophenyl)amino)-6-(3-morpholinopropoxy)-1,3,5-triazin-2-yl)amino)benzonitrile, 4-((4-((2,6-difluoro-4-isopropylphenyl)amino)-6-(3-morpholinopropoxy)-1,3,5-triazin-2-yl)amino) benzonitrile, 4-((4-((4-cyclopropyl-2,6-difluorophenyl)amino)-6-(3-morpholinopropoxy)-1,3,5-triazin-2-yl)amino)benzonitrile, 4-((4-((4-(2-cyanoethyl)-2,6-difluorophenyl)amino)-6-(3-morpholinopropoxy)-1,3,5-triazin-2-yl)amino)benzonitrile, 4-((4-(mesitylamino)-6-(2-(piperidin-4-yl)ethoxy)-1,3,5-triazin-2-yl)amino)benzonitrile, 4-((4-(mesitylamino)-6-(3-(piperidin-4-yl)propoxy)-1,3,5-triazin-2-yl)amino)benzonitrile, (E)-4-((4-((4-(2-cyanovinyl)-2,6-difluorophenyl) amino)-6-(3-morpholinopropoxy)-1,3,5-triazin-2-yl)amino) benzonitrile, (E)-4-((4-((4-(2-cyanovinyl)-2,6-dimethylphenyl) amino)-6-((3-morpholinopropyl)amino)-1, 3,5-triazin-2-yl)amino)benzonitrile, (E)-4-((4-((4-(2-cyanovinyl)-2,6-difluorophenyl)amino)-6-((3-morpholinopropyl)amino)-1,3,5-triazin-2-yl)amino) benzonitrile, (E)-4-((4-((4-(2-cyanovinyl)-2,6-dimethylphenyl) amino)-6-(3-morpholinopropoxy) pyrimidin-2-yl)amino)benzonitrile, (E)-4-((4-((4-(2-cyanovinyl)-2,6-difluorophenyl)amino)-6-(3-morpholinopropoxy)pyrimidin-2-yl)amino) benzonitrile, (E)-4-((4-((4-(2-cyanovinyl)-2,6-dimethylphenyl)amino)-6-((3-morpholinopropyl)amino)pyrimidin-2-yl)amino)benzonitrile, (E)-4-((4-((4-(2-cyanovinyl)-2,6-difluorophenyl) amino)-6-((3-morpholinopropyl)amino)pyrimidin-2-yl) amino)benzonitrile, and a salt thereof.

7. The composition of claim 1, further comprising at least one additional therapeutic agent.

8. The composition of claim 7, wherein the at least one additional therapeutic is at least one selected from the group consisting of nevirapine, delavirdine, efavirenz, etravirine, rilpivirine, and a salt thereof.

9. A method of treating an HIV-1 infection or for the prophylaxis of HIV infection in a subject in need thereof, the method comprising administering to the subject a therapeutically effective amount of a pharmaceutical composition comprising at least one compound of formula (I):

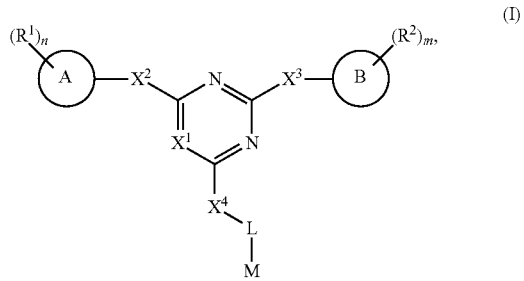

(I)

wherein in (I):
ring A and ring B are each independently aryl;
each occurrence of $R^1$, and $R^2$ is independently selected from the group consisting of H, —$C_1$-$C_6$ alkyl, —$C_3$-$C_6$ cycloalkyl, —$C_2$-$C_6$ alkenyl, F, —Cl, —CN, 2-cyanoethyl, and 2-cyanovinyl, wherein the alkyl, cycloalkyl, and alkenyl groups are optionally substituted;
$X^1$ is CH or N;
$X^2$, and $X^3$ are each —NH—
$X^4$ is —O—;
L is —$(CH_2)_y$—, wherein one or more —$CH_2$— groups in L are independently and optionally replaced with —O—,
with the provisos that: no heteroatom-heteroatom bond exist within L, and L is not covalently linked to $X^4$ or M through a heteroatom-heteroatom bond;
M is morpholinyl, piperidinyl, piperazinyl, tetrahydropyranyl or imidazolyl, wherein the morpholinyl, piperidinyl, piperazinyl, tetrahydropyranyl or imidazolyl is independently optionally substituted;
m and n are each independently an integer from 0-5; and, y is an integer from 0-19,
a salt, solvate, or N-oxide thereof.

10. The method of claim 9, wherein the at least one compound of formula (I) is a compound of formula (II):

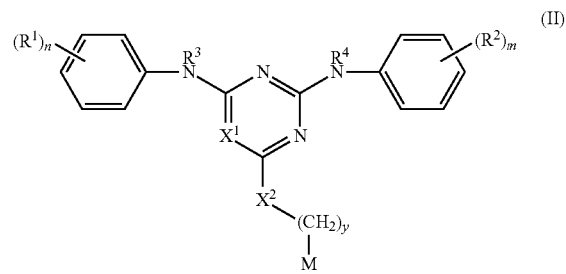

(II)

wherein in formula (II):
each occurrence of $R^1$ and $R^2$ is independently selected from the group consisting of H, —$C_1$-$C_6$ alkyl, —$C_3$-$C_6$ cycloalkyl, —$C_2$-$C_6$ alkenyl, —F, —Cl, —CN, 2-cyanoethyl, and 2-cyanovinyl, wherein the alkyl, cycloalkyl, and alkenyl groups are optionally substituted;
$R^3$, and $R^4$, are each hydrogen;
$X^1$ is CH or N;
$X^2$ is —O—;
M is morpholinyl, piperidinyl, piperazinyl, tetrahydropyranyl or imidazolyl, wherein the morpholinyl, piperidinyl, piperazinyl, tetrahydropyranyl or imidazolyl is independently optionally substituted;
m and n are each independently an integer from 0-5; and, y is an integer from 1-5,
a salt, solvate, or N-oxide thereof.

11. The method of claim 9, wherein M is selected from the group consisting of morpholin-4-yl, imidazol-1-yl, piperidin-1-yl, piperidin-4-yl, tetrahydropyranyl, piperizin-1-yl or 4-methyl-piperizin-1-yl.

12. The method of claim 9, wherein the compound is at least one selected from the group consisting of 4-((4-(mesitylamino)-6-(2-morpholinoethoxy) pyrimidin-2-yl) amino)benzonitrile, 4-((4-(mesitylamino)-6-(3-morpholinopropoxy) pyrimidin-2-yl)amino)benzonitrile, 4-((4-(mesitylamino)-6-(2-morpholinoethoxy)-1,3,5-triazin-2-yl) amino)benzonitrile, 4-((4-(mesitylamino)-6-(3-morpholinopropoxy)-1,3,5-triazin-2-yl)amino)benzonitrile, 4-((4-((4-cyanophenyl)amino)-6-(3-morpholino propoxy)-1,3,5-triazin-2-yl)amino)-3,5-dimethylbenzonitrile, (E)-4-((4-((4-(2-cyanovinyl)-2,6-dimethylphenyl)amino)-6-(3-morpholinopropoxy)-1,3,5-triazin-2-yl)amino)benzonitrile, 4-((4-((2,6-difluoro-4-methylphenyl)amino)-6-(3-morpholino propoxy)-1,3,5-triazin-2-yl)amino)benzonitrile, 4-((4-((4-ethyl-2,6-difluorophenyl) amino)-6-(3-morpholinopropoxy)-1,3,5-triazin-2-yl)amino)benzonitrile, 4-((4-((2,6-difluoro-4-isopropylphenyl)amino)-6-(3-morpholinopropoxy)-1,3,5-triazin-2-yl)amino) benzonitrile, 4-((4-((4-cyclopropyl-2,6-difluorophenyl)amino)-6-(3-morpholinopropoxy)-1,3,5-triazin-2-yl)amino)benzonitrile, 4-((4-((4-(2-cyanoethyl)-2,6-difluorophenyl) amino)-6-(3-morpholinopropoxy)-1,3,5-triazin-2-yl)amino)benzonitrile, 4-((4-(mesitylamino)-6-(2-(piperidin-4-yl)ethoxy)-1,3,5-triazin-2-yl)amino)benzonitrile, 4-((4-(mesitylamino)-6-(3-(piperidin-4-yl)propoxy)-1,3,5-triazin-2-yl)amino)benzonitrile, (E)-4-((4-((4-(2-cyanovinyl)-2,6-difluorophenyl)amino)-6-(3-morpholinopropoxy)-1,3,5-triazin-2-yl)amino) benzonitrile, (E)-4-((4-((4-(2-cyanovinyl)-2,6-dimethylphenyl) amino)-6-((3-morpholinopropyl)amino)-1,3,5-triazin-2-yl)amino)benzonitrile, (E)-4-((4-((4-(2-cyanovinyl)-2,6-difluorophenyl)amino)-6-((3-morpholinopropyl)amino)-1,3,5-triazin-2-yl)amino) benzonitrile, (E)-4-((4-((4-(2-cyanovinyl)-2,6-dimethylphenyl)amino)-6-(3-morpholinopropoxy)pyrimidin-2-yl)amino)benzonitrile, (E)-4-((4-((4-(2-cyanovinyl)-2,6-difluorophenyl)amino)-6-(3-morpholinopropoxy)pyrimidin-2-yl)amino) benzonitrile, (E)-4-((4-((4-(2-cyanovinyl)-2,6-dimethylphenyl)amino)-6-((3-morpholinopropyl)amino)pyrimidin-2-yl)amino)benzonitrile, (E)-4-((4-((4-(2-cyanovinyl)-2,6-difluorophenyl) amino)-6-((3-morpholinopropyl)amino)pyrimidin-2-yl) amino)benzonitrile, and a salt thereof.

13. The method of claim 9, wherein the method further comprises administering to the subject at least one additional therapeutic agent.

14. The method of claim 13, wherein the at least one additional therapeutic is selected from the group consisting of nevirapine, delavirdine, efavirenz, etravirine and rilpivirine.

15. The method of claim 13, wherein the pharmaceutical composition and the at least one additional therapeutic agent are co-administered to the subject.

16. The method of claim 13, wherein the pharmaceutical composition and the at least one additional therapeutic agent are co-formulated.

17. The method of claim 9, wherein the HIV infection in the subject is resistant to at least one therapeutic agent selected from the group consisting of nevirapine, delavirdine, efavirenz, etravirine and rilpivirine.

18. The method of claim 9, wherein the subject is human.

* * * * *